（12）United States Patent
Oosawa

(10) Patent No.: US 10,839,511 B2
(45) Date of Patent: Nov. 17, 2020

(54) SIMILAR CASE SEARCH DEVICE, SIMILAR CASE SEARCH METHOD, AND NON-TRANSITORY COMPUTER READABLE MEDIUM

(71) Applicant: FUJIFILM Corporation, Tokyo (JP)

(72) Inventor: Akira Oosawa, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 667 days.

(21) Appl. No.: 15/275,851

(22) Filed: Sep. 26, 2016

(65) Prior Publication Data

US 2017/0011187 A1 Jan. 12, 2017

Related U.S. Application Data

(63) Continuation of application No. PCT/JP2015/056370, filed on Mar. 4, 2015.

(30) Foreign Application Priority Data

Mar. 27, 2014 (JP) ................................. 2014-066286

(51) Int. Cl.
*G06F 16/51* (2019.01)
*A61B 5/055* (2006.01)
(Continued)

(52) U.S. Cl.
CPC .............. *G06T 7/0012* (2013.01); *A61B 5/00* (2013.01); *A61B 5/055* (2013.01); *A61B 6/00* (2013.01);
(Continued)

(58) Field of Classification Search
CPC ........ G16H 10/00; G16H 10/40; G16H 15/00; G16H 20/00; G16H 20/10; G16H 20/13;
(Continued)

(56) References Cited

U.S. PATENT DOCUMENTS

2006/0242564 A1\* 10/2006 Egger ............. G06F 17/303021
715/210
2008/0031503 A1\* 2/2008 Kanada ................. G06F 19/321
382/128
(Continued)

FOREIGN PATENT DOCUMENTS

JP 2010-237930 A 10/2010

OTHER PUBLICATIONS

International Search Report for PCT/JP2015/056370 dated Apr. 7, 2015.
(Continued)

*Primary Examiner* — Robert W Morgan
*Assistant Examiner* — Charles P Coleman
(74) *Attorney, Agent, or Firm* — Birch, Stewart, Kolasch & Birch, LLP

(57) ABSTRACT

Provided is a similar case search device which rapidly searches for an appropriate similar case on the basis of plural ROIs.
An individual similarity calculation unit sets the ROIs and plural case lesions in a case image so as to be in one-to-one correspondence with each other, compares the feature amounts of the ROIs and the feature amounts of the case lesions which correspond to each other, and calculates an individual similarity for each ROI. A total similarity calculation unit calculates a total similarity for only combinations of completely different types, which are combinations of plural ROIs and plural different types of case lesions in the same case, on the basis of plural individual similarities calculated for each of the plural ROIs. A similar case search unit searches for a similar case on the basis of the total similarities corresponding to the combinations of completely different types.

20 Claims, 51 Drawing Sheets

(51) Int. Cl.
G06T 1/00 (2006.01)
A61B 5/00 (2006.01)
A61B 6/00 (2006.01)
G06T 7/11 (2017.01)
G16H 50/20 (2018.01)
G16H 50/70 (2018.01)
G06F 16/00 (2019.01)
A61B 8/08 (2006.01)
G06T 7/00 (2017.01)
G06F 16/583 (2019.01)
A61B 6/03 (2006.01)
G06F 19/00 (2018.01)

(52) U.S. Cl.
CPC .............. *A61B 6/032* (2013.01); *A61B 6/563* (2013.01); *G06F 16/00* (2019.01); *G06F 16/51* (2019.01); *G06F 16/5838* (2019.01); *G06F 19/321* (2013.01); *G06T 1/00* (2013.01); *G06T 7/11* (2017.01); *G16H 50/20* (2018.01); *G16H 50/70* (2018.01); *A61B 6/502* (2013.01); *A61B 8/08* (2013.01); *G06T 2207/10004* (2013.01); *G06T 2207/30096* (2013.01)

(58) Field of Classification Search
CPC ........ G16H 20/17; G16H 30/00; G16H 40/00; G16H 50/00; G16H 70/00; G16H 80/00; G16H 50/50; G16H 50/70; G16H 50/20; G06F 19/328; G06F 19/3456; G06N 5/04; G06N 5/048

USPC .................................................. 705/2, 3, 20
See application file for complete search history.

(56) References Cited

U.S. PATENT DOCUMENTS

| | | | |
|---|---|---|---|
| 2010/0189366 A1* | 7/2010 | Iizuka ................... | G06F 17/271 382/209 |
| 2011/0085697 A1* | 4/2011 | Clippard .............. | G06K 9/4652 382/100 |
| 2012/0134555 A1* | 5/2012 | Iizuka ................... | G16H 15/00 382/128 |
| 2013/0006087 A1* | 1/2013 | Kondo ................ | G06F 19/3443 600/407 |
| 2013/0114867 A1* | 5/2013 | Kondo .................. | G06F 19/321 382/128 |
| 2013/0259350 A1* | 10/2013 | Sato ....................... | G06Q 10/10 382/131 |
| 2015/0310172 A1* | 10/2015 | Takata ................... | G16H 50/70 382/128 |

OTHER PUBLICATIONS

Written Opinion of the International Searching Authority for PCT/JP2015/056370 (PCT/ISA/237) dated Apr. 7, 2015.
International Search Report for PCT/JP2015/056370 (Form PCT/ISA/210) dated Apr. 7, 2015.
Chinese Office Action and Search Report, dated Dec. 13, 2018 for corresponding Chinese Application No. 201580016673.9, with an English translation of the Chinese Office Action.

* cited by examiner

FIG. 6

| | TYPE OF LESION | LESION PATTERN |
|---|---|---|
| A | ABNORMAL SHADOW OF LOW RESPIRATORY AREA (FOR EXAMPLE, EMPHYSEMA, PNEUMOTHORAX, AND BULLA) | |
| B | VOMICA | |
| C | ABNORMAL SHADOW OF BRONCHUS (FOR EXAMPLE, THICKENED BRONCHIAL WALLS, BRONCHIAL DILATATION, TRACTION BRONCHIECTASIS, AND AIR BRONCHOGRAM) | |
| D | HONEYCOMB LUNG | |
| E | FROSTED GLASS SHADOW | |
| F | PUNCTATE SHADOW (FOR EXAMPLE, NODULAR SHADOW AND TIB) | |
| G | ABNORMAL SHADOW OF HIGH ABSORPTION AREA (FOR EXAMPLE, CONSOLIDATION, NODULE, AND BRONCHIAL MUCOUS GLAND) | |
| H | LINEAR AND RETICULAR SHADOWS | |

FIG. 34

| EXAMINATION ID : O901 | ROI : THREE | | |
|---|---|---|---|
| ROI (No1) | ROI (No2) | ROI (No3) | |

CASE ID: C104
CL : FOUR CLS
OF SAME TYPE
(B1~B4)

| ROI (No1) | ROI (No2) | ROI (No3) | |
|---|---|---|---|
| ISM(C104-11) B1 | ISM(C104-22) B2 | ISM(C104-33) B3 | → EXCLUDED FROM CALCULATION |
| ISM(C104-11) B1 | ISM(C104-22) B2 | ISM(C104-34) B4 | → EXCLUDED FROM CALCULATION |
| ISM(C104-11) B1 | ISM(C104-23) B3 | ISM(C104-32) B2 | → EXCLUDED FROM CALCULATION |
| ISM(C104-11) B1 | ISM(C104-23) B3 | ISM(C104-34) B4 | → EXCLUDED FROM CALCULATION |
| ISM(C104-11) B1 | ISM(C104-24) B4 | ISM(C104-32) B2 | → EXCLUDED FROM CALCULATION |
| ISM(C104-11) B1 | ISM(C104-24) B4 | ISM(C104-33) B3 | → EXCLUDED FROM CALCULATION |
| ISM(C104-12) B2 | ISM(C104-21) B1 | ISM(C104-33) B3 | → EXCLUDED FROM CALCULATION |
| ISM(C104-12) B2 | ISM(C104-23) B3 | ISM(C104-34) B4 | → EXCLUDED FROM CALCULATION |
| ISM(C104-12) B2 | ISM(C104-23) B3 | ISM(C104-31) B1 | → EXCLUDED FROM CALCULATION |
| ISM(C104-12) B2 | ISM(C104-23) B3 | ISM(C104-34) B4 | → EXCLUDED FROM CALCULATION |
| ISM(C104-12) B2 | ISM(C104-24) B4 | ISM(C104-31) B1 | → EXCLUDED FROM CALCULATION |
| ISM(C104-12) B2 | ISM(C104-24) B4 | ISM(C104-33) B3 | → EXCLUDED FROM CALCULATION |
| ISM(C104-13) B3 | ISM(C104-24) B4 | ISM(C104-31) B1 | → EXCLUDED FROM CALCULATION |
| ISM(C104-13) B3 | ISM(C104-24) B4 | ISM(C104-32) B2 | → EXCLUDED FROM CALCULATION |
| ISM(C104-13) B3 | ISM(C104-21) B1 | ISM(C104-32) B2 | → EXCLUDED FROM CALCULATION |
| ISM(C104-13) B3 | ISM(C104-21) B1 | ISM(C104-34) B4 | → EXCLUDED FROM CALCULATION |
| ISM(C104-13) B3 | ISM(C104-22) B2 | ISM(C104-31) B1 | → EXCLUDED FROM CALCULATION |
| ISM(C104-13) B3 | ISM(C104-22) B2 | ISM(C104-34) B4 | → EXCLUDED FROM CALCULATION |
| ISM(C104-14) B4 | ISM(C104-21) B1 | ISM(C104-32) B2 | → EXCLUDED FROM CALCULATION |
| ISM(C104-14) B4 | ISM(C104-21) B1 | ISM(C104-33) B3 | → EXCLUDED FROM CALCULATION |
| ISM(C104-14) B4 | ISM(C104-22) B2 | ISM(C104-32) B2 | → EXCLUDED FROM CALCULATION |
| ISM(C104-14) B4 | ISM(C104-22) B2 | ISM(C104-33) B3 | → EXCLUDED FROM CALCULATION |
| ISM(C104-14) B4 | ISM(C104-23) B3 | ISM(C104-31) B1 | → EXCLUDED FROM CALCULATION |
| ISM(C104-14) B4 | ISM(C104-23) B3 | ISM(C104-32) B2 | → EXCLUDED FROM CALCULATION |

FIG. 35

| CASE ID | NUMBER OF REGISTERED CASE LESIONS | SEARCH TARGET | NUMBER OF TYPES OF CASE LESIONS CL | BREAKDOWN OF TYPE OF CASE LESION ||| NUMBER OF TOTAL SIMILARITIES TSM CALCULATED |
|---|---|---|---|---|---|---|---|
| | | | | ROI(No1) B VOMICA | ROI(No2) F PUNCTATE SHADOW | ROI(No1) E FROSTED GLASS SHADOW | |
| C101 | 3 | TARGET CASE | 3 | 1 | 1 | 1 | 6 |
| C102 | 5 | TARGET CASE | 3 | 3 | 1 | 1 | 18 |
| C103 | 4 | NON-TARGET CASE | 2 | 3 | 1 | - | - |
| C104 | 4 | NON-TARGET CASE | 1 | 4 | - | - | - |
| C105 | 3 | TARGET CASE | 3 | 1 | 1 | 1 | 6 |
| C106 | 5 | TARGET CASE | 3 | 2 | 2 | 1 | 24 |

21 — EXAMINATION ID: O901 | ROI(No1) RAC1 | ROI(No2) RAC2 | ROI(No3) RAC3

72

| TSM TABLE FOR EXAMINATION ID: O901 | | | | |
|---|---|---|---|---|
| CASE ID | TOTAL SIMILARITY (TSM) | COMBINATION PATTERNS OF INDIVIDUAL SIMILARITIES (ISM) | | |
| C101 | TSM (C101-1) = 1.4 | ISM(C101-11) | ISM(C101-22) | ISM(C101-33) |
| C101 | TSM (C101-2) = 2.04 | ISM(C101-11) | ISM(C101-23) | ISM(C101-32) |
| C101 | TSM (C101-3) = 1.32 | ISM(C101-12) | ISM(C101-21) | ISM(C101-33) |
| C101 | TSM (C101-4) = 1.52 | ISM(C101-12) | ISM(C101-23) | ISM(C101-31) |
| C101 | TSM (C101-5) = 1.98 | ISM(C101-13) | ISM(C101-21) | ISM(C101-32) |
| C101 | TSM (C101-6) = 1.54 | ISM(C101-13) | ISM(C101-22) | ISM(C101-31) |
| C102 | TSM (C102-1) = 2.02 | ISM(C102-11) | ISM(C102-24) | ISM(C102-35) |
| C102 | TSM (C102-2) = 1.96 | ISM(C102-12) | ISM(C102-24) | ISM(C102-35) |
| C102 | TSM (C102-3) = 2.23 | ISM(C102-13) | ISM(C102-24) | ISM(C102-35) |
| C102 | TSM (C102-4) = 1.72 | ISM(C102-11) | ISM(C102-25) | ISM(C102-34) |
| ⋮ | | | | |
| C102 | TSM (C102-18) = 1.56 | ISM(C102-15) | ISM(C102-24) | ISM(C102-33) |
| ⋮ | | | | |
| C106 | TSM (C106-18) = 1.03 | ISM(C106-15) | ISM(C106-25) | ISM(C106-35) |
| ⋮ | | | | |

FIG. 44

| CASE ID | NUMBER OF REGISTERED CASE LESIONS | SEARCH TARGET | NUMBER OF TYPES OF CASE LESIONS CL | BREAKDOWN OF TYPE OF CASE LESION | | | NUMBER OF TOTAL SIMILARITIES TSM CALCULATED |
|---|---|---|---|---|---|---|---|
| | | | | ROI(No1) B VOMICA | ROI(No2) F PUNCTATE SHADOW | ROI(No1) E FROSTED GLASS SHADOW | |
| C101 | 3 | TARGET CASE | 3 | 1 | 1 | 1 | 6 |
| C102 | 5 | TARGET CASE | 3 | 3 | 1 | 1 | 18 |
| C103 | 4 | TARGET CASE | 2 | 3 | 1 | - | 18 |
| C104 | 4 | NON-TARGET CASE | 1 | 4 | - | - | - |
| C105 | 3 | TARGET CASE | 3 | 1 | 1 | 1 | 6 |
| C106 | 5 | TARGET CASE | 3 | 2 | 2 | 1 | 18 |

...

SIMILAR CASE SEARCH DEVICE, SIMILAR CASE SEARCH METHOD, AND NON-TRANSITORY COMPUTER READABLE MEDIUM

CROSS-REFERENCE TO RELATED APPLICATION

This application is a Continuation of PCT International Application PCT/JP2015/056370 filed on 4 Mar. 2015, which claims priority under 35 USC 119 (a) from Japanese Patent Application No. 2014-066286 filed on 27 Mar. 2014. The above application is hereby expressly incorporated by reference, in its entirety, into the present application.

BACKGROUND OF THE INVENTION

1. Field of the Invention

The present invention relates to a similar case search device, a similar case search method, and a non-transitory computer readable medium.

2. Description of the Related Art

In the medical field, a similar case search device has been known which searches for a past case that is similar to an examination image on the basis of the examination image (for example, see JP2010-237930A and JP2012-118583A (US2012/134555A)). The examination image is, for example, an image captured by a modality, such as a computed tomography (CT) apparatus that performs tomography or a general X-ray apparatus that captures a simple transparent image, and is used to diagnose a patient, for example, to specify the disease of a patient. In some cases, in one examination operation using the general X-ray apparatus, only one examination image is captured or a plurality of examination images are captured. In one examination operation using the CT apparatus, a plurality of tomographic images (slice images) are acquired. Therefore, one examination data item includes one or more examination images. In many cases, the past examination data is accumulated to create a case. Therefore, data of one case includes one or more case images.

In a case in which a similar case search is performed, first, a user, such as a doctor, designates a region of interest in an examination image. The region of interest indicates a region in which the doctor is particularly interested in the examination image and which includes a lesion to be diagnosed. The similar case search device compares a feature amount which is obtained by quantifying the features of one region of interest designated in the examination image and a feature amount which is obtained by quantifying the features of one lesion in a case image and determines the similarity therebetween. Here, for convenience of explanation, a lesion which is included in the region of interest of the examination image is referred to as a target lesion and a lesion which is included in the case image is referred to as a case lesion. Then, the similar case search device searches for a case including a case lesion that is similar to the region of interest from a case database storing a plurality of cases.

In general, the users designate the region of interest including a target lesion, using different methods, and a variation in search, that is, a variation in the search result occurs due to the difference between individuals. JP2010-237930A discloses a technique which reduces the variation in search. Specifically, even in a case in which a region including the same target lesion is designated as the region of interest, the shape or size of the designated region varies due to the difference in how the user designates the region of interest. As a result, a feature amount is likely to be changed. In the event that the feature amount is changed, similarity is also changed, which results in a variation in search in which the search result varies depending on the user. In JP2010-237930A, in order to reduce the variation in search, for example, the feature amount of each of a plurality of regions of interest in which one target lesion is designated by different methods is calculated, similarity is calculated on the basis of the average value of the calculated feature amounts of the plurality of regions of interest, and a similar image is searched. According to this structure, it is possible to reduce a variation in search due to the difference in designation between the users.

JP2012-118583A (US2012/134555A) relates to a technique that outputs the search result which is more suitable than the subjective feeling of the user on similarity. Specifically, in a case in which the same type of target lesion is present in a plurality of examination images, in the event that a region of interest is designated, the regions of interest including a plurality of target lesions of the same type which the user feels to be similar to each other are put into one group as a group of the same type of target lesions. In one examination data item, a feature amount range including all of the feature amounts of a plurality of target lesions belonging to the group of the same type of target lesions is calculated and a similar case search is performed, using the feature amount range as a search condition. Since it is considered that the feature amount range of the group of the same type of target lesions is equal to that of the target lesions which the user subjectively feels to be similar to each other, the search result is more suitable than the subjective feeling of the user.

However, in some cases, a plurality of target lesions appear in an examination image depending on a disease, which is a basis for specifying a disease. For example, in the case of tuberculosis, a disease is specified on the basis of three types of target lesions, that is, a vomica shadow (cavity), a punctate shadow (small nodules), and a frosted glass shadow (ground glass opacity), which appear in an examination image. In the case of diffuse panbronchiolitis, a disease is specified on the basis of two types of target lesions, that is, an abnormal shadow of the bronchus and a punctate shadow. In the case of a cancer, a case that is similar to a single target lesion may be searched. In the case of non-cancerous diseases other than cancer, it is necessary to search for a case that is similar to a plurality of target lesions.

In the similar case search devices disclosed in JP2010-237930A and JP2012-118583A (US2012/134555A), attention is paid to one target lesion included in the examination image and a similar case is searched on the basis of the feature amount of the region of interest including one target lesion to which attention is paid. However, it is not considered that attention is paid to each of a plurality of target lesions included in the examination images.

As described above, in JP2010-237930A, the feature amount is calculated for each region of interest. A plurality of regions of interest are designated by different methods, but have the same target lesion. Therefore, JP2010-237930A does not disclose a technique that pays attention to the feature amounts of a plurality of regions of interest including different target lesions and searches for a similar case. In addition, in JP2012-118583A (US2012/134555A), for a plurality of target lesions included in a plurality of examination images, one search condition is created for one group of the same type of target lesions and a similar case is searched under the created search condition. In other words, in JP2012-118583A (US2012/134555A), the feature amount common to the regions of interest including a plurality of target lesions of the same type is calculated according to the user's preference. However, JP2012-118583A (US2012/134555A) does not disclose a technique that pays attention to the feature amounts of a plurality of regions of interest including a plurality of target lesions and searches for a similar case.

As disclosed in JP2010-237930A and JP2012-118583A (US2012/134555A), in the technique that pays attention to the feature amount of one region of interest, in a case in which there are a plurality of regions of interest, it is difficult to appropriately search for a similar case. Therefore, the inventors studied a technique that, in a case in which there were a plurality of regions of interest, paid attention to the plurality of regions of interest and searched for a similar case from the cases having a plurality of case lesions registered therein. However, in order to pay attention to a plurality of regions of interest, it is necessary to compare the feature amounts of a plurality of regions of interest and a plurality of case lesions, using the correspondence between the plurality of regions of interest and the plurality of case lesions. In this case, the number of combination patterns that correspond to each other increases, which causes a new problem that the search time increases. As the number of regions of interest increases, the problem becomes more remarkable.

SUMMARY OF THE INVENTION

An object of the invention is to provide a similar case search device and a similar case search method that can appropriately search for a similar case in a short time even in a case in which there are a plurality of regions of interest, and a non-transitory computer readable medium.

A similar case search device according to the invention searches for a similar case which is similar to an examination image used to diagnose a patient from a case database in which a plurality of cases, each of which includes one or more case images, are registered. The similar case search device comprises a feature amount acquisition unit, an individual similarity calculation unit, a total similarity calculation unit, and a similar case search unit. The feature amount acquisition unit acquires feature amounts of a plurality of regions of interest, each of which is designated so as to include one or more different target lesions that are lesions in the examination images, in examination data including one or more examination images. The individual similarity calculation unit sets the regions of interest and a plurality of case lesions in the case image so as to be in one-to-one correspondence with each other, compares the feature amounts of the regions of interest and feature amounts of the case lesions which correspond to each other, and calculates an individual similarity for each region of interest. The total similarity calculation unit calculates a total similarity for only combinations of completely different types, which are combinations of the plurality of regions of interest and a plurality of different types of case lesions in the same case, on the basis of a plurality of individual similarities calculated for each of the plurality of regions of interest. The similar case search unit searches for the similar case on the basis of the total similarities corresponding to the combinations of completely different types.

Here, the case in which a plurality of case lesions are present in the case images includes a case in which a plurality of case lesions are present in one case image and a case in which the sum of the case lesions that are present in a plurality of case images is two or more, for example, a case in which one case lesion is present in each of two case images.

Preferably, the total similarity calculation unit creates the combinations of completely different types which correspond to the number of regions of interest, the number of types of case lesions, and the number of case lesions and calculates the total similarities for each of the combinations of completely different types. Specifically, the total similarity calculation unit may calculate individual similarities for case lesions included in one case, create combinations of completely different types of the calculated individual similarities, and calculate the total similarities. In addition, the total similarity calculation unit may calculate individual similarities for the case lesions in all of the cases and create combinations of completely different types of the individual similarities for each case. In both cases, after the individual similarities ISM are calculated, combinations of completely different types of the individual similarities ISM are created.

In a case in which there are a plurality of case lesions of at least one type among a plurality of different types of case lesions included in the same case, preferably, the total similarity calculation unit distinguishes the plurality of case lesions of the same type and creates the combinations of completely different types for each of the distinguished case lesions of the same type.

Preferably, the similar case search unit creates a similar case list which is a list of information related to the plurality of similar cases on the basis of the total similarities. Preferably, in the similar case list, the similar cases are sorted in an order of the total similarity.

Preferably, display items of the similar case list include a value of the total similarity and breakdown information related to the total similarity and the breakdown information includes a correspondence relationship between the region of interest and the case lesion for calculating the individual similarity. Preferably, in addition to the value of the total similarity, values of the plurality of individual similarities which are elements for calculating the total similarity are displayed in the similar case list. Preferably, images of the region of interest and the case lesion are displayed in the similar case list.

Preferably, the case database stores information about the type of case lesion. Preferably, the total similarity is a sum of a plurality of individual similarities included in the combinations of completely different types.

The individual similarity calculation unit may create an individual similarity table, in which a plurality of individual similarities that are calculated by a correspondence between each region of interest and a plurality of case lesions are recorded, for each region of interest. The total similarity calculation unit may read out the individual similarities one by one from a plurality of individual similarity tables created for each region of interest and create the combinations of completely different types, using the plurality of read individual similarities as elements.

Preferably, the individual similarity calculation unit calculates the individual similarity for a case in which at least the number of types of case lesions is two or more among the cases and does not calculate the individual similarity for a case in which the number of types of case lesions is one.

The total similarity calculation unit may perform a weighting process for the total similarity according to values of the individual similarities which are elements for calculating the total similarity. Preferably, in a case in which the individual similarity is equal to or greater than a threshold value, the weighting process increases the total similarity.

The similar case search unit may exclude a case in which the number of types of case lesions is less than the number of regions of interest from a search target. In addition, the similar case search unit sets a case in which the number of types of case lesions is less than the number of regions of interest and is two or more, as a search target.

Preferably, the similar case search device further includes a representative value determination unit that, in a case in which a plurality of total similarities are calculated by a correspondence between one region of interest and a plurality of case lesions included in one case, determines one representative value from the plurality total similarities. Preferably, the similar case search unit searches for the similar case on the basis of the representative value.

A similar case search method according to the invention searches for a similar case which is similar to an examination image used to diagnose a patient from a case database in which a plurality of cases, each of which includes one or more case images, are registered. The similar case search method comprises a feature amount acquisition step, an individual similarity calculation step, a total similarity calculation step, and a similar case search step. In the feature amount acquisition step, feature amounts of a plurality of regions of interest, each of which is designated so as to include one or more different target lesions that are lesions in the examination images, in examination data including one or more examination images are acquired. In the individual similarity calculation step, the regions of interest and a plurality of case lesions in the case image are set so as to be in one-to-one correspondence with each other. The feature amounts of the regions of interest and feature amounts of the case lesions which correspond to each other are compared with each other and an individual similarity is calculated for each region of interest. In the total similarity calculation step, a total similarity is calculated for only combinations of completely different types, which are combinations of the plurality of regions of interest and a plurality of different types of case lesions in the same case, on the basis of a plurality of individual similarities calculated for each of the plurality of regions of interest. In the similar case search step, the similar case is searched on the basis of the total similarities corresponding to the combinations of completely different types.

In the total similarity calculation step, the combinations of completely different types may be created for the case lesions in each case and the individual similarities corresponding to the created combinations may be calculated. The individual similarities may be calculated for all of the cases and then combinations of completely different types of the individual similarities may be created for each case. In both cases, after the individual similarities ISM are calculated, combinations of completely different types of the individual similarities ISM are created.

A non-transitory computer readable medium according to the invention stores a computer-executable program enabling execution of computer instructions to perform operations for searching for a similar case which is similar to an examination image used to diagnose a patient from a case database in which a plurality of cases, each of which includes one or more case images, are registered. The operations include acquiring feature amounts of a plurality of regions of interest, each of which is designated so as to include one or more different target lesions that are lesions in the examination images, in examination data including one or more examination images, setting the regions of interest and a plurality of case lesions in the case image so as to be in one-to-one correspondence with each other, comparing the feature amounts of the regions of interest and feature amounts of the case lesions which correspond to each other, and calculating an individual similarity for each region of interest, calculating a total similarity for only combinations of completely different types, which are combinations of the plurality of regions of interest and a plurality of different types of case lesions in the same case, on the basis of a plurality of individual similarities calculated for each of the plurality of regions of interest, and searching for the similar case on the basis of the total similarities corresponding to the combinations of completely different types.

The feature amounts of the regions of interest are compared with the feature amounts of the case lesions to calculate the individual similarities for each region of interest. The total similarity is calculated for only combinations of completely different types, which are combinations of a plurality of regions of interest and a plurality of different types of case lesions in the same case, on the basis of the individual similarities. A similar case is searched on the basis of the calculated total similarity. Therefore, it is possible to provide a similar case search device and a similar case search method that can appropriately search for a similar case in a short time even in a case in which there are a plurality of regions of interest, and a non-transitory computer readable medium.

BRIEF DESCRIPTION OF THE DRAWINGS

FIG. 6 is a diagram illustrating image patterns of the types of lesions.

FIG. 34 is a diagram illustrating other cases which are excluded from search targets.

FIG. 35 is a table illustrating cases which are search targets and cases which are not search targets.

FIG. 36 is a diagram illustrating a total similarity table in which total similarities are calculated.

FIG. 44 is a diagram illustrating a second embodiment.

DESCRIPTION OF THE PREFERRED EMBODIMENTS

First Embodiment

Figure 1:
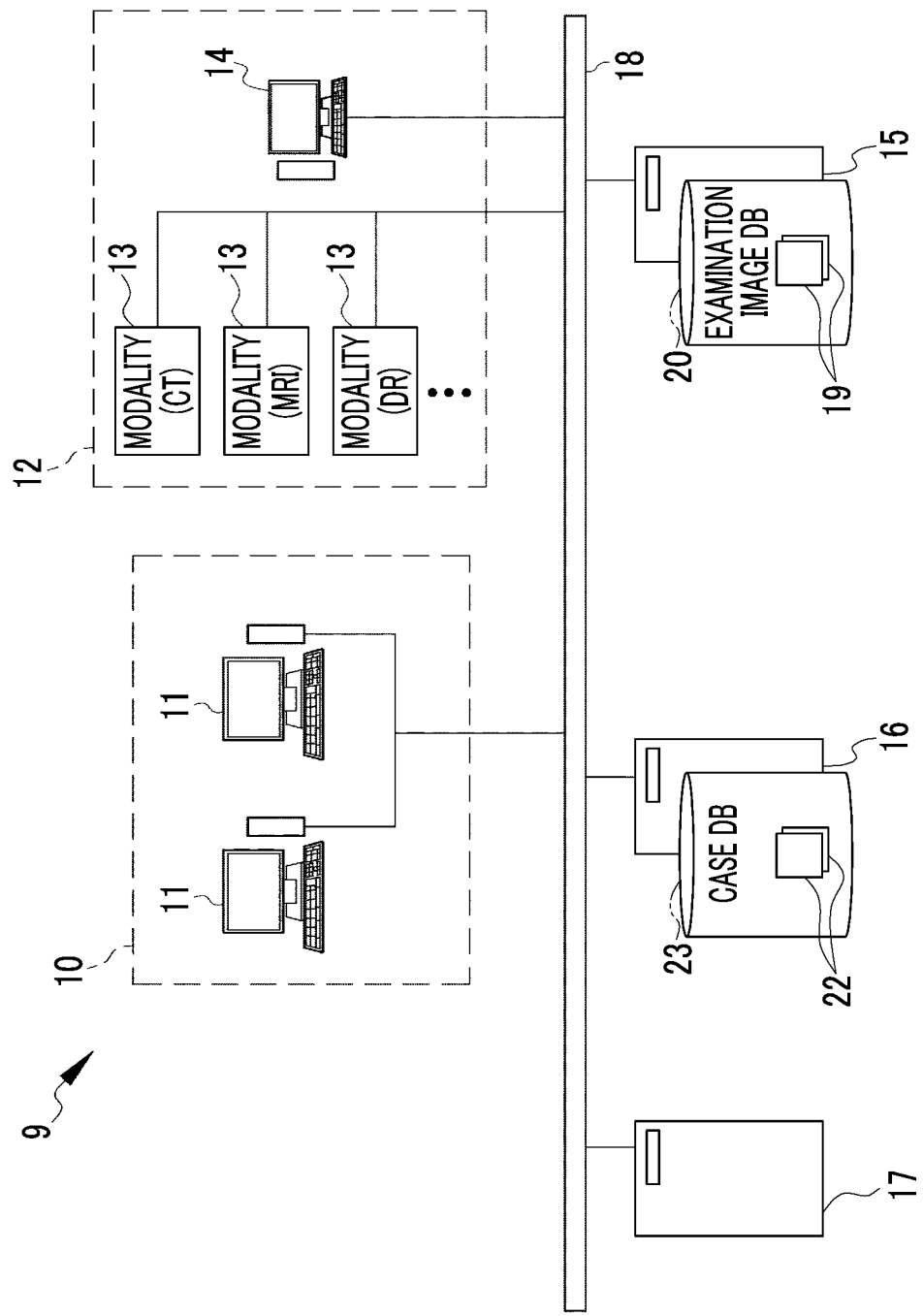
FIG. 1 is a diagram illustrating the structure of a medical information system including a similar case search server.

A medical information system 9 illustrated in FIG. 1 is constructed in a medical facility such as a hospital. The medical information system 9 includes a treatment department terminal 11 that is provided in a treatment department 10, a modality (medical imaging apparatus) 13 and an order management terminal 14 that are provided in an examination department 12, an examination image database (hereinafter, referred to as a "DB") server 15, a case DB server 16, and a similar case search server 17. These components are connected through a network 18 such that they can communicate with each other. The network 18 is, for example, a local area network (LAN) which is constructed in a hospital. The modality 13 includes a computed tomography (CT) apparatus or a magnetic resonance imaging (MRI) apparatus that captures tomographic images and a general X-ray apparatus (for example, digital radiography (DR) or computed radiography (CR)) that captures simple transparent images.

The treatment department terminal 11 is operated by a doctor (to which letters "Dr" are attached in the drawings) in the treatment department 10 to input or browse electronic medical records and to issue an examination order for examination to the examination department 12. In addition, the treatment department terminal 11 is used as an image display terminal that displays an examination image 19 which has been captured in the examination department 12 and then stored in the examination image DB server 15 such that the doctor can browse the examination image 19.

In the examination department 12, the order management terminal 14 receives the examination order from the treatment department 10 and manages the received examination order. A technician in the examination department 12 takes a radiographic image of a patient using the modality 13 according to the content of the examination order. One or a plurality of examination images 19 are captured in response to one examination order. In the event that imaging ends, the modality 13 transmits the captured examination image 19 to the examination image DB server 15. In the event that examination ends, the doctor in the treatment department 10 is notified of the end of the examination from the examination department 12 and is also notified of the storage destination of the examination image 19 in the examination image DB server 15. The doctor in the treatment department 10 accesses the examination image DB server 15 through the treatment department terminal 11 and browses the examination image 19 using the treatment department terminal 11.

The examination image DB server 15 includes an examination image DB 20 that stores a plurality of examination images 19 and is a so-called picture archiving and communication system (PACS) server. The examination image DB 20 is a database which can be searched by keyword and transmits an examination image 19 matched with search conditions or a designated examination image 19 in response to, for example, a search request or a transmission request from the treatment department terminal 11.

Figure 2:
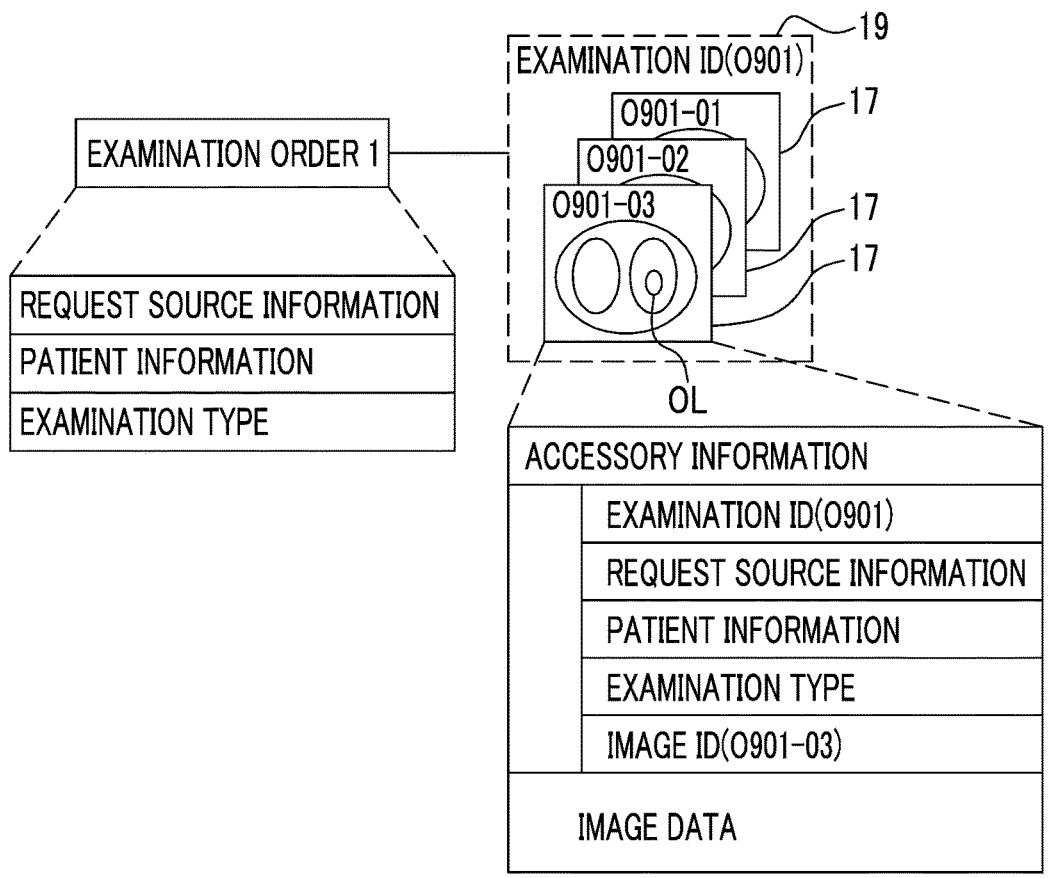
FIG. 2 is a diagram schematically illustrating examination data including a plurality of examination images.
Figure 3:
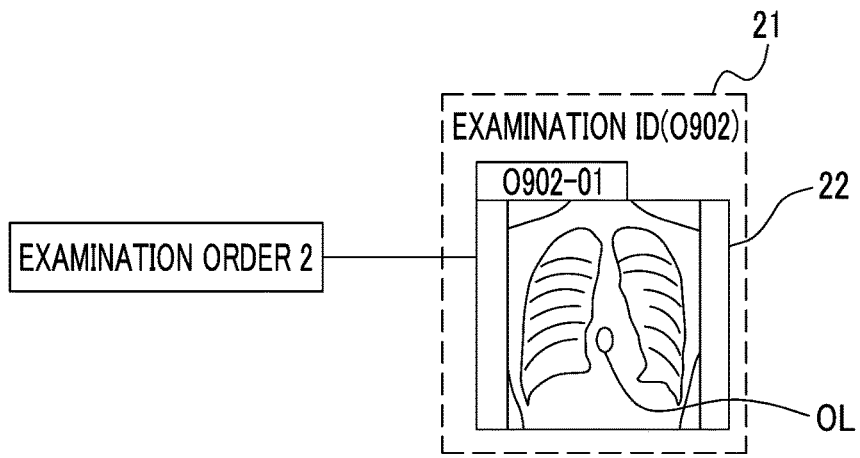
FIG. 3 is a diagram schematically examination data including one examination image.

As illustrated in FIGS. 2 and 3, in the examination image DB 20, one examination data item 21 including one or more examination images 19 is stored so as to be associated with one examination order. As illustrated in FIG. 2, the examination image 19 captured by the CT apparatus or the MRI apparatus is a tomographic image (also referred to as a slice image) and one examination data item 21 includes a plurality of examination images 19. As illustrated in FIG. 3, the examination image 19 captured by the general X-ray apparatus is a simple transparent image. One examination data item 21 may include only one examination image 19 or a plurality of examination images 19.

The examination order includes, for example, information about a request source, such as the ID (identification data) or position of the doctor in the treatment department 10, patient information, and the type of examination. An image file of the examination image 19 includes image data and accessory information such as a digital imaging and communication in medicine (DICOM) header. Examination order information is stored as the accessory information of the examination image 19. In addition, the accessory information includes an examination ID and an image ID which is given to each examination image 19. In the example illustrated in FIGS. 2 and 3, the examination ID is "O901" or "O902" and the image ID is given in the form in which a serial number for identifying one examination image 19 is added to the examination ID. For example, the image ID is "O901-03" or "O901-01". The examination image DB server 15 can perform a search, using an item included in a DICOM tag as a search key.

The similar case search server 17 receives the examination image 19 as search conditions and searches for a case including a case image 22 that is similar to the received examination image 19. The case image 22 is an examination image that was used for diagnosis in the past. The case DB server 16 includes a case DB 23 that stores a plurality of cases such that the cases can be searched. The similar case search server 17 accesses the case DB server 16, reads out the cases one by one, compares the examination image 19 which has been received as the search conditions with the case image 22 in the case, and searches for a case that is similar to the examination image 19.

Figure 4:
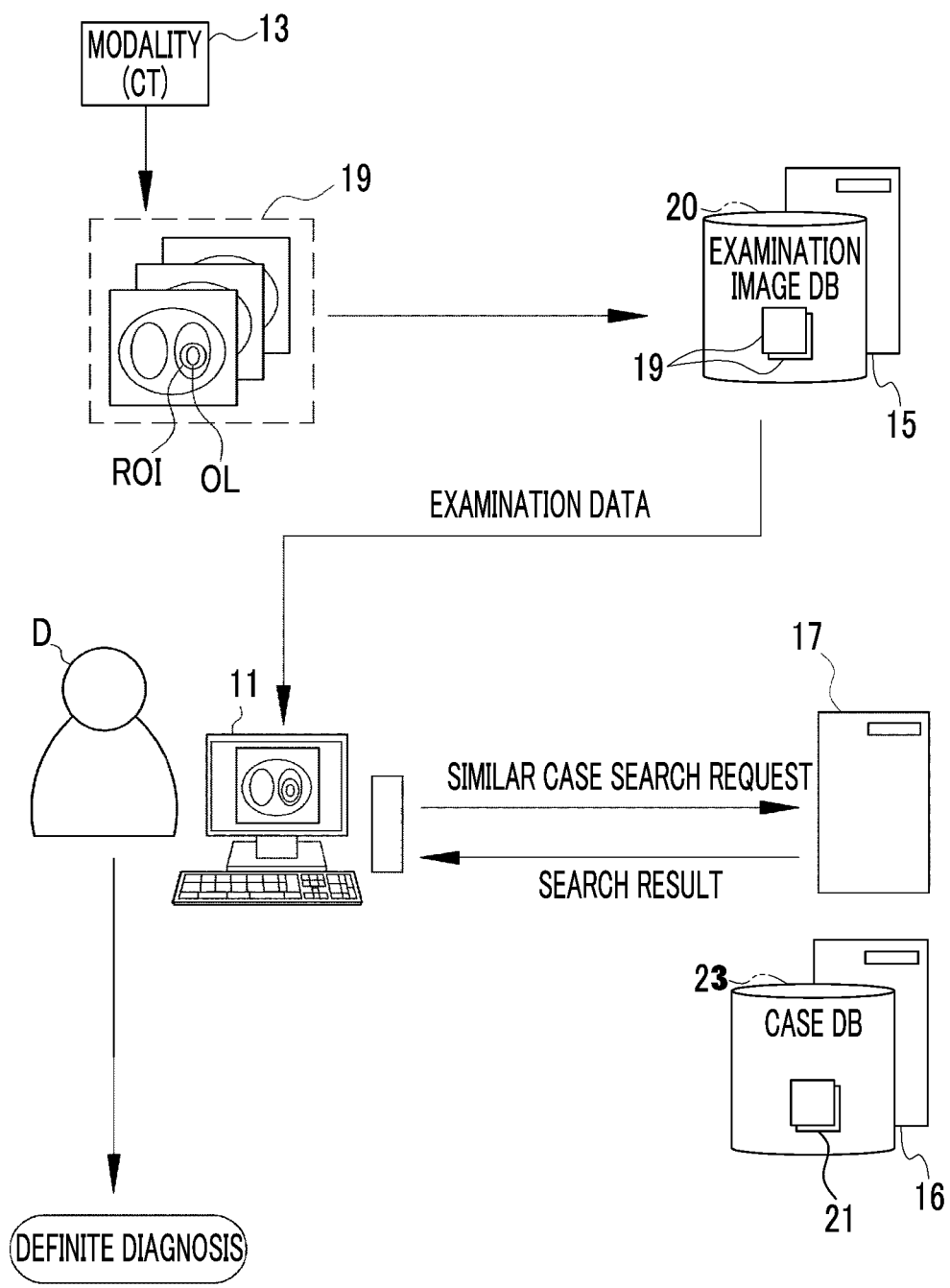
FIG. 4 is a diagram illustrating the functions of a treatment department, an examination department, an examination image DB server, and a case DB server.

As illustrated in FIG. 4, the doctor in the treatment department 10 accesses the examination image DB server 15 and downloads examination data 21 including the examination images 19, using the treatment department terminal 11. The examination image 19 is displayed on the treatment department terminal 11 and is browsed by the doctor. In a case in which a patient has a disease, a lesion (also referred to as a target lesion OL) indicating the symptoms of the disease is included in the examination image 19 of the patient. The doctor in the treatment department 10 selects an examination image 19 including the target lesion OL from the examination images 19 included in the examination data 21. The examination image 19 is added to a similar case search request that is issued from the treatment department terminal 11 to the similar case search server 17 and the similar case search request is transmitted to the similar case search server 17. In the event of receiving the similar case search request, the similar case search server 17 searches for a case similar to the examination image 19 from the case DB server 16 and transmits the search result to the treatment department terminal 11 which is a request source.

The doctor in the treatment department 10 checks the case included in the examination result. The case includes a radiogram interpretation report associated with the case image 22. The doctor makes a definite diagnosis, such as the specification of a disease in the examination image 19, with reference to, for example, an opinion on the case image 22 which is written in the radiogram interpretation report.

Figure 5:
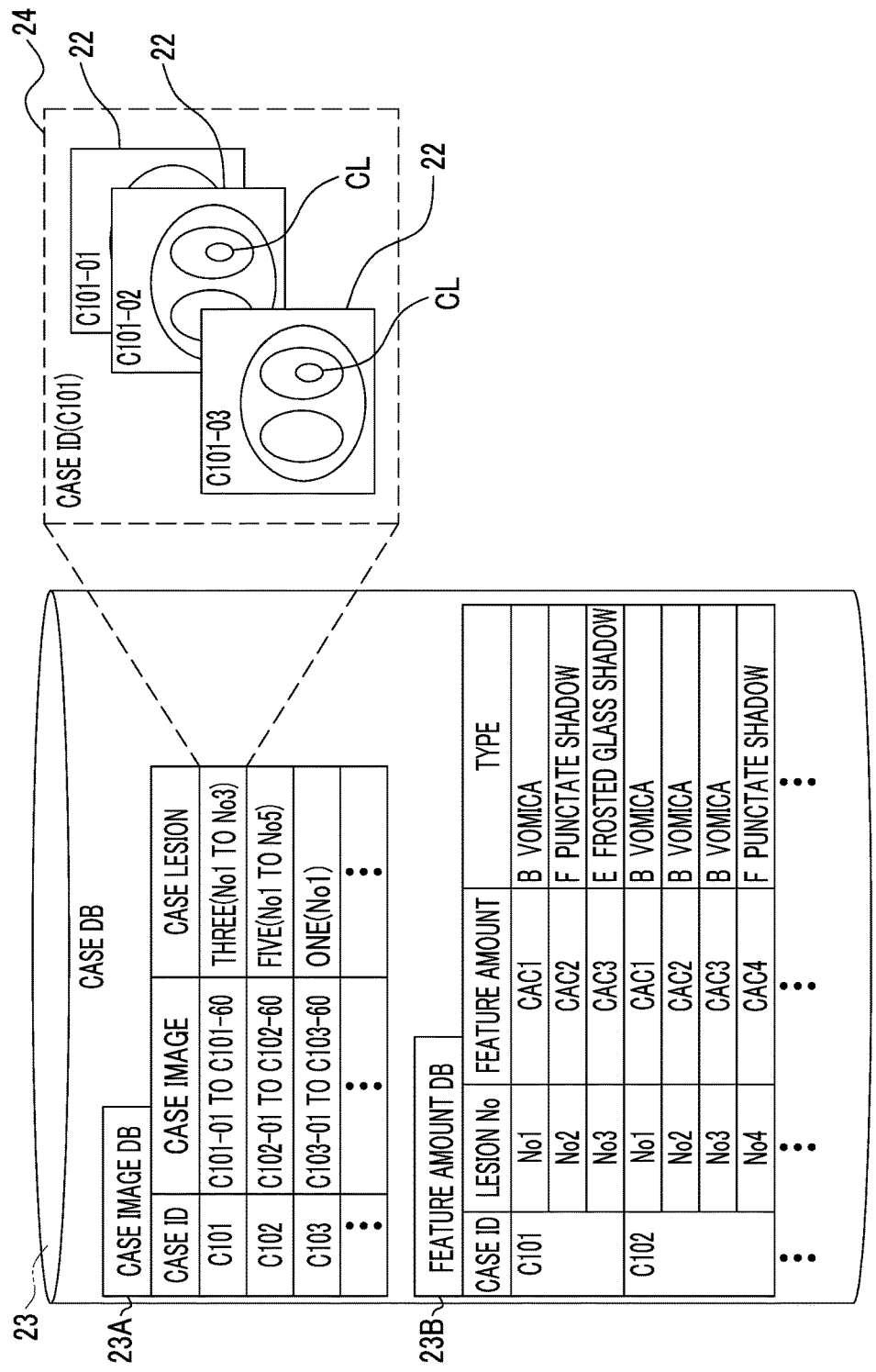
FIG. 5 is a diagram illustrating a case DB.

As illustrated in FIG. 5, the case DB 23 includes a case image DB 23A and a feature amount DB 23B. The case image DB 23A is a database which stores the case image 22 such that the case image 22 can be searched. A case ID is given to each case. The case ID corresponds to the examination ID in the examination image 19. One case includes one or more case images 22. Similarly to the examination image 19, an image ID in which a serial number is added to the case ID is given to each case image 22. In FIG. 5, case data 24 with a case ID "C101" includes, for example, 60 tomographic images.

The case image 22 includes a lesion (case lesion CL) indicating the symptoms of a disease. One or more case lesions CL are registered in one case. In this example, three case lesions CL with No1 to No3 are registered in a case with a case ID "C101", two case lesions CL are registered in a case with a case ID "C102", and one case lesion CL is registered in a case with a case ID "C103". The case lesion CL is a region that was designated as a lesion by the doctor in the event that the case image 22 was used as the examination image for diagnosis in the past and was registered as the case lesion CL by the doctor through a definite diagnosis. A method for designating the case lesion CL is the same as, for example, a method for designating a region of interest ROI which will be described below.

The feature amount DB 23B is a database that stores the feature amount CAC of an image of the case lesion CL. An ID including the case ID and a lesion number (No) is given to the feature amount CAC. For example, there are three case lesions CL in the case with the case ID "C101" and serial numbers No1 to No3 in one case are given to each case lesion CL. A number following the feature amount CAC corresponds to the serial number in the case. A method for calculating the feature amount CAC is the same as, for example, a method for calculating the region of interest ROI which will be described below.

The feature amount DB 23B stores information (type information) related to the type of each case lesion CL. As illustrated in FIG. 6, lesion patterns, which are the image patterns of typical lesions, are classified into, for example, eight types A to H. That is, the lesion patterns are classified into A: an abnormal shadow of a low respiratory area (low attenuation area, such as emphysema, pneumothorax, or bulla), B: vomica, C: an abnormal shadow of the bronchus (such as thickened bronchial walls, bronchial dilatation, traction bronchiectasis, or air bronchogram), D: a honeycomb lung (honeycombing), E: a frosted glass shadow (ground glass opacity), F: a punctate shadow (small nodules, such as a nodular shadow or TIB), G: an abnormal shadow of a high absorption area (high attenuation area, such as consolidation, nodule, or bronchial mucous gland (mucoid impaction)), and H: linear and reticular shadows.

The type of case lesion CL is determined on the basis of which of the eight types of lesion patterns the image pattern of the case lesion CL is closest to. The type of case lesion CL is determined on the basis of the feature amount CAC. The feature amount CAC is an eight-dimensional feature vector that is formed by output values from eight types of discriminators corresponding to eight types of lesion patterns, similarly to the region of interest ROI which will be described below. The type information of the case lesion CL and the feature amount CAC are stored in the feature amount DB 23B. In this example, the typical lesion patterns are classified into eight types and the lesions are also classified into eight types. However, the number of types may be less than 8 or equal to or greater than 8.

Figure 7:
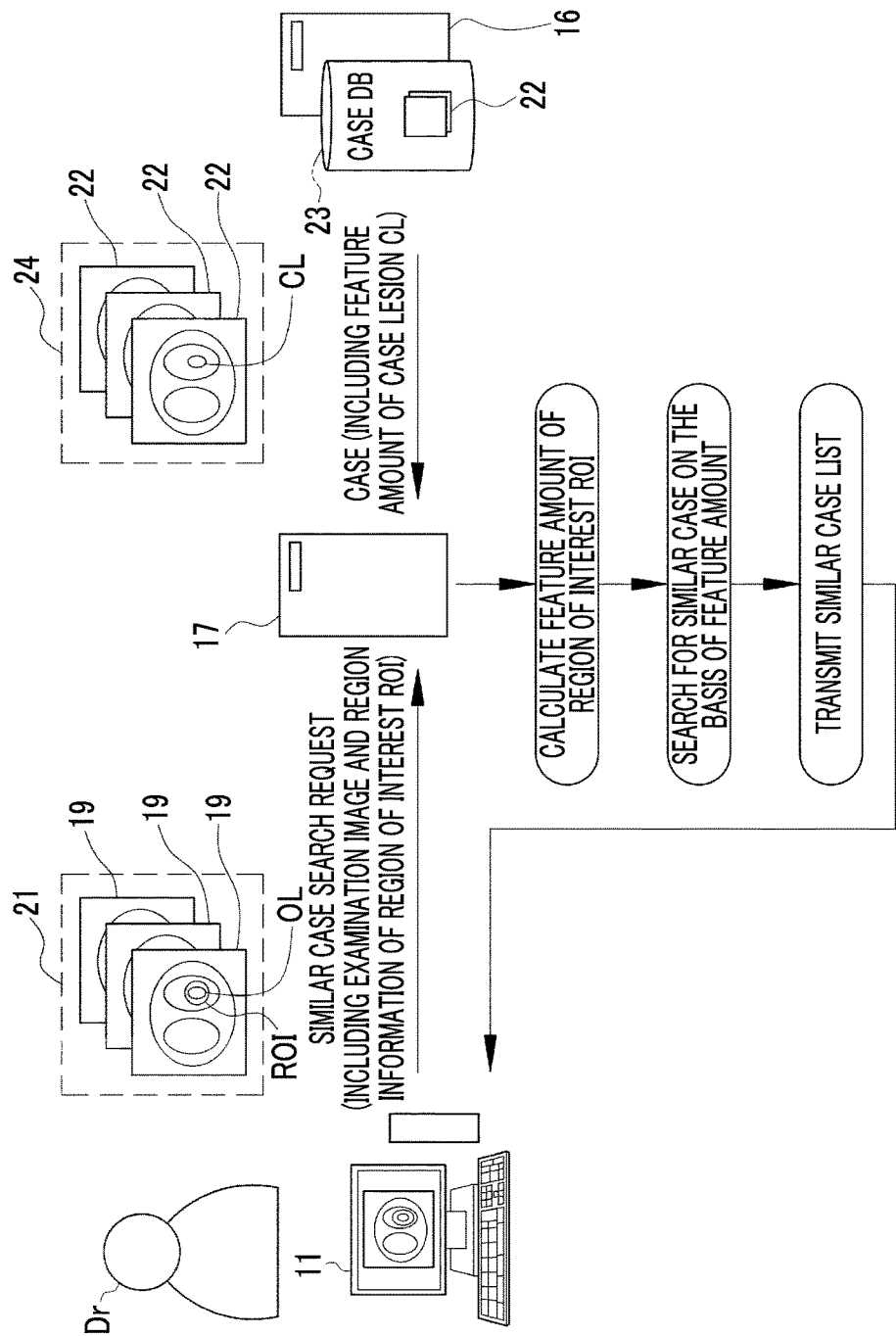
FIG. 7 is a diagram illustrating the outline of the functions of a similar case search server.

As illustrated in FIG. 7, in the event that a similar case search request is issued through the treatment department terminal 11, the doctor designates a region including the target lesion OL in the examination image 19 as the region of interest ROI. The examination image 19 including the target lesion OL and information about a region which corresponds to the designated region of interest ROI in the examination image 19 (for example, information about coordinates in the examination image 19) are added to the similar case search request. In the event of receiving the similar case search request, the similar case search server 17 specifies the region of interest ROI on the basis of image data of the examination image 19 and the region information. Then, the similar case search server 17 calculates the feature amount of the region of interest ROI. After calculating the feature amount, the similar case search server 17 reads out the cases one by one from the case DB server 16, compares the feature amounts of the region of interest ROI and the case lesion CL, and searches for similar cases. Then, the similar case search server 17 creates a similar case list which is a list of information related to a plurality of similar cases and transmits the similar case list as the search result to the treatment department terminal 11.

The treatment department terminal 11, the order management terminal 14, the examination image DB server 15, the case DB server 16, and the similar case search server 17 are implemented by installing a control program, such as an operating system, or an application program, such as a client program or a server program, in computers, such as personal computers, server computers, or workstations.

Figure 8:
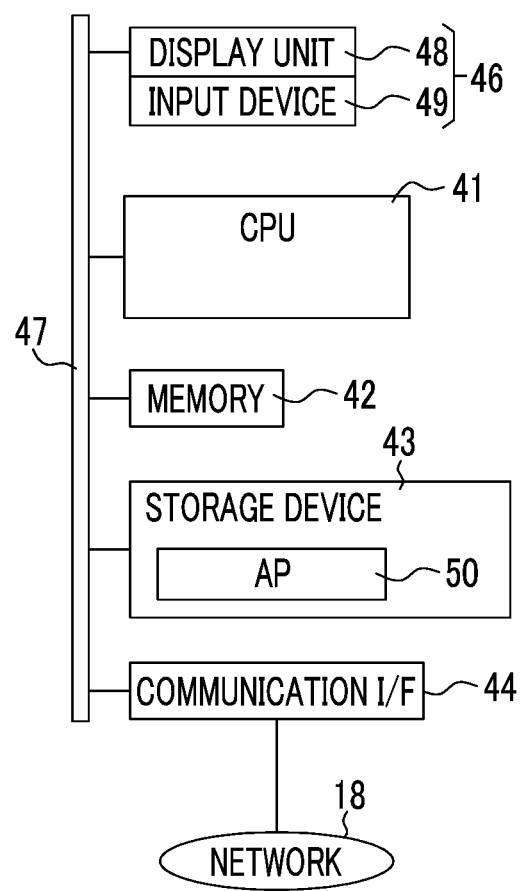
FIG. 8 is a diagram illustrating the structure of a computer forming each DB server or each terminal.

As illustrated in FIG. 8, the computers forming the DB servers 15 to 17 and the terminals 11 and 14 have the same basic structure and each comprise a central processing unit (CPU) 41, a memory 42, a storage device 43, a communication I/F 44, and an input/output unit 46. These components are connected to each other through a data bus 47. The input/output unit 46 includes a display unit 48 and an input device 49 such as a keyboard or a mouse.

The storage device 43 is, for example, a hard disk drive (HDD) and stores a control program or an application program (hereinafter, referred to as an AP) 50. In addition to the HDD storing the programs, a disk array obtained by connecting a plurality of HDDs is provided as the storage device 43 for a DB in a server in which a DB is constructed. The disk array may be provided in the main body of the server, or it may be provided separately from the main body of the server and may be connected to the main body of the server through a cable or a network.

The memory 42 is a work memory that is used by the CPU 41 to perform processes. The CPU 41 loads the control program stored in the storage device 43 to the memory 42 and performs a process according to the program to control the overall operation of each unit of the computer. The communication I/F 44 is a network interface that controls communication with the network 18.

As the AP 50, a client program, such as electronic medical record software for browsing or editing electronic medical records or viewer software for browsing examination images or a similar case list, is installed in the treatment department terminal 11. The viewer software may be, for example, dedicated software or a general-purpose web browser.

Figure 9:
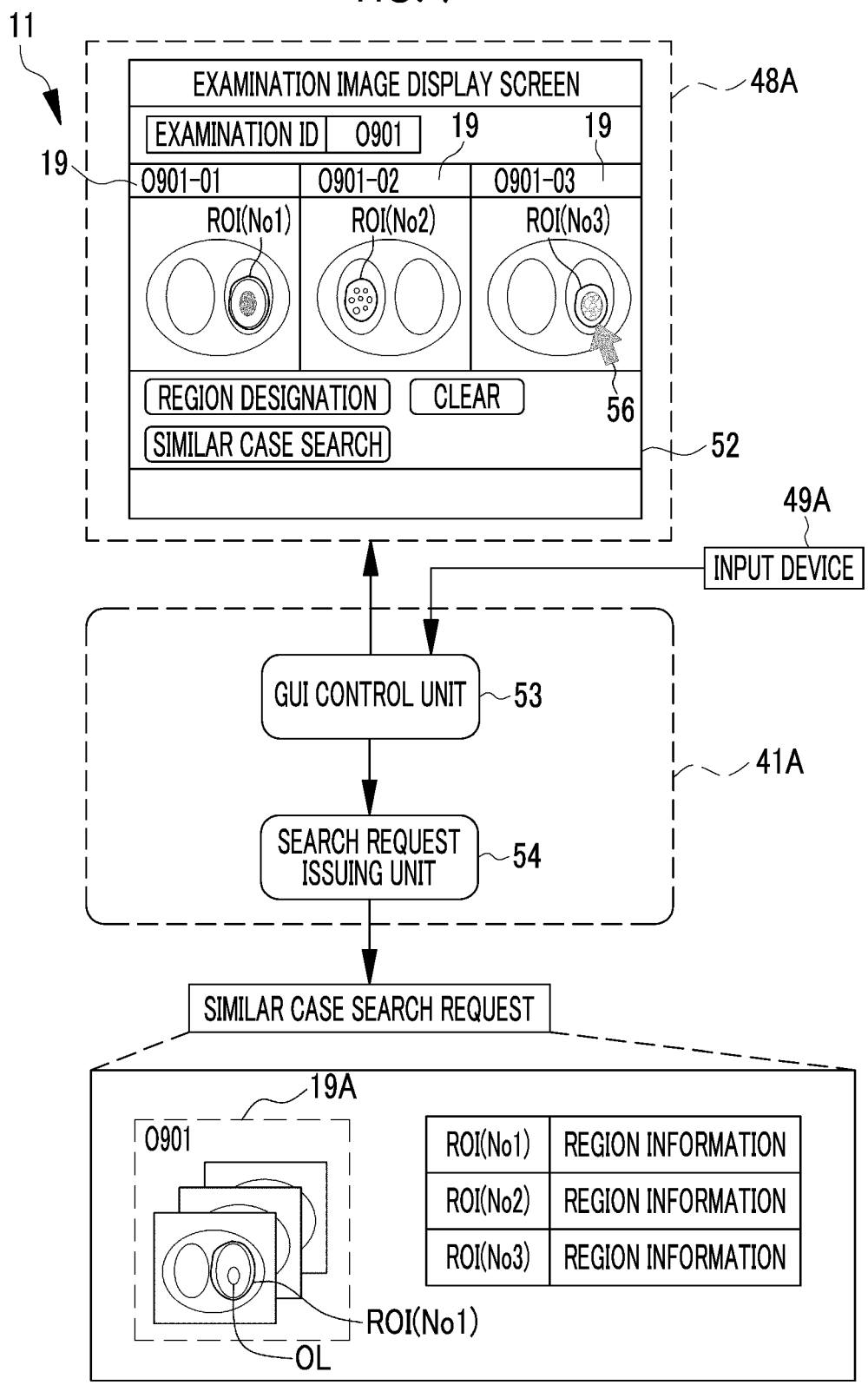
FIG. 9 is a diagram schematically illustrating the structure of a treatment department terminal.

As illustrated in FIG. 9, in the treatment department terminal 11, in the event that viewer software for displaying the examination images 19 starts, an examination image display screen 52 having an operation function by a graphical user interface (GUI) is displayed on a display unit 48A of the treatment department terminal 11. A CPU 41A of the treatment department terminal 11 functions as a GUI control unit 53 and a search request issuing unit 54. An operation of designating the region of interest ROI in the examination image 19 and an operation of instructing the issue of a similar case search request can be performed through the examination image display screen 52. The GUI control unit 53 receives an operation instruction from an input device 49A through the examination image display screen 52 and performs screen control corresponding to the received operation instruction. In the event that an instruction to issue a similar case search request is input, the input issuing instruction is input from the GUI control unit 53 to the search request issuing unit 54. The search request issuing unit 54 adds the designated examination image 19 or the region information of the designated region of interest ROI to the similar case search request and issues the similar case search request.

Figure 10:
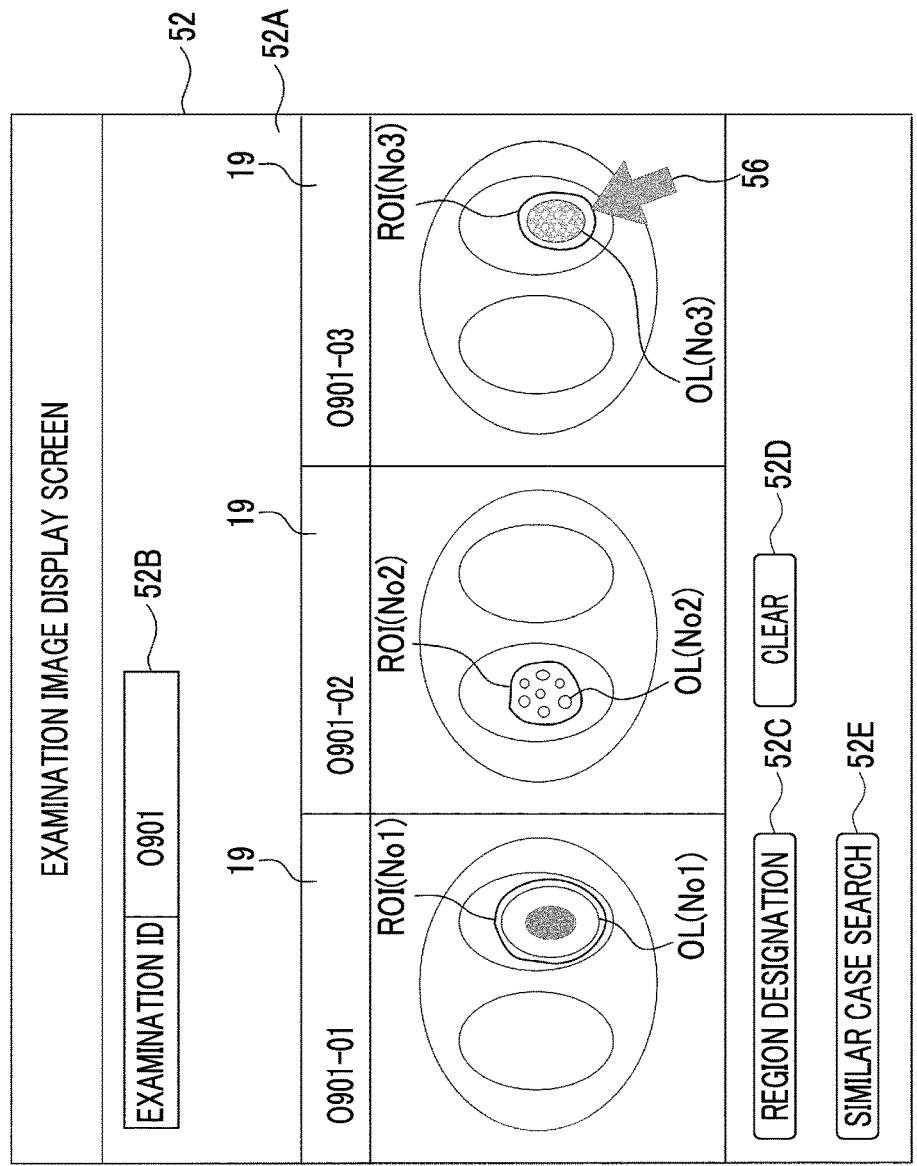
FIG. 10 is a diagram illustrating an examination image display screen for designating a region of interest.

As illustrated in FIG. 10, the examination image display screen 52 includes an image display region 52A in which the examination image 19 is displayed and various operation portions. For example, three examination images 19 are displayed side by side in the image display region 52A. The examination images 19 to be displayed can be switched by a scroll operation or a frame advance operation. An input box 52B for inputting an examination ID is provided in an upper part of the image display region 52A. In the event that an examination ID is input to the input box 52B, examination data 21 with the input examination ID is downloaded from the examination image DB server 15 and the examination image 19 is displayed in the image display region 52A. A region designation button 52C, a clear button 52D, and a similar case search button 52E are provided below the image display region 52A.

The region designation button 52C is an operation button for designating the region of interest ROI in the examination image 19. In the event that the region designation button 52C is clicked by a pointer 56 of a mouse, a region designation operation which designates an arbitrary region of the examination image 19 can be performed. In this state, the pointer 56 is operated to designate the outer circumference of a region including a target lesion OL, using, for example, a spline. The spline is a smooth curve that passes through a plurality of designated control points and is input by the designation of the control points by the pointer 56. The region including the target lesion OL is designated as the region of interest ROI by the above-mentioned operation. The clear button 52D is a button for clearing the designated region of interest ROI.

A plurality of regions of interest ROI can be designated. In the example illustrated in FIG. 10, the regions of interest ROI with No1 to No3 are designated in three examination images 19 with image IDs "O901-01" to "O901-03", respectively. In examination data 21 with an examination ID "901", in the event that no other regions of interest ROI are designated, a total of three regions of interest ROI are designated in one examination data item 21. In the example illustrated in FIG. 11, two regions of interest ROI (No1 and No2) are designated in an examination image 19 with an image ID "O906-01" and the regions of interest ROI (No3 and No4) are designated in examination images 19 with image IDs and "O906-02" and "O906-03", respectively. The region of interest ROI with No3 includes two target lesions OL (No3 and No4). As such, a region including a plurality of target lesions OL may be designated as one region of interest ROI. In examination data 21 with an examination ID "906", in the event that no other regions of interest ROI are designated, a total of four regions of interest ROI are designated in one examination data item 21. Each of the designated regions of interest ROI includes one or more different target lesions OL.

Figure 12:
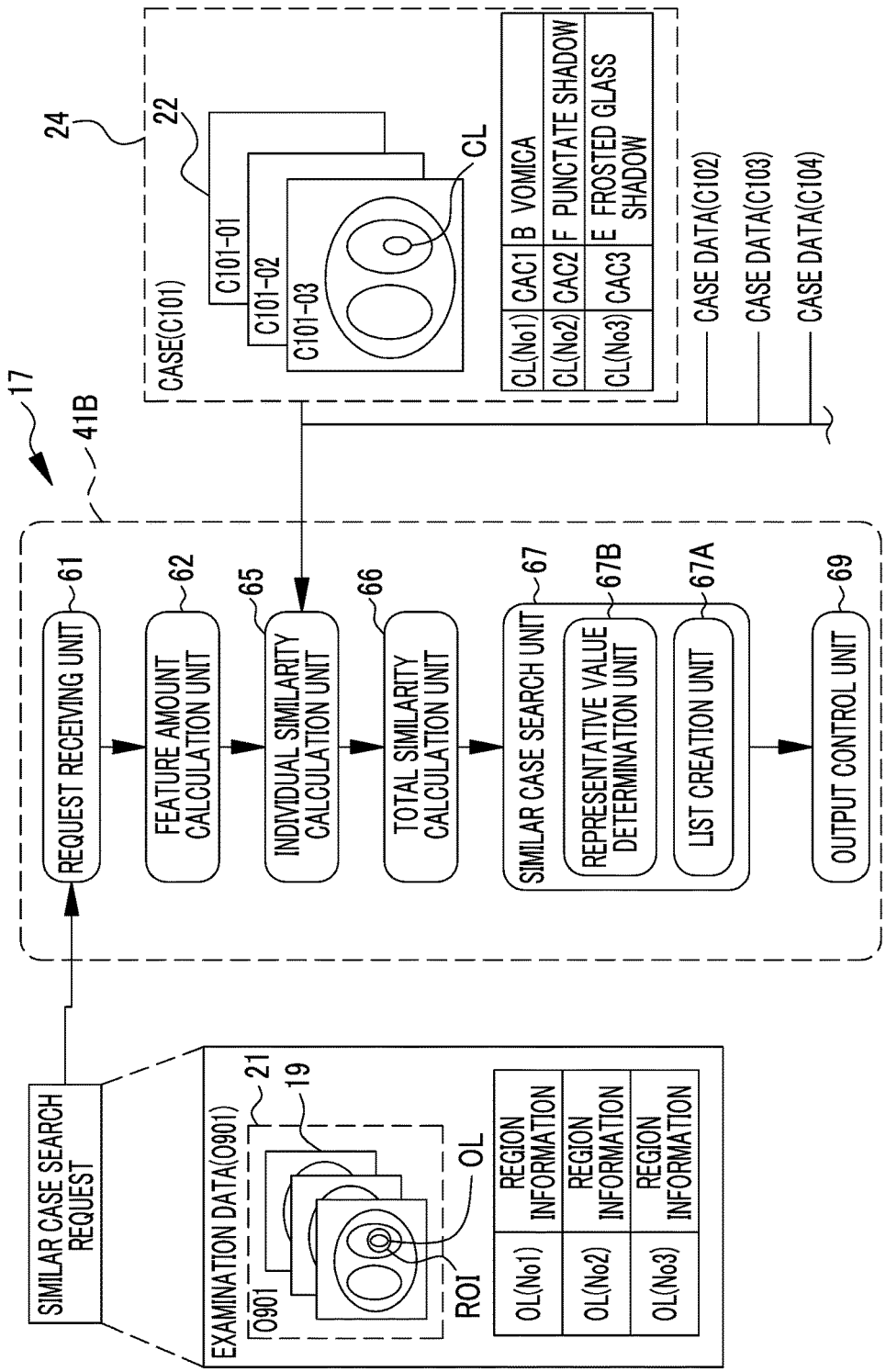
FIG. 12 is a diagram schematically illustrating the structure of the similar case search server.

As illustrated in FIG. 12, a similar case search server program is installed as the AP 50 in the similar case search server 17. In the event that the program is executed, a CPU 41B of the similar case search server 17 functions as a request receiving unit 61, a feature amount calculation unit 62, an individual similarity calculation unit 65, a total similarity calculation unit 66, a similar case search unit 67, and an output control unit 69.

The request receiving unit 61 receives the similar case search request transmitted from the treatment department terminal 11 and stores the received examination image 19 and the received region information of the region of interest ROI in, for example, the storage device 43 of the similar case search server 17. The feature amount calculation unit 62 calculates the feature amount of the region of interest ROI on the basis of the received examination image 19 and region information. Here, the feature amount calculation unit 62 functions as a feature amount acquisition unit.

Figure 13:
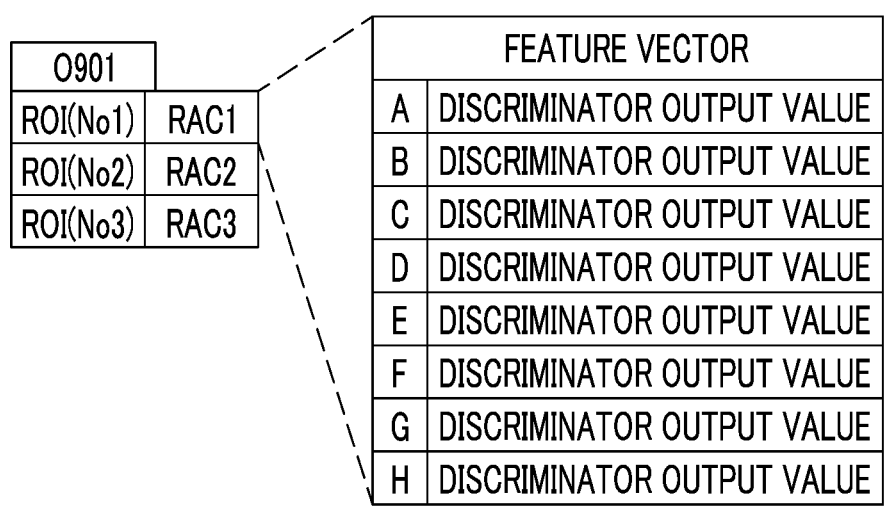
FIG. 13 is a diagram illustrating the feature amount of a region of interest.

As illustrated in FIG. 13, in a case in which there are a plurality of regions of interest ROI, the feature amounts RAC of the regions of interest ROI are calculated for each region of interest ROI. For example, the feature amount of a region of interest ROI with No1 is "RAC1", the feature amount of a region of interest ROI with No2 is "RAC2", and the feature amount of a region of interest ROI with No3 is "RAC3". The feature amount RAC is a feature vector formed by multi-dimensional values (discriminator output values which will be described below) corresponding to a plurality of types of lesion patterns which are set in advance as the image patterns of the typical lesions. The typical lesion patterns are classified into eight types A to H, as described in FIG. 6.

Figure 14:
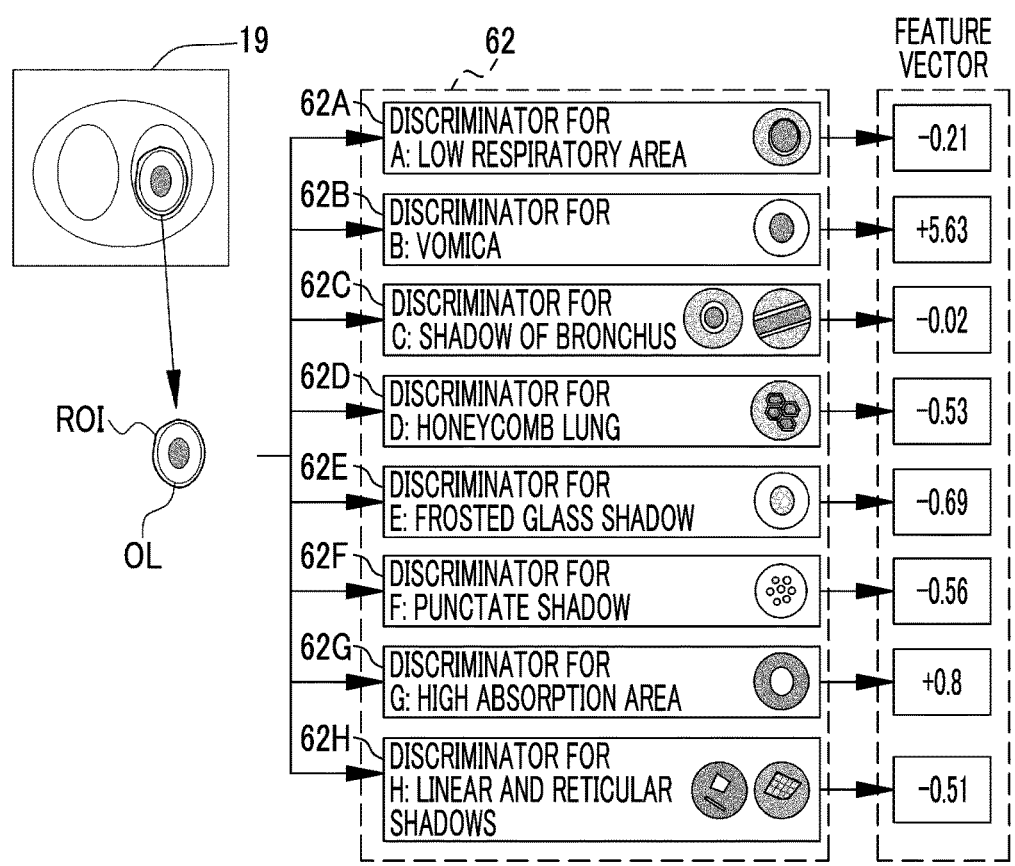
FIG. 14 is a diagram illustrating the structure of a feature amount calculation unit.

As illustrated in FIG. 14, the feature amount calculation unit 62 includes discriminators 62A to 62H corresponding to eight types of typical lesion patterns. Each of the discriminators 62A to 62H outputs values corresponding to each of the typical lesion patterns on the basis of the image pattern of the region of interest ROI. Each of the values output from the discriminators 62A to 62H is multi-dimensional values forming the feature vector. Here, each value is referred to as a discriminator output value. In this example, there are eight types of discriminator output values corresponding to the discriminators 62A to 62H and a feature vector is an eight-dimensional feature vector. As described above, there are eight types of typical lesion patterns A to H. However, the number of types is not limited to 8. The type of discriminator and the number of dimensions of the feature vector are appropriately determined on the basis of the type of lesion pattern.

The discriminator output value indicates the likeness of the typical lesion pattern and indicates the probability of the typical lesion pattern being present in the region of interest ROI. Therefore, as the discriminator output value increases, the probability of the typical lesion pattern being present in the region of interest ROI increases. As the discriminator output value decreases, the probability of the typical lesion pattern being present in the region of interest ROI decreases. Specifically, a "positive (+)" discriminator output value indicates that the typical lesion pattern is present in the region of interest ROI and a "negative (−)" discriminator output value indicates that no typical lesion pattern is present in the region of interest ROI. In the event that the discriminator output value is "positive (+)" and becomes larger, the probability of the typical lesion pattern being present becomes higher.

As can be seen from the example illustrated in FIG. 14, the discriminator 62B corresponding to the lesion pattern "B: vomica" and the discriminator 62G corresponding to the lesion pattern "G: high absorption area" output a "+" value and the output value from the discriminator 62B corresponding to the lesion pattern "B: vomica" is the largest. Therefore, the region of interest ROI includes the lesion pattern "B: vomica" and the lesion pattern "G: high absorption area" and "B: vomica" among the eight types of lesion patterns has a dominant image pattern.

Each of the discriminators corresponding to the typical lesion patterns can be created by a machine learning algorithm, such as "Ada-boost", using, for example, a well-known feature amount described in "Document Name: Computer Vision and Image Understanding, vol. 88, pp. 119 to 151, December 2002, and Chi-Ren Shyu, Christina Pavlopoulou Avinash C. kak, and Cala E. Brodley, "Using Human Perceptual Categories for Content-Based Retrieval from a Medical Image Database".

The feature amount calculation unit 62 calculates the feature amount RAC of each of a plurality of regions of interest ROI designated in the examination data 21 attached to the similar case search request.

Figure 15:
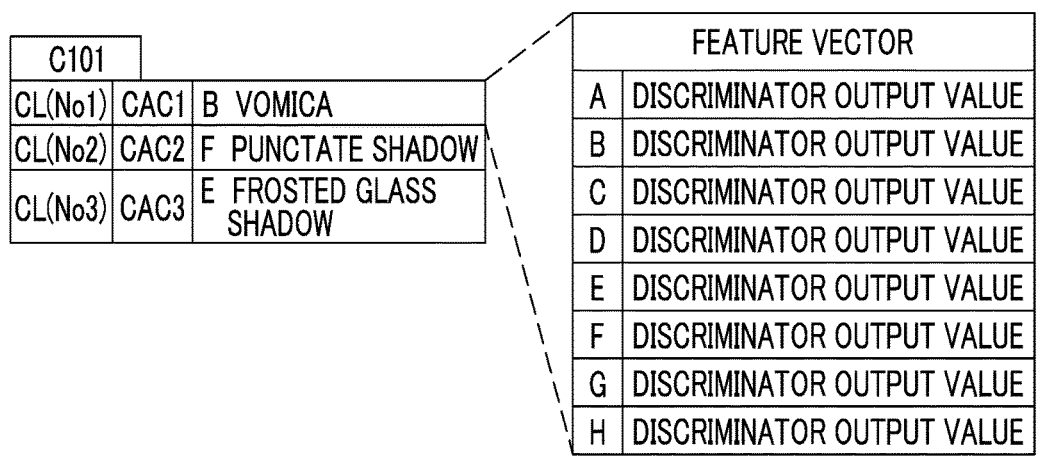
FIG. 15 is a diagram illustrating the feature amount of a case lesion.

As illustrated in FIG. 15, the feature amount CAC of each case lesion CL stored in a feature amount DB 23B of the case DB 23 is formed by a feature vector corresponding to the eight types of lesion patterns. The feature amount CAC is calculated by the same structure as the feature amount calculation unit 62 illustrated in FIG. 14 and is formed by an eight-dimensional feature vector including eight types of output values from the discriminators 62A to 62H. The type of lesion is stored so as to be associated with each case lesion CL.

Figure 16:
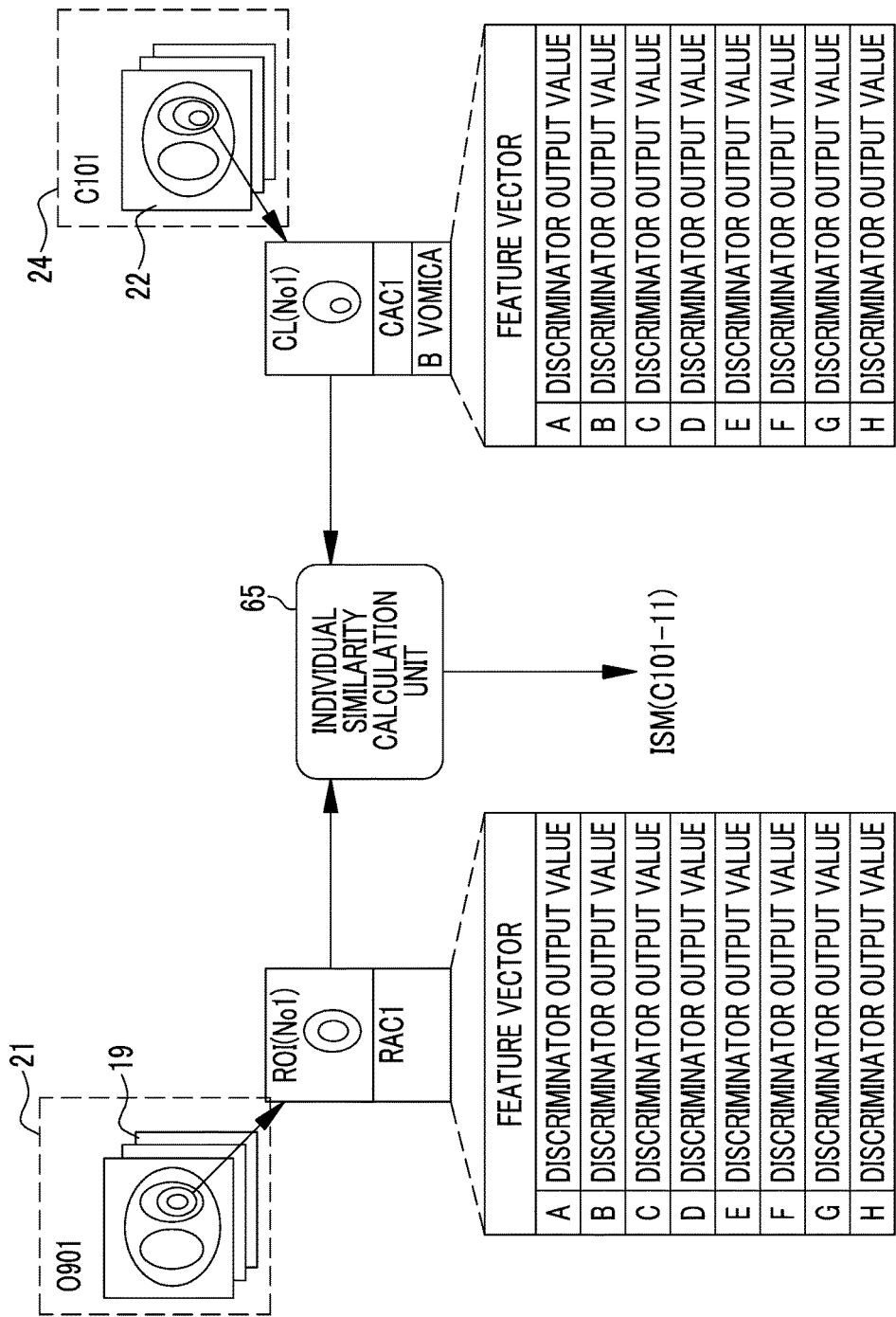
FIG. 16 is a diagram illustrating an individual similarity calculation unit.

As illustrated in FIG. 16, the individual similarity calculation unit 65 compares the feature amount RAC of the region of interest ROI with the feature amount CAC of the case lesion CL and calculates an individual similarity ISM. Specifically, the individual similarity calculation unit 65 compares the eight-dimensional feature vectors included in the feature amount RAC and the feature amount CAC and calculates the individual similarity ISM. The value of the individual similarity ISM is calculated by, for example, a least square distance or correlation. In the former case, as the value decreases, the similarity between the region of interest ROI and the case lesion CL increases. In the latter case, as the value increases, the similarity between the region of interest ROI and the case lesion CL increases.

Figure 17:
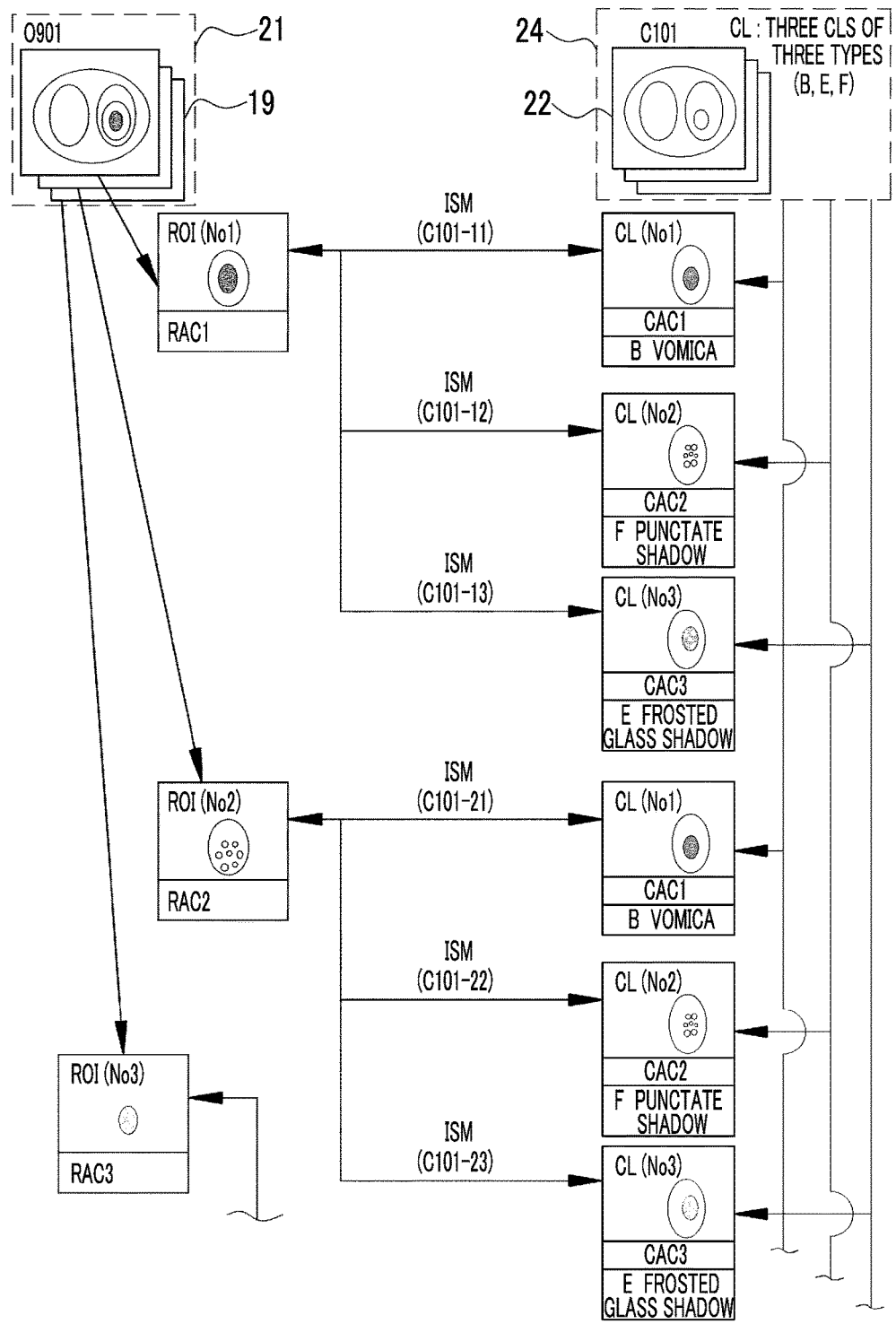
FIG. 17 is a diagram illustrating an individual similarity calculation method.

As illustrated in FIG. 17, the individual similarity calculation unit 65 sets a plurality of regions of interest ROI included in one examination data item 21 and a plurality of case lesions CL included in one case data item 24 so as to be in one-to-one correspondence with each other, compares each feature amount RAC with each feature amount CAC, and calculates the individual similarities ISM. Since the individual similarity ISM is similarity for each region of interest ROI, it is individual similarity for each region of interest. Since the individual similarity ISM is calculated in one-to-one correspondence with the case lesion CL, it is also individual similarity for each case lesion CL. The individual similarity calculation unit 65 calculates the individual similarities ISM corresponding to the number of case lesions CL for one region of interest ROI. Since the individual similarity ISM is calculated for all of the regions of interest ROI, the individual similarity calculation unit 65 calculates the individual similarities ISM corresponding to a value obtained by multiplying the number of regions of interest ROI by the number of case lesions CL.

In the examination data 21 with the examination ID "O901", three regions of interest ROI with No1 to No3 are designated. Three case lesions CL with No1 to No3 are registered in the case data 24 with the case ID "C101". In the case with the case ID "C101", three types of case lesions CL with No1 to No3 are "B: vomica", "F: a punctate shadow (small nodules)", and "E: a frosted glass shadow (ground glass opacity)" and are different from each other. Therefore, three case lesions CL of three types are registered.

Figure 18:
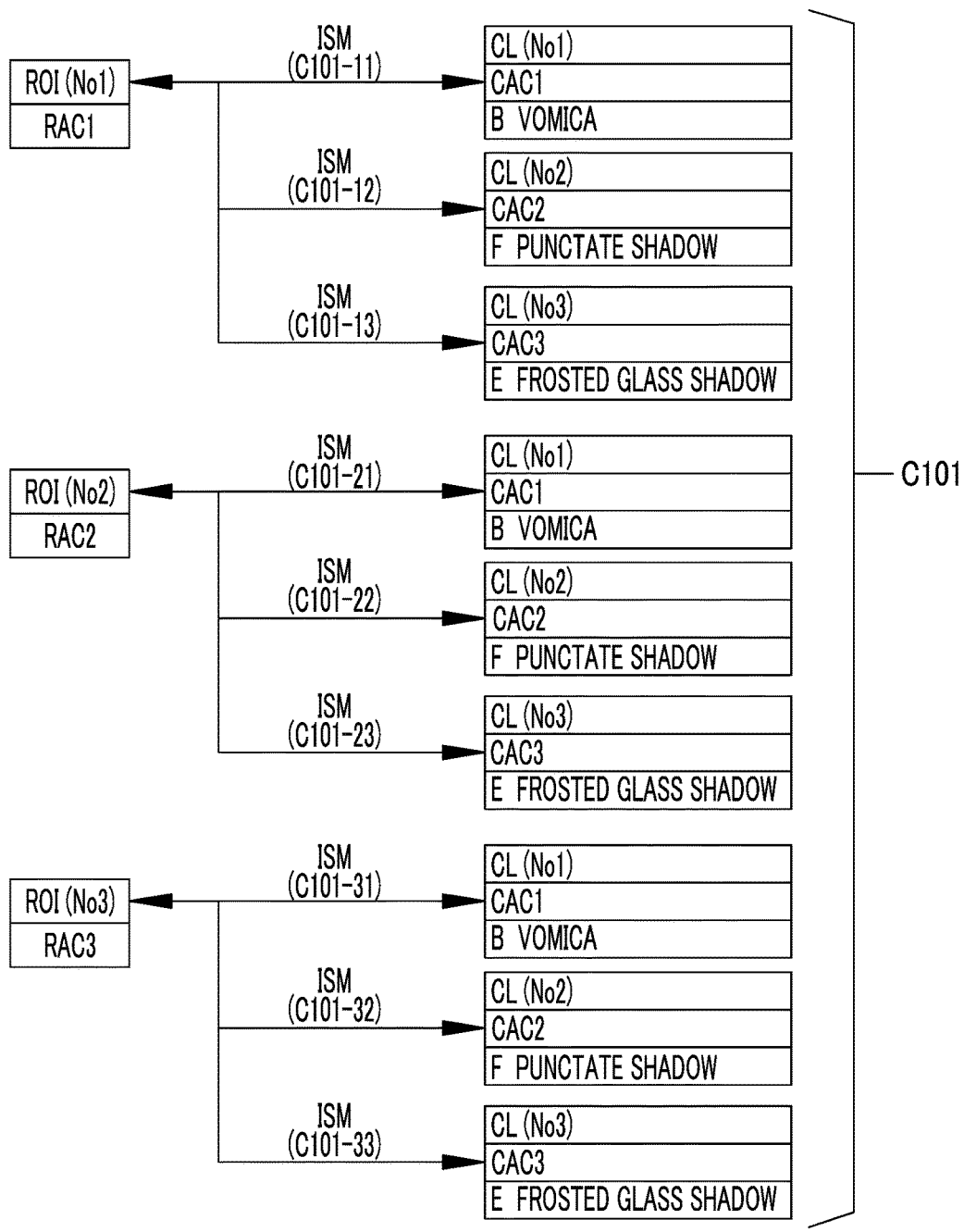
FIG. 18 is a diagram illustrating individual similarities in a case in which there are three case lesions of three types.

In this example, unlike the total similarity calculation unit 66 which will be described below, the individual similarity calculation unit 65 calculates the individual similarity ISM on the basis of only the number of case lesions CL, without considering the type of case lesion CL. Therefore, as illustrated in FIG. 18, a total of nine (=3×3) individual similarities ISM are calculated between the examination data 21 with the examination ID "O901" and the case data 24 with the case ID "C101".

An identification code in parentheses which follow each individual similarity ISM is obtained by adding the serial number of each of the region of interest ROI and the case lesion CL to the case ID. For example, "C101-11" indicates an individual similarity ISM between the region of interest ROI with No1 and the case lesion CL with No1 which is registered in the case data 24 with the case ID "C101". Similarly, "C101-12" indicates an individual similarity ISM between the region of interest ROI with No1 and the case lesion CL with No2 which is registered in the case data 24 with the case ID "C101".

Figure 19:
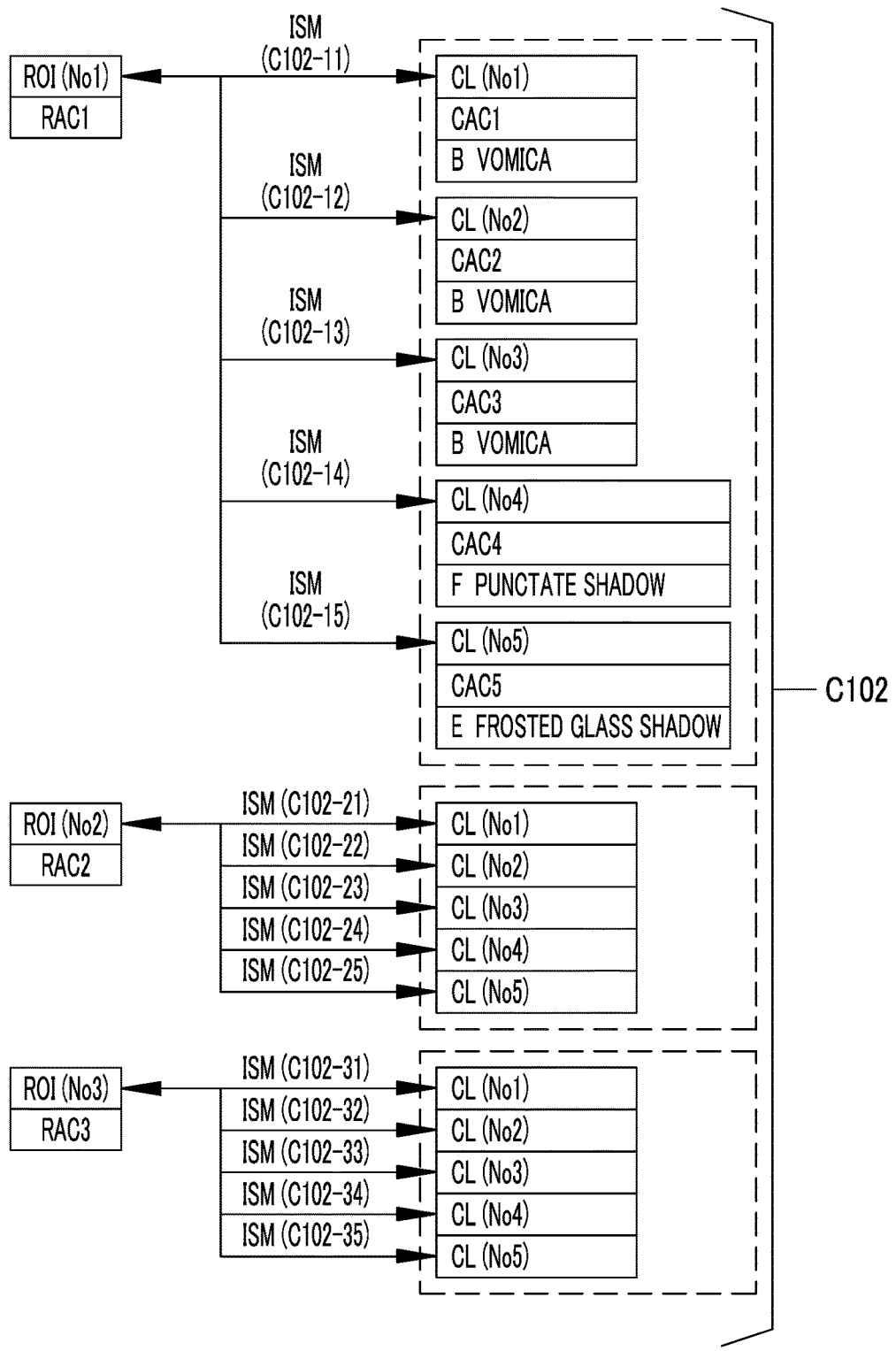
FIG. 19 is a diagram illustrating individual similarities in a case in which there are five case lesions of three types.

Five case lesions CL with No1 to No5 are registered in the case with the case ID "C102" illustrated in FIG. 19. In the case with the case ID "C102", five case lesions CL with No1 to No5 are three types, that is, "B: vomica", "F: a punctate shadow", and "E: a frosted glass shadow". For "B: vomica", three case lesions CL (No1 to No3) of the same type are registered. In addition, "F: a punctate shadow" and "E: a frosted glass shadow" are registered as the types of the case lesions CL with No4 and No5, respectively. That is, five case lesions CL of three types are registered in the case with the case ID "C102".

The individual similarity calculation unit 65 sets five case lesions CL in the case with the case ID "C102" so as to corresponding to each of three regions of interest ROI, regardless of the type of case lesion. Therefore, the individual similarity calculation unit 65 calculates a total of 15 (=3×5) individual similarities ISM.

Figure 20:
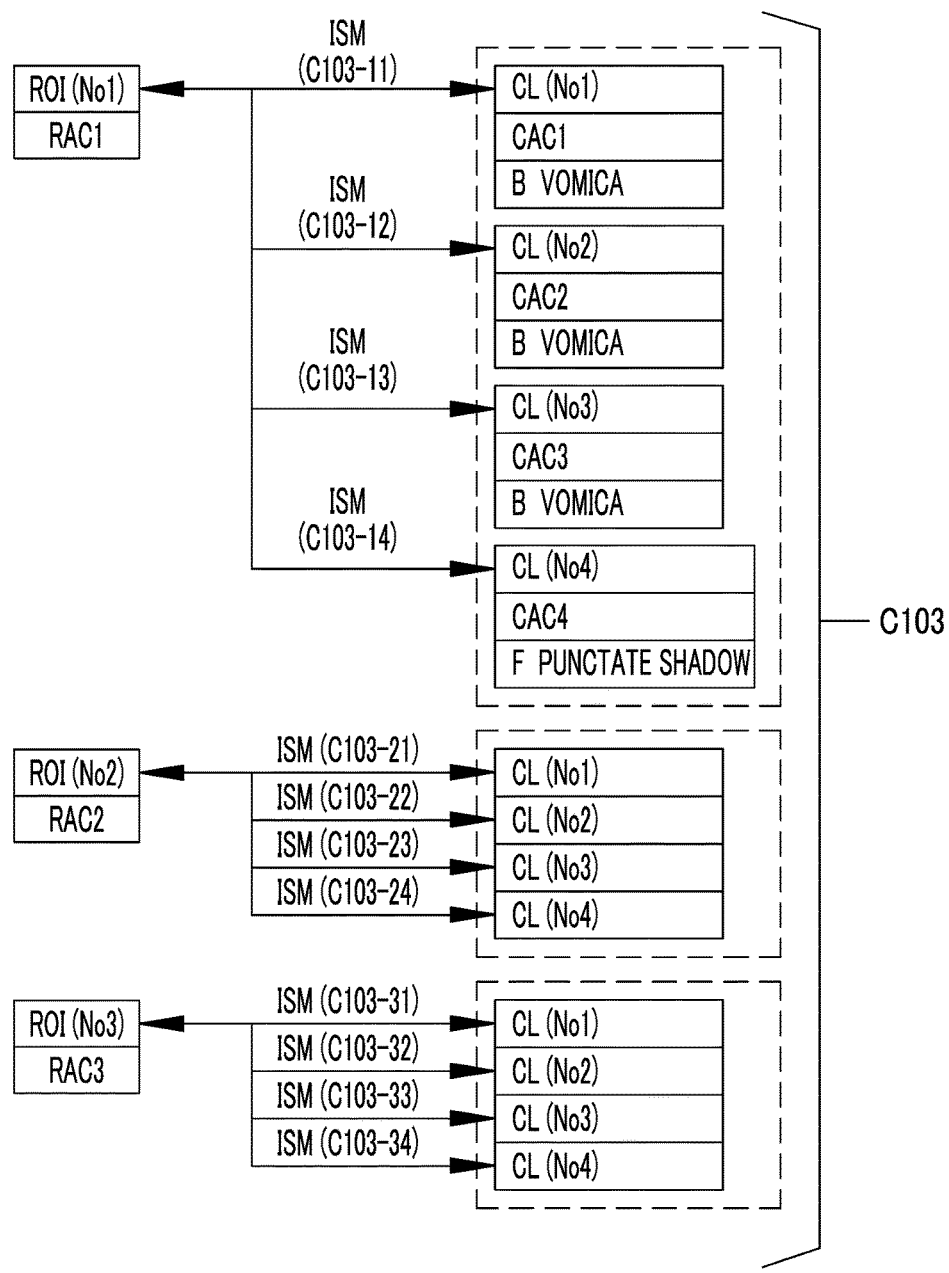
FIG. 20 is a diagram illustrating individual similarities in a case in which there are four case lesions of two types.

The case with the case ID "C103" illustrated in FIG. 20 is an example in which four case lesions CL of two types are registered. In the case with the case ID "C103", the number of types of four case lesions CL with No1 to No4 are two, that is, "B: vomica" and "F: a punctate shadow", three case lesions CL (No1 to No3) are the same type "B: vomica", and one case lesion CL (No4) is the type "F: a punctate shadow". The individual similarity calculation unit 65 sets four case lesions CL in the case with the case ID "C103" so as to correspond to each of three regions of interest ROI, regardless of the type of case lesion, and calculates a total of 12 (=3×4) individual similarities ISM.

Figure 21:
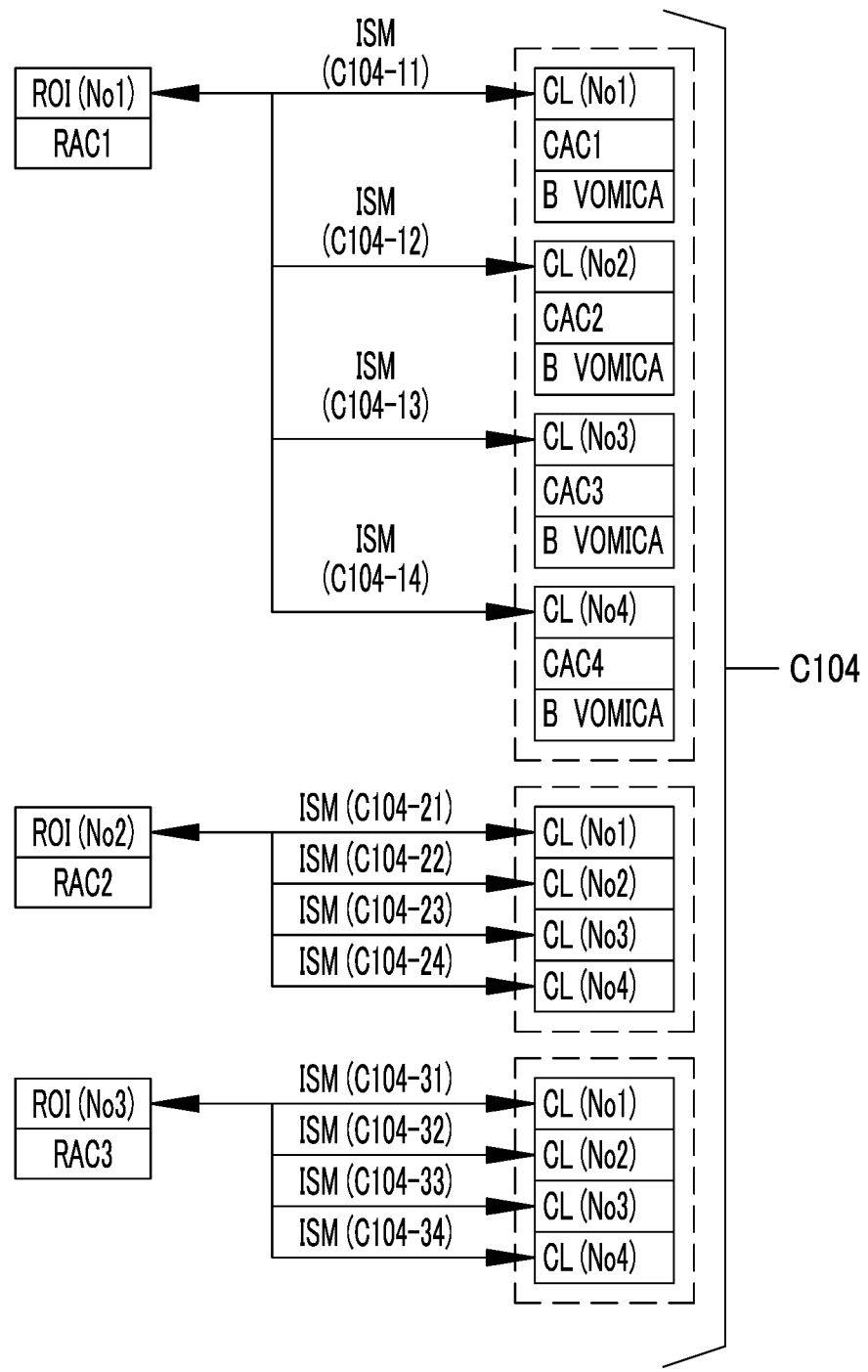
FIG. 21 is a diagram illustrating individual similarities in a case in which there are four case lesions of the same type.

A case with a case ID "C104" illustrated in FIG. 21 is an example in which four case lesions CL of the same type are registered. All of four case lesions CL with No1 to No4 in the case with the case ID "C104" are the same type "B: vomica". The individual similarity calculation unit 65 sets four case lesions CL in the case with the case ID "C103" so as to correspond to each of three regions of interest ROI, regardless of the type of case lesion, and calculates a total of 12 (=3×4) individual similarities ISM.

Figure 22:
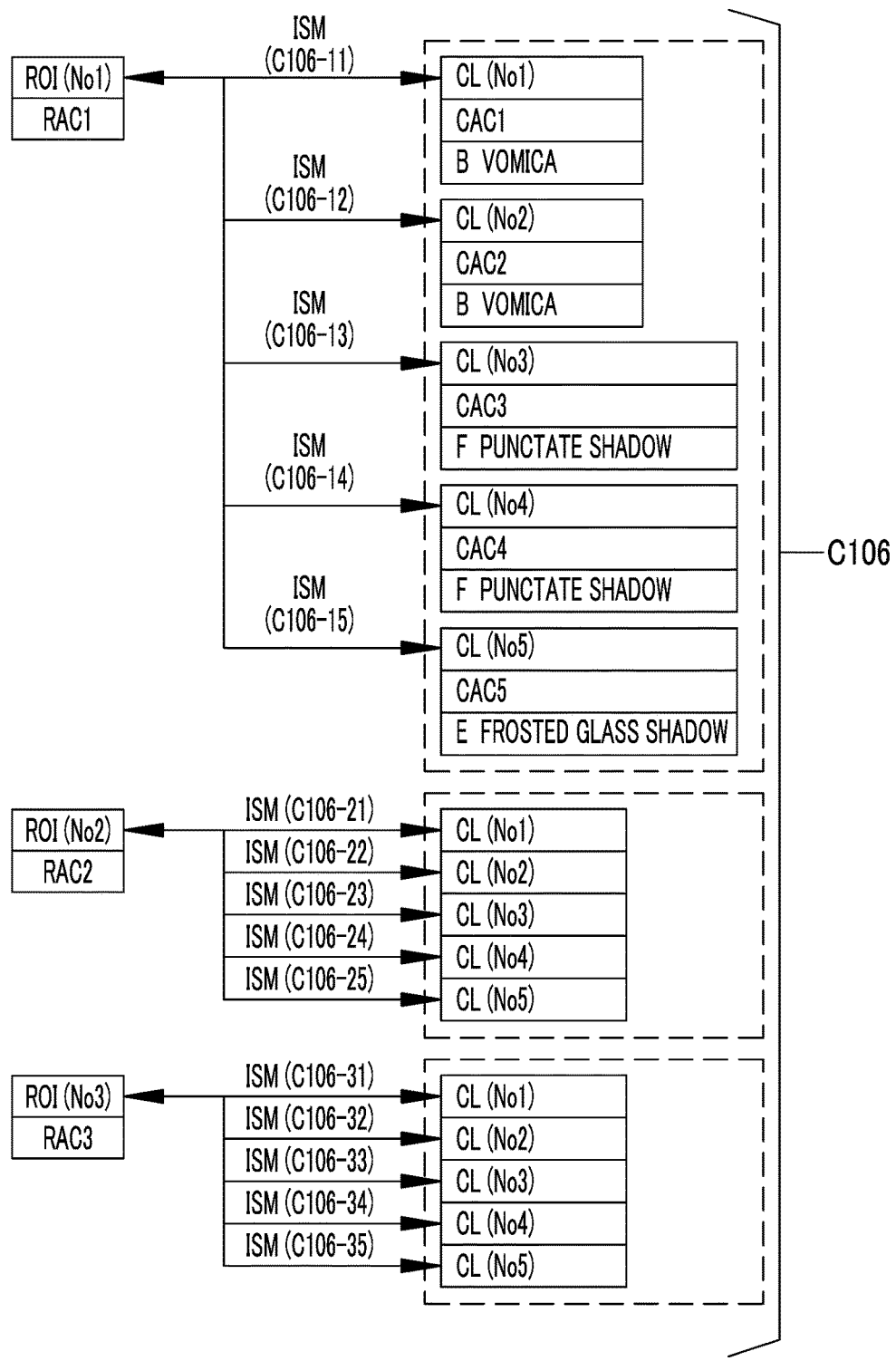
FIG. 22 is a diagram illustrating individual similarities in a case in which there are five case lesions of three types.

A case with a case ID "C106" illustrated in FIG. 22 is the same example as the case with the case ID "C101" illustrated in FIG. 19 in which five case lesions CL of three types are registered, but is different from the case with the case ID "C101" in breakdown. That is, the case with the case ID "C106" is the same as the case with the case ID "C101" in that five case lesions CL with No1 to No5 in the case with the case ID "C106" are three types, that is, "B: vomica", "F: a punctate shadow", and "E: a frosted glass shadow". However, in the case with the case ID "C106", two case lesions CL (No1 and No2) of the same type "B: vomica" are registered and two case lesions CL (No3 and No4) of the same type "F: a punctate shadow" are registered. One case lesion CL (No5) of the type "E: a frosted glass shadow" is registered. The individual similarity calculation unit 65 sets five case lesions CL in the case with the case ID "C106" so as to correspond to each of three regions of interest ROI, regardless of the type of case lesion, and calculates a total of 15 (=3×5) individual similarities ISM.

Figure 23:
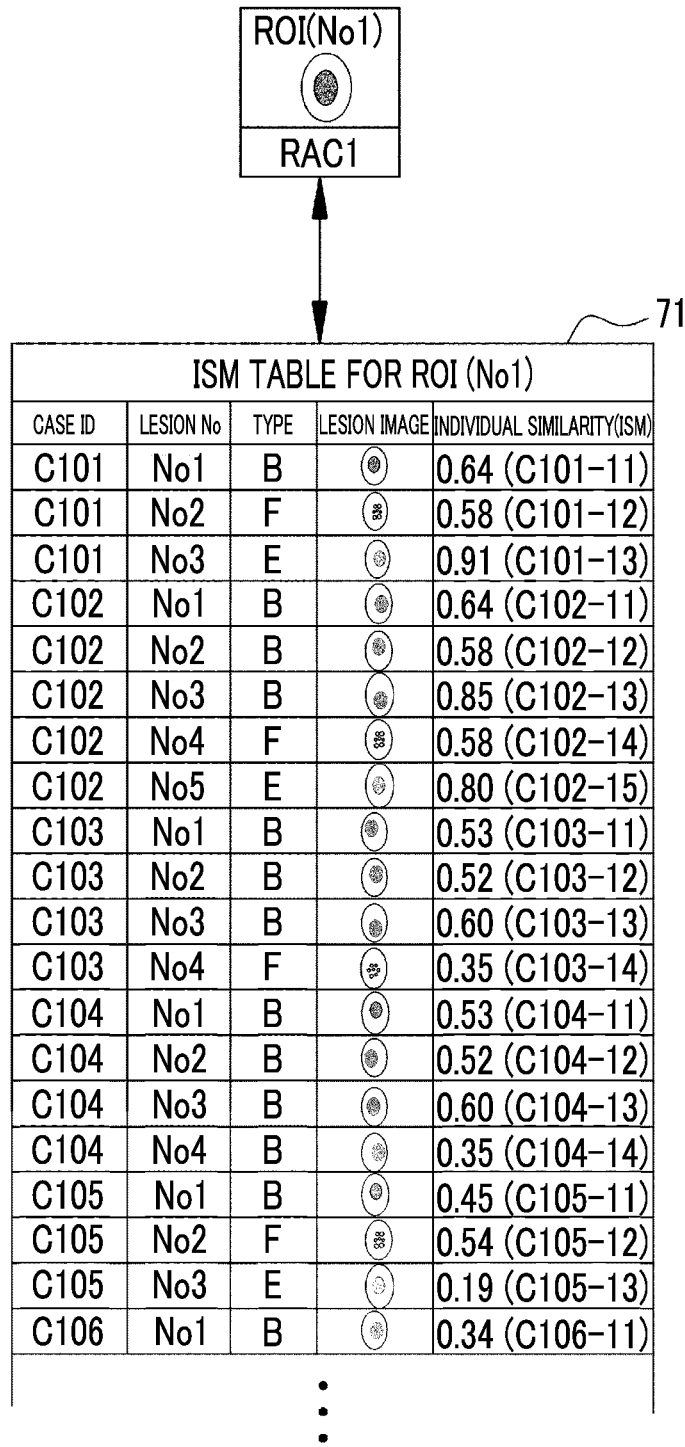
FIG. 23 is a diagram illustrating an individual similarity table.

As illustrated in FIG. 23, for example, the individual similarity calculation unit 65 creates an individual similarity table (hereinafter, referred to as an ISM table) 71 in the memory 42B or the storage device 43B of the similar case search server 17 and registers the calculated individual similarities ISM in the ISM table 71. The ISM table 71 is created for each region of interest ROI. In the example illustrated in FIG. 23, the ISM table 71 for the region of interest ROI with No1 is illustrated. The ISM table 71 is a table in which a case ID, a lesion number, the type of lesion, and a lesion image are stored so as to be associated with each individual similarity ISM. The lesion image is image data of the case lesion CL. That is, in the ISM table 71, one record includes five data items, that is, the case ID, the lesion number, the type of lesion, the lesion image, and the individual similarity ISM.

First, the individual similarity calculation unit 65 records each individual similarity ISM in the ISM table 71 in a calculation order. The individual similarities ISM are recorded in ascending order of the number of the case ID, such as in the order of "C101", "C102", and "C103". The value of the individual similarity ISM is calculated by the correlation between the feature amount RAC of the region of interest ROI and the feature amount CAC of the case lesion CL. Therefore, as the value increases, the similarity increases.

Figure 24:
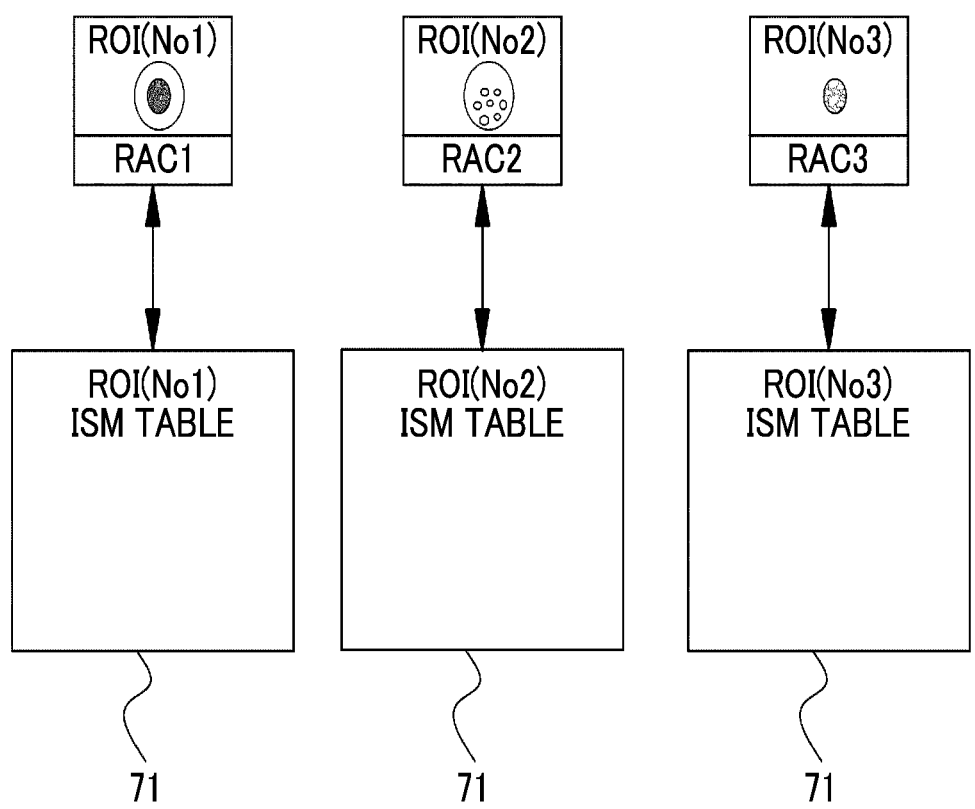
FIG. 24 is a diagram illustrating an individual similarity table created for each region of interest.

As illustrated in FIG. 24, the individual similarity calculation unit 65 creates the ISM table 71 for each region of interest ROI. In a case in which there are three regions of interest ROI with No1 to No3, three ISM tables 71 are created. In this stage, as illustrated in FIG. 23, in the ISM tables 71, each record is arranged in the order of the number of the case ID. In a case in which the creation of the ISM tables 71 ends, the individual similarity calculation unit 65 transmits the ISM tables 71 to the total similarity calculation unit 66.

Figure 25:
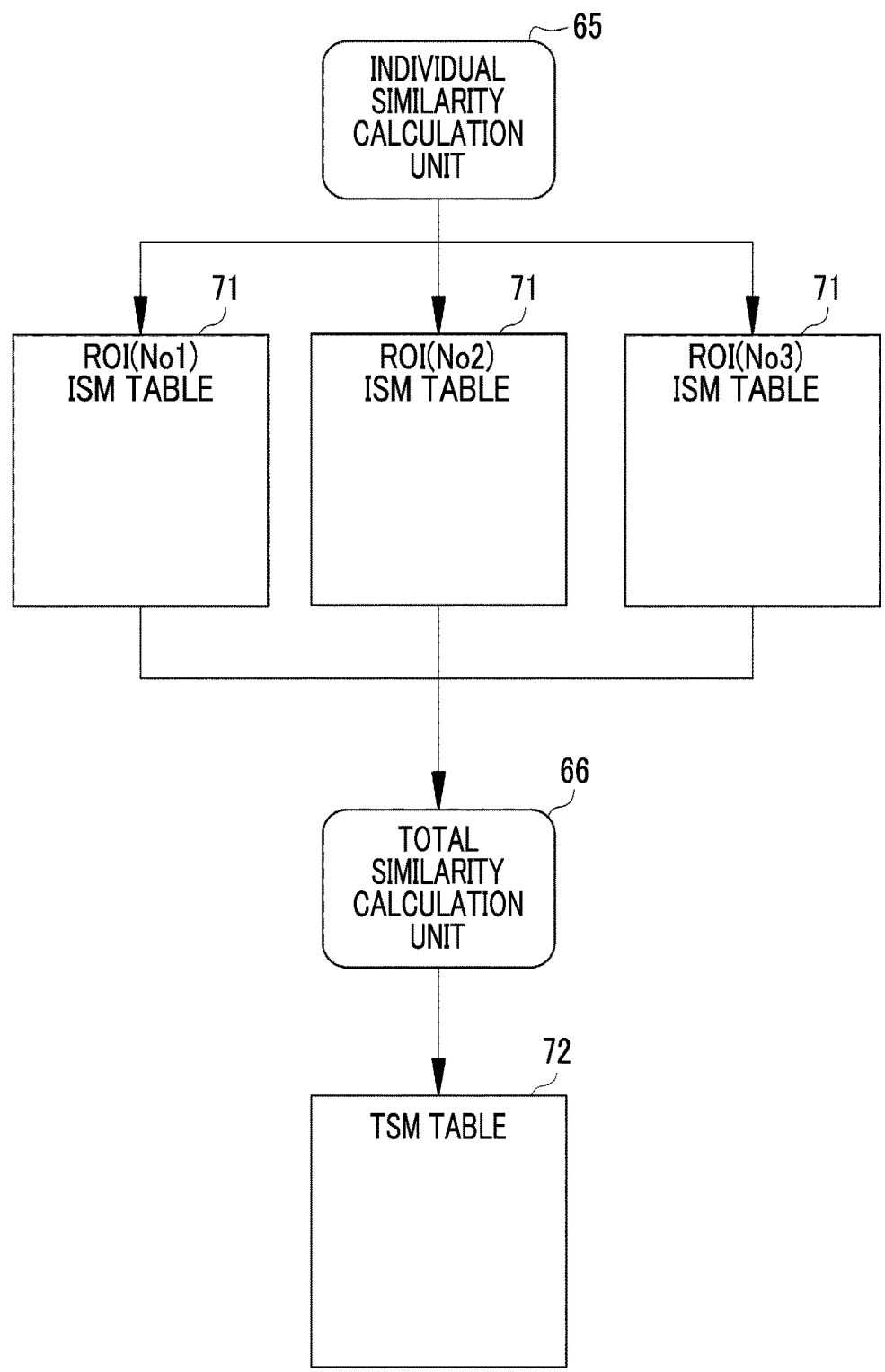
FIG. 25 is a diagram illustrating a total similarity table.
Figure 26:
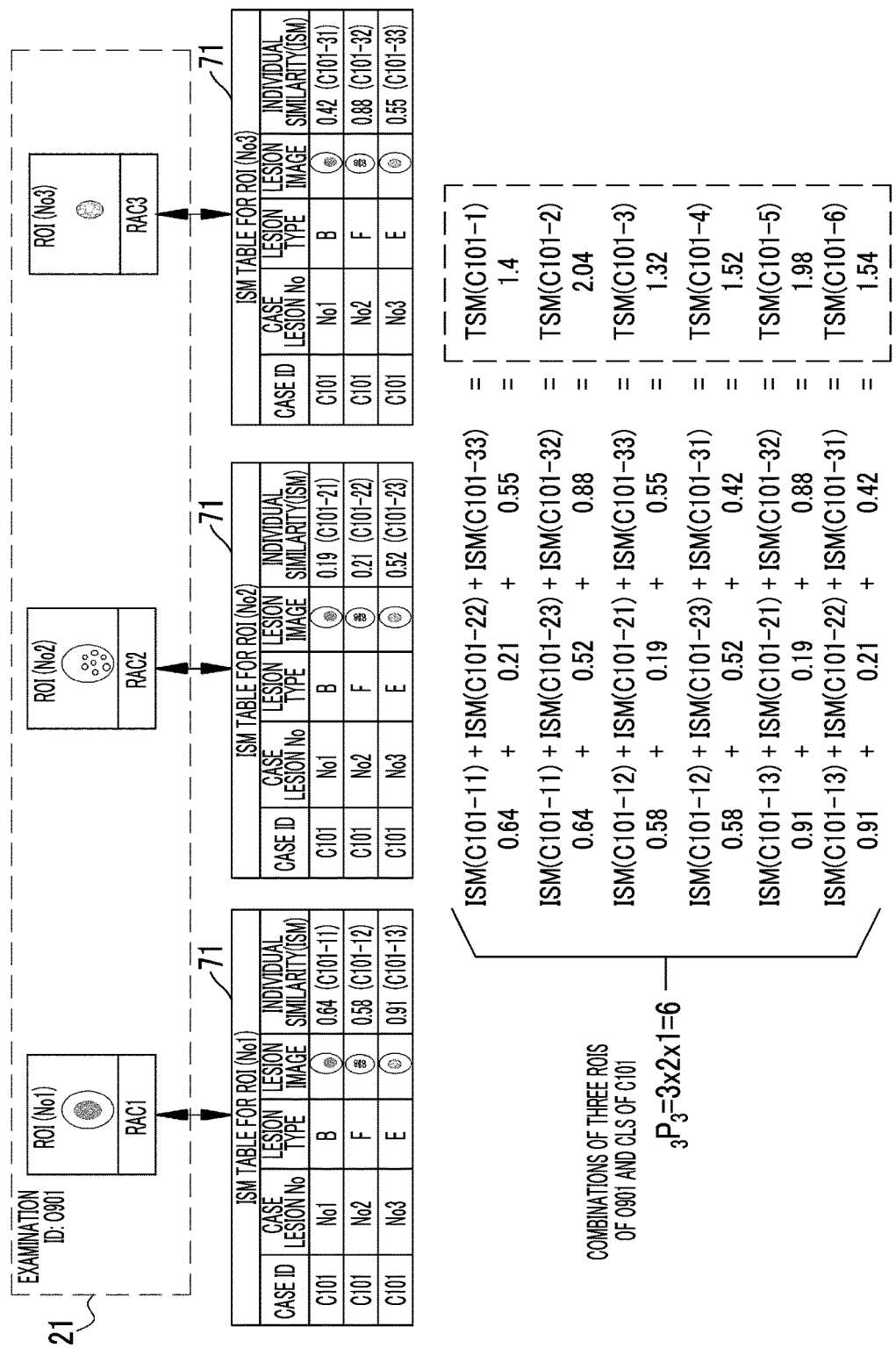
FIG. 26 is a diagram illustrating a total similarity calculation method.

As illustrated in FIG. 25, the total similarity calculation unit 66 creates a total similarity TSM table 72 (hereinafter, referred to as a TSM table 72) on the basis of a plurality of ISM tables 71 created for each region of interest ROI. Specifically, as illustrated in FIG. 26, the total similarity calculation unit 66 reads out the individual similarities ISM, which have been calculated by the correspondence with the case lesions CL in the same case, one by one from the plurality of ISM tables 71 and calculates a total similarity TSM on the basis of a plurality of individual similarities ISM read from each ISM table 71. Specifically, the total similarity calculation unit 66 creates combinations of the individual similarities ISM corresponding to the number of regions of interest ROI and the number of case lesions CL, using each individual similarity ISM read from each ISM table 71 as an element of the total similarity TSM, and calculates the total similarity for each combination.

The individual similarities ISM are calculated by a one-to-one correspondence between a plurality of regions of interest ROI and a plurality of case lesions CL and the values of the individual similarities ISM vary depending on the correspondence relationship between each region of interest ROI and each case lesion CL. Therefore, the total similarity TSM varies depending on the combination pattern of the individual similarities ISM.

A method for creating the combination pattern of the individual similarities ISM will be described below. In this example, in a case in which three regions of interest ROI with No1 to No3 correspond to three case lesions CL of three types in the case with the case ID "C101", nine (=3×3) individual similarities ISM are calculated. Among the nine individual similarities ISM, three individual similarities ISM are recorded in each ISM table 71 for each region of interest ROI. Then, the total similarity calculation unit 66 reads out the nine individual similarities ISM for the case with the case ID "C101" one by one from the ISM tables 71, creates six combination patterns of the individual similarities ISM, and calculates six total similarities TSM corresponding to six combinations "C101-1" to "C101-6". Identification codes for each total similarity TSM are obtained by adding serial numbers 1 to 6 of the total similarities TSM to the case ID. In this example, each total similarity TSM is the sum of three individual similarities ISM.

Each individual similarity ISM is obtained in a case in which the regions of interest ROI correspond one to one with the case lesions CL. Therefore, as the total similarity TSM increases, the average value of the individual similarities ISM between three regions of interest ROI and three case lesions CL increases. In this example, the individual similarity ISM is represented by a correlation value. Therefore, as the value increases, the similarity increases. As a result, as the value increases, the total similarity TSM increases.

In this example, among six total similarities TSM, the total similarity TSM with the identification code "C101-2" has the highest value of "2.04". In contrast, in this example, the total similarity TSM with the identification code "C101-3" has the lowest value of "1.32". The total similarity TSM with the identification code "C101-5" includes the individual similarity ISM (C101-13) having the highest value of "0.91" among the individual similarities ISM. However, the total similarity TSM with the identification code "C101-2" without including the individual similarity ISM with the highest value is higher than the other total similarities TSM since the average value of the individual similarities ISM is high.

Among six total similarities TSM, the total similarity TSM (C101-2) with the highest value is the sum of the individual similarity ISM (C101-11) between the region of interest ROI with No1 and the case lesion CL with No1, the individual similarity ISM (C101-23) between the region of interest ROI with No2 and the case lesion CL with No3, and the individual similarity ISM (C101-32) between the region of interest ROI with No3 and the case lesion CL with No2. Therefore, it can be evaluated that the similarity between the examination data 21 with the examination ID "O901" and the case with the case ID "C101" is the highest in a case in which the case lesions CL with No1 to No3 correspond to the regions of interest ROI with No1, No3, and No2.

The total similarity calculation unit 66 creates combinations of completely different types of individual similarities ISM for calculating the total similarity TSM. Here, the combinations of completely different types mean all of combinations in a case in which different types of case lesions CL are extracted one by one from a plurality of case lesions CL in the same case and combinations of different types of case lesions CL correspond to each region of interest ROI. Then, the total similarity calculation unit 66 determines that the combinations of completely different types are used to calculate the total similarity TSM and combinations other than the combinations of completely different types are not used to calculate the total similarity TSM. That is, the total similarity calculation unit 66 calculates the total similarity TSM, using only the combinations of completely different types of individual similarities ISM.

The combinations other than the combinations of completely different types include combinations of the individual similarities ISM of the same type and combinations of the individual similarities ISM, some of which are the same type. The combinations of the individual similarities ISM of the same type are all of combinations in a case in which a plurality of case lesions CL of the same type are extracted one by one from a plurality of case lesions CL in the same case and combinations of the extracted case lesions CL of the same type correspond to each region of interest ROI. The combinations of the individual similarities ISM, some of which are the same type, mean all of combinations in a case in which a plurality of case lesions CL of the same type and one or more case lesions CL of different types are extracted one by one from a case including at least two or more case lesions CL of the same type and one or more case lesions CL of different types and combinations of the extracted case lesions CL of the same type and the extracted case lesions CL of different types correspond to each region of interest ROI. The total similarity calculation unit 66 creates combinations of completely different types which correspond to the number of regions of interest ROI and the number of case lesions CL in one case, on the basis of the individual similarities ISM which have been read one by one from each ISM table 71.

Figure 27:
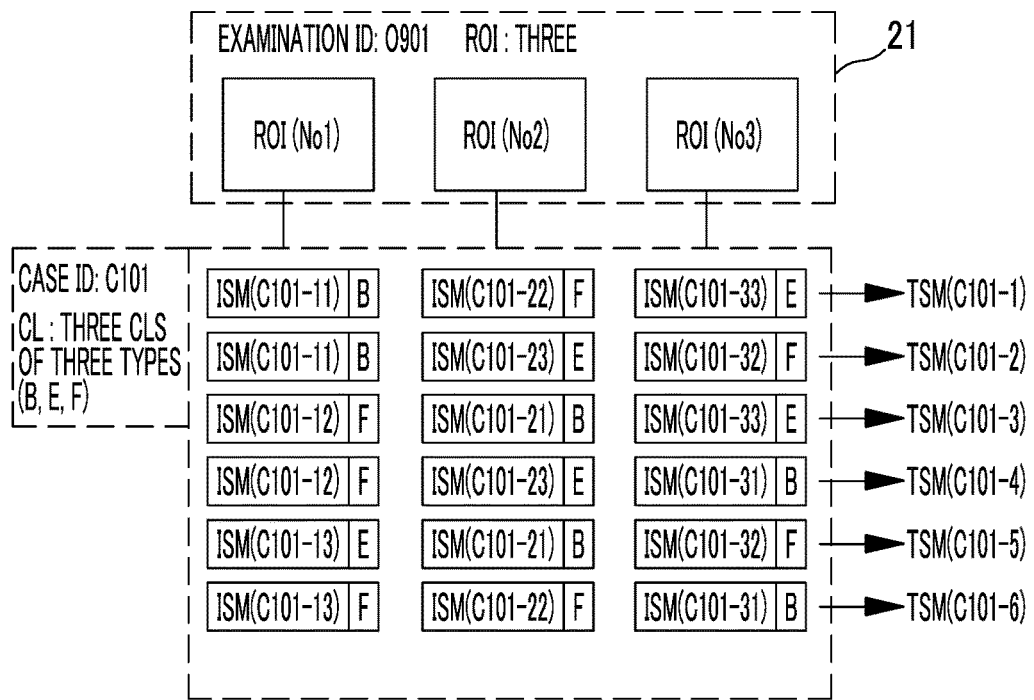
FIG. 27 is a diagram illustrating combinations of completely different types in the example illustrated in FIG. 19.

Combinations of completely different types of individual similarities ISM will be described in detail with reference to FIGS. 27 to 34. In FIG. 27, letters "B", "E", and "F" attached to each individual similarity ISM indicate the types of case lesions CL corresponding to each individual similarity ISM and indicate which type of case lesion CL corresponds to the region of interest ROI in order to calculate each individual similarity ISM.

In the case with the case ID "C101", three case lesions CL with No1 to No3 are "B (vomica)", "F (punctate shadow)", and "E (frosted glass shadow)" which are different types. Therefore, the number of patterns of combinations of completely different types of individual similarities ISM which are calculated by the correspondence between three case lesions CL of three types "B, E, and F" and three regions of interest ROI, such as "B, F, E", "B, E, F", "F, B, E", "F, E, B", . . . , is equal to the number of permutations of three regions of interest ROI and three case lesions CL. That is, $_3P_3 = 3 \times 2 \times 1 = 6$ is established.

Figure 28:
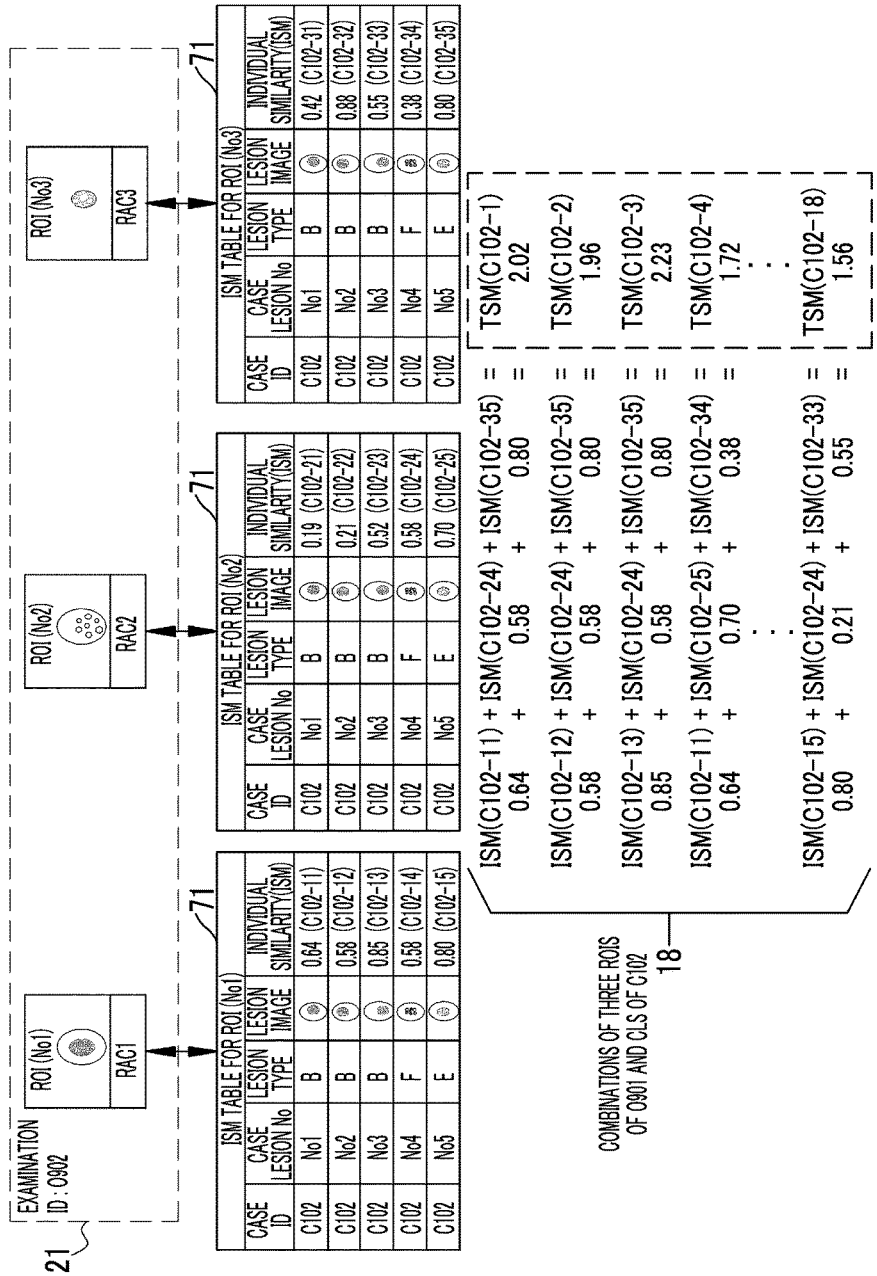
FIG. 28 is a diagram illustrating total similarities corresponding to the combinations of completely different types illustrated in FIG. 27.

In a case in which there are five case lesions CL of three types, that is, three case lesions CL of the type "B", one case lesion CL of the type "E", and one case lesion CL of the type "F" as in the case with the case ID "C102" illustrated in FIG. 19, five individual similarities ISM are recorded in each ISM table 71 corresponding to each of the regions of interest ROI with No1 to No3, that is, a total of 15 individual similarities ISM are recorded in the ISM tables 71, as illustrated in FIG. 28. In a case in which there are a plurality of case lesions CL of the same type as in the case with the case ID "C102", the total similarity calculation unit 66 distinguishes three case lesions CL (B1 to B3) of the same type and creates combinations of completely different types for each of the distinguished case lesions CL of the same type.

Figure 29:
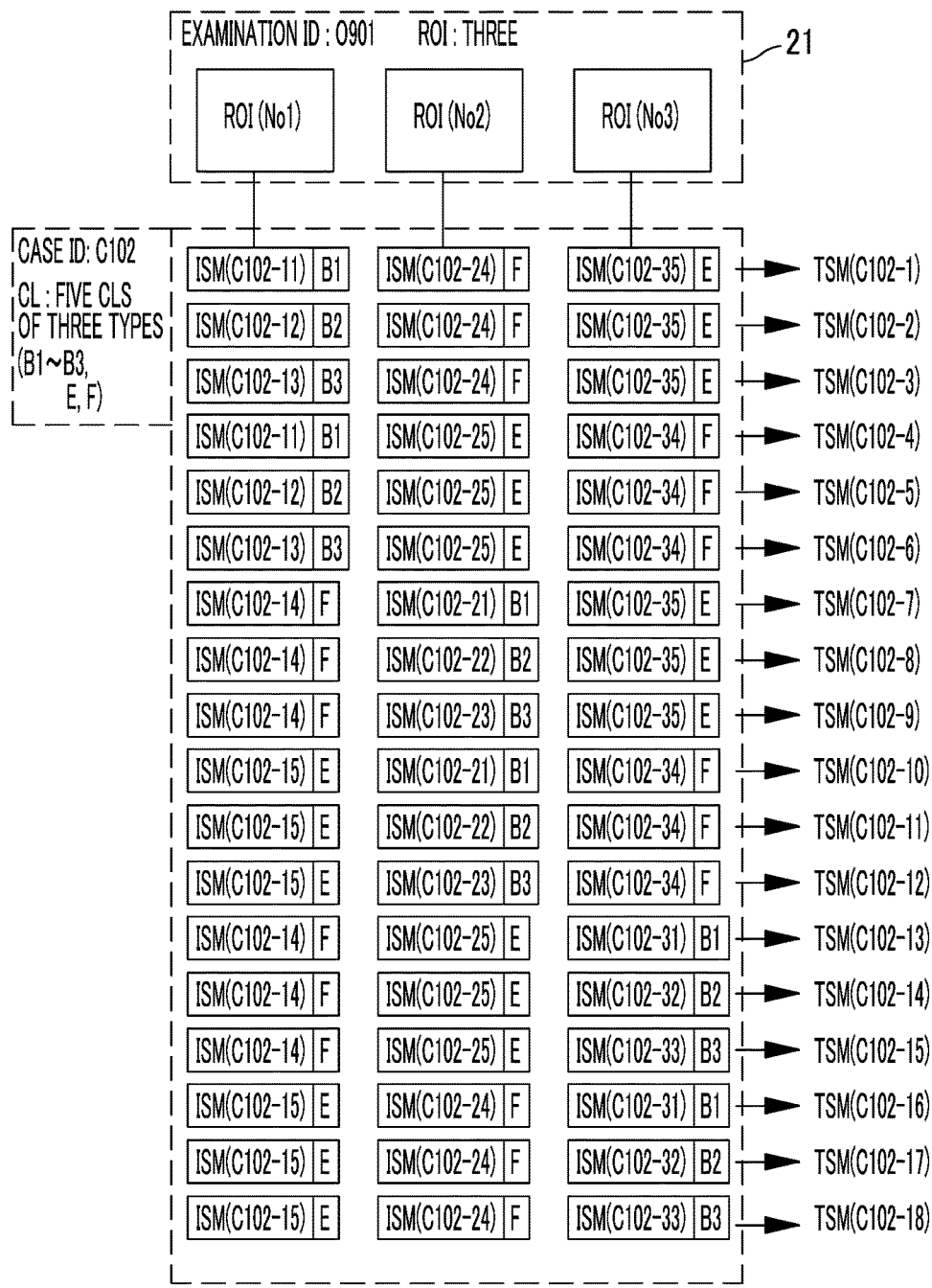
FIG. 29 is a diagram illustrating combinations of completely different types in a case in which there are five case lesions of three types.

In a case in which there are a plurality of case lesions CL (B1 to B3) of the same type as in the case with the case ID "C102", the number of combinations of completely different types in the case with the case ID "C102" is not equal to the number of permutations and is 18 as illustrated in FIG. 29, unlike the case with the case ID "C101" in which the case lesions CL are different types. That is, 18 total similarities TSM (C102-1) to TSM (C102-18) are calculated.

Figure 30:
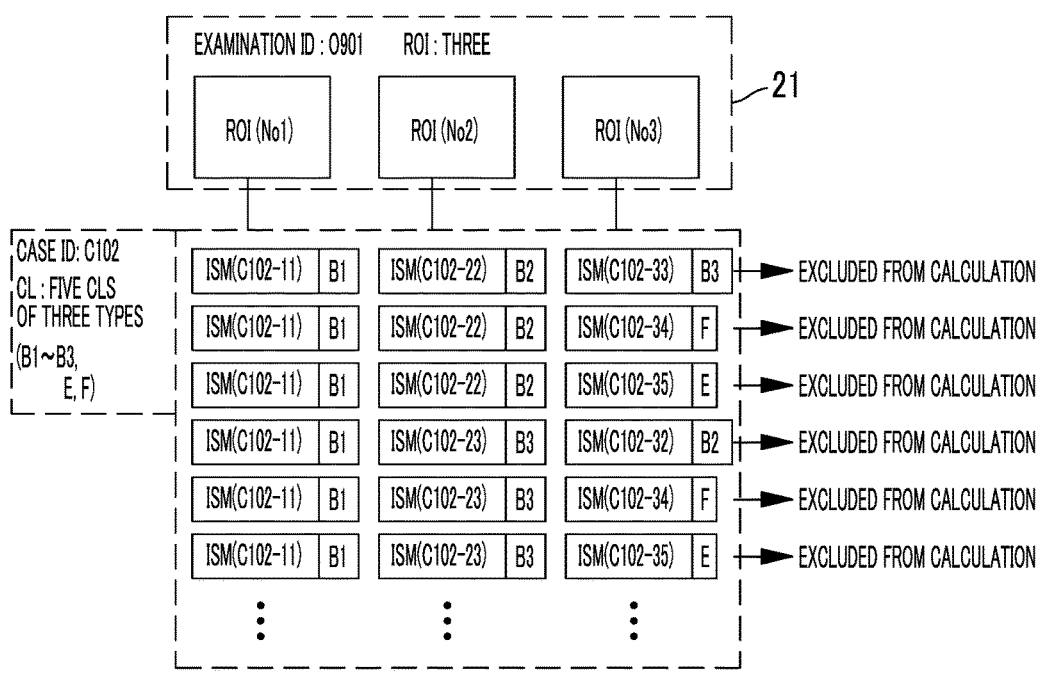
FIG. 30 is a diagram illustrating combinations which are excluded from calculation targets in the example illustrated in FIG. 29.

In the case with the case ID "C102", in the event that the number of permutations is calculated as in the case with the case ID "C101", three case lesions CL corresponding to the number of regions of interest ROI are extracted from five case lesions CL in the case with the case ID "C102". Therefore, $_5P_3=5\times4\times3=60$ is established. The number of combinations of completely different types is a value obtained by subtracting the number of combinations of the individual similarities of the same type, such as "B1, B2, B3" and "B1, B3, B2", or the number of combinations of the individual similarities, some of which are the same type, such as "B1, B2, F" and "B1, B2, E" illustrated in FIG. 30, from the number of permutations. The total similarity calculation unit 66 determines that the combinations of completely different types illustrated in FIG. 29 are not used to calculate the total similarity TSM and the combinations of completely different types illustrated in FIG. 30 are used to calculate the total similarity TSM.

Figure 31:
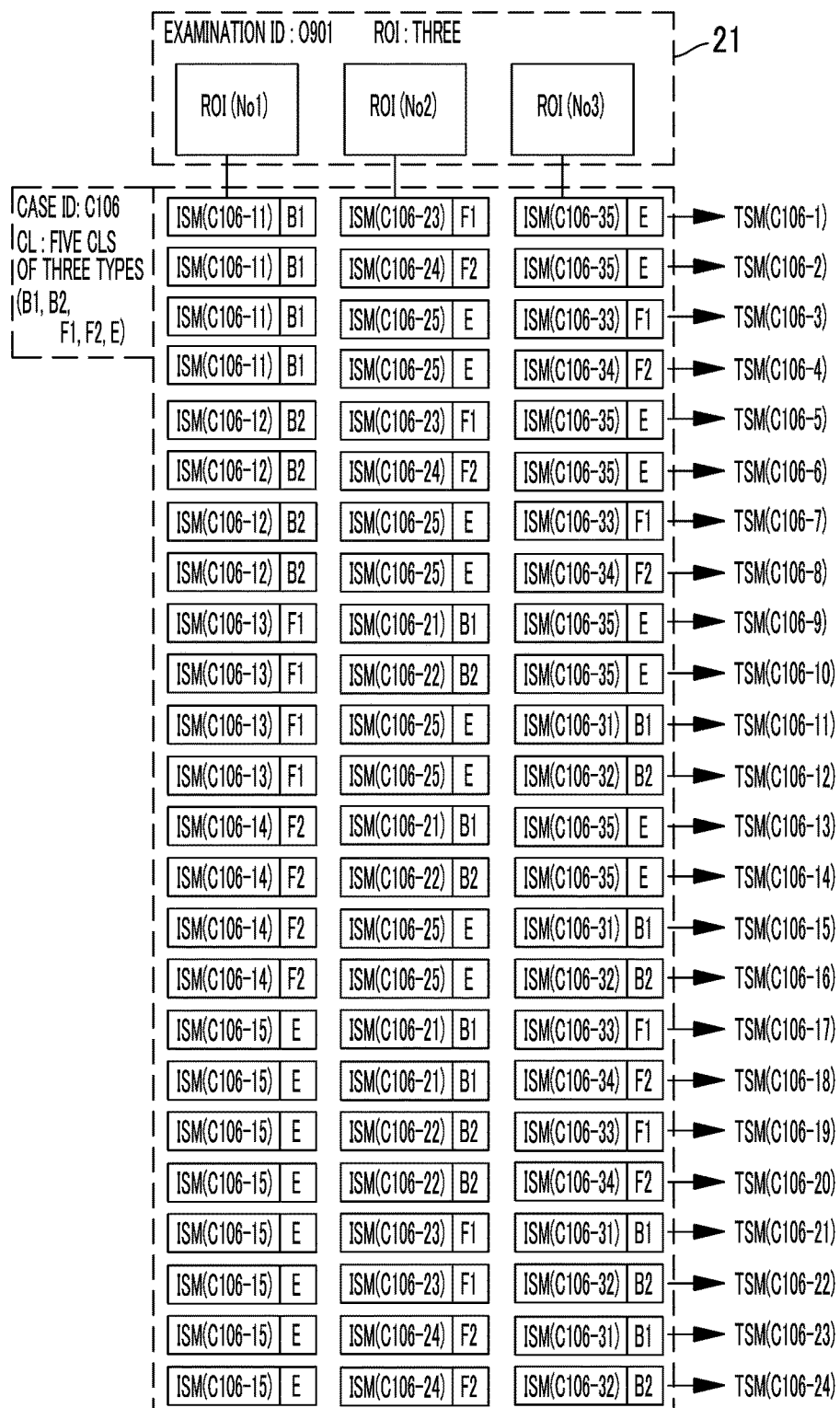
FIG. 31 is a diagram illustrating combinations of completely different types in the example illustrated in FIG. 22.
Figure 32:
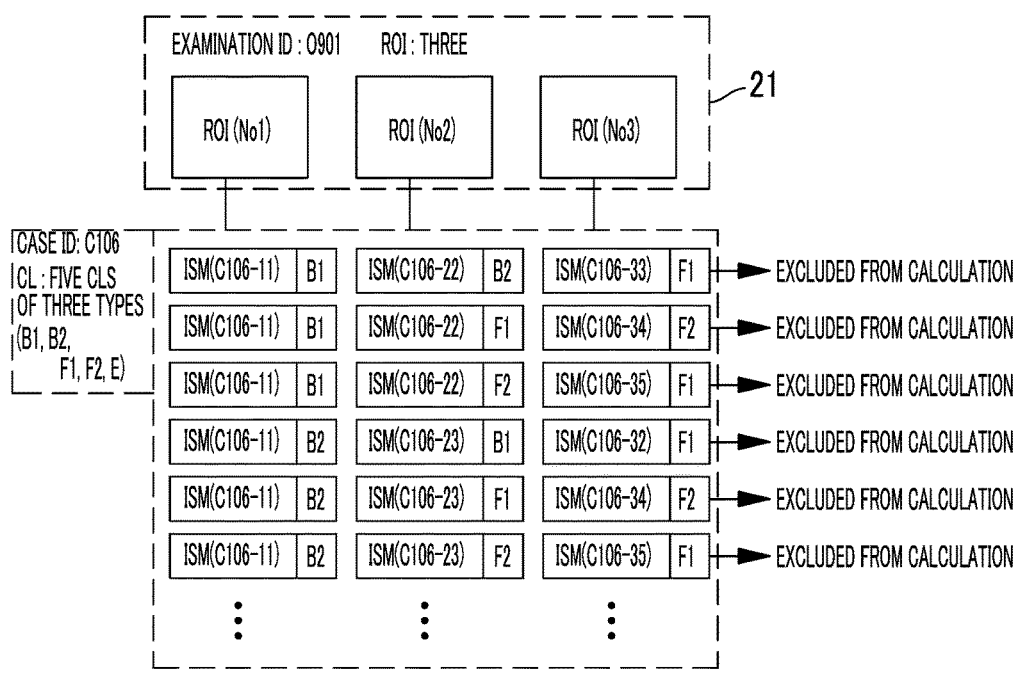
FIG. 32 is a diagram illustrating combinations which are excluded from calculation targets in the example illustrated in FIG. 31.

In a case in which five case lesions CL of three types are included in the case with the case ID "C106" illustrated in FIG. 31, similarly to the case with the case ID "C102", in the event that the breakdown of five case lesions CL of three types varies, the number of combinations of completely different types varies. In the case with the case ID "C106", the breakdown of five case lesions CL of three types is that the number of types "B" is 2 (B1 and B2), the number of types "F" is 2 (F1 and F2), the number of types "E" is 1. Therefore, the number of combinations of completely different types, such as "B1, F1, E" and "B1, F2, E", is 24. The total similarity calculation unit 66 determines that 24 combinations of completely different types illustrated in FIG. 31 are used to calculate the total similarities TSM and calculates 24 total similarities TSM (C106-1 to C106-24). In contrast, as illustrated in FIG. 32, the total similarity calculation unit 66 does not use combinations other than the combinations of completely different types to calculate the total similarities TSM. For example, the combinations other than the combinations of completely different types are combinations of the individual similarities, some of which are the same type, such as "B1, B2, F1" and "B1, F1, F2".

As such, since only the combinations of completely different types are used to calculate the total similarities TSM, the combinations used to calculate the total similarities TSM are narrowed down. Therefore, the processing time or processing load of the total similarity calculation unit 66 is reduced and it is possible to reduce the time required to search for a similar case. As described above, in the invention, the main reason why attention is paid to a plurality of regions of interest ROI to search for a similar case is that three types of target lesions, that is, vomica, a punctate shadow, and a frosted glass shadow are used to diagnose a non-cancerous diagnosis, such as tuberculosis which is specified on the basis of the three types of target lesions. Therefore, as a case that is similar to a plurality of regions of interest ROI including different types of target lesions OL, a case including different types of case lesions CL needs to be searched as a similar case.

In the event that the purpose of the target lesions used to diagnose a non-cancerous disease is considered, in many cases, a plurality of regions of interest ROI are designated so as to include different types of target lesion OL. In this case, the necessity to extract a case including the case lesions CL of the same type is low. Therefore, even assuming that only the combinations of completely different types are used to calculate the total similarities TSM, the influence of the restrictions on the actual diagnosis is small.

Figure 33:
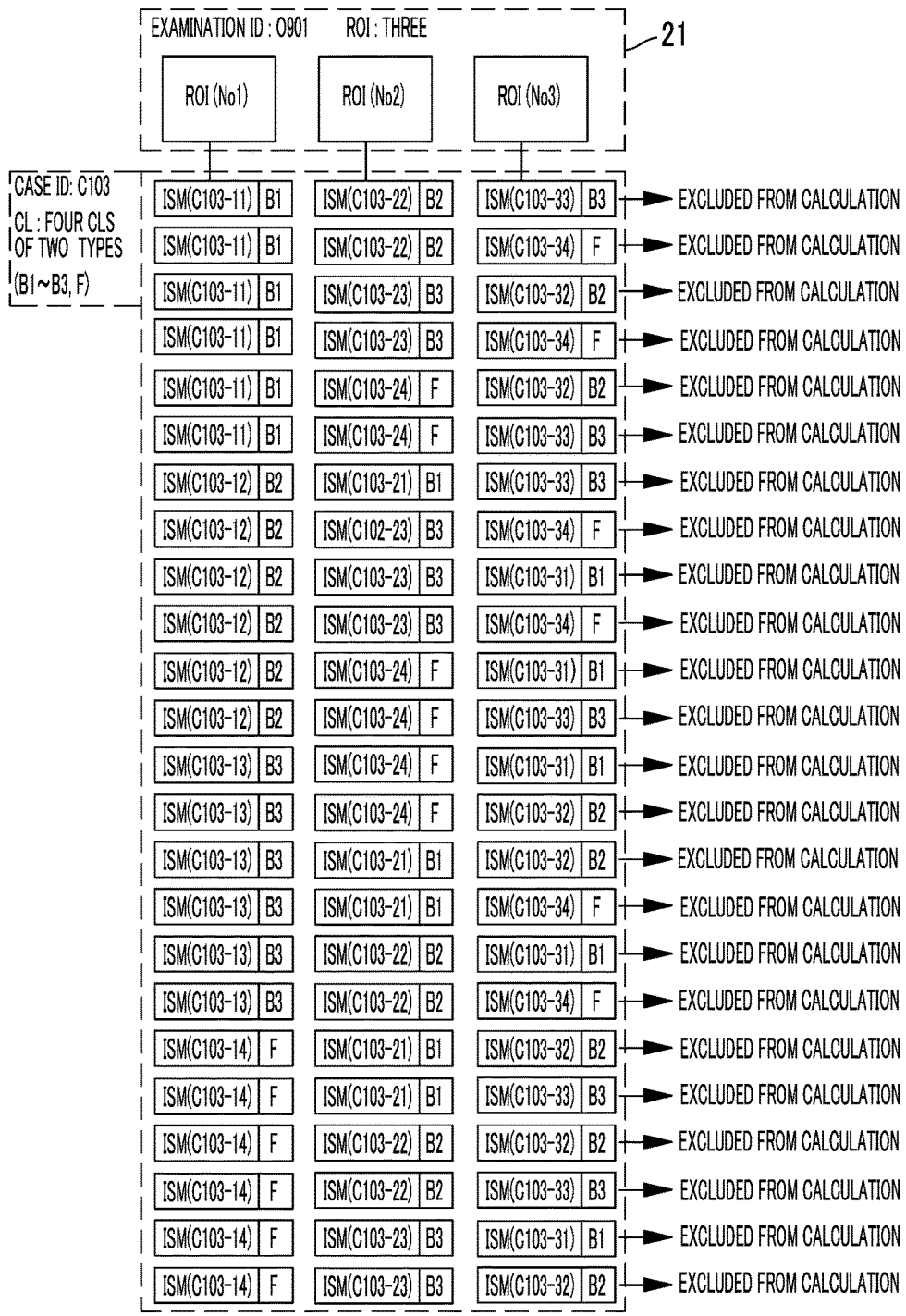
FIG. 33 is a diagram illustrating cases which are excluded from search targets.

For this reason, the total similarity calculation unit 66 does not calculate the total similarity TSM for the case with the case ID "C103" including four case lesions CL of two types illustrated in FIG. 33 or the case with the case ID "C104" including four case lesions CL of the same type illustrated in FIG. 34 since the number of types of case lesions CL is less than the number of regions of interest ROI. In a case in which the case lesions CL are the same type as in the case with the case ID "C104", the necessity to set the case as a search target is low, considering the purpose of searching for different types of case lesions CL.

A case in which the number of types of case lesions CL is less than the number of regions of interest ROI, such as the case with the case ID "C103", is excluded from the search target since the necessity to set the case as the search target is low. That is, in the diagnosis of a non-cancerous, the doctor designates three regions of interest ROI for the following reasons: the doctor wants to search for a case including three types of case lesions CL; and it is considered that, even assuming that the number of types of case lesions CL is less than the number of regions of interest ROI is extracted, the necessity of the case regions CL for diagnosis is considered to be low. In this example, the total similarity TSM is not calculated for the case with the case ID "C103" including two types of case lesions CL since three regions of interest ROI are assumed in this example. In a case in which there are two regions of interest ROI, the total similarity TSM is calculated for the case with the case ID "C103".

As illustrated in FIG. 35, to summarize the above-mentioned content, the total similarity calculation unit 66 calculates the total similarity TSM for only the case in which the number of types of case lesions CL is equal to or greater than the number of regions of interest ROI, such as the cases with the cases ID "C101", "C102", "C105", and "C106", and uses the case as a similar case search target. The total similarity TSM is calculated for only combinations of completely different types. On the contrary, the total similarity calculation unit 66 does not calculate the total similarity TSM for the case in which the number of registered case lesions CL is less than the number of regions of interest ROI (in this example, the number of case lesions CL is less than 3), such as the cases with the cases ID "C103" and "C104", and excludes the case from the search target.

As illustrated in FIG. 36, the total similarity calculation unit 66 records the total similarities TSM calculated for a plurality of cases which are search targets in the TSM table 72. In the TSM table 72, one record includes three data items, that is, the case ID, the total similarity TSM, and the combination patterns of the individual similarities ISM. The combination pattern is a combination of the individual similarities ISM used to calculate each total similarity TSM.

The total similarity calculation unit 66 transmits the created TSM table 72 to the similar case search unit 67. In FIG. 12, the similar case search unit 67 is provided with a representative value determination unit 67B.

Figure 37:
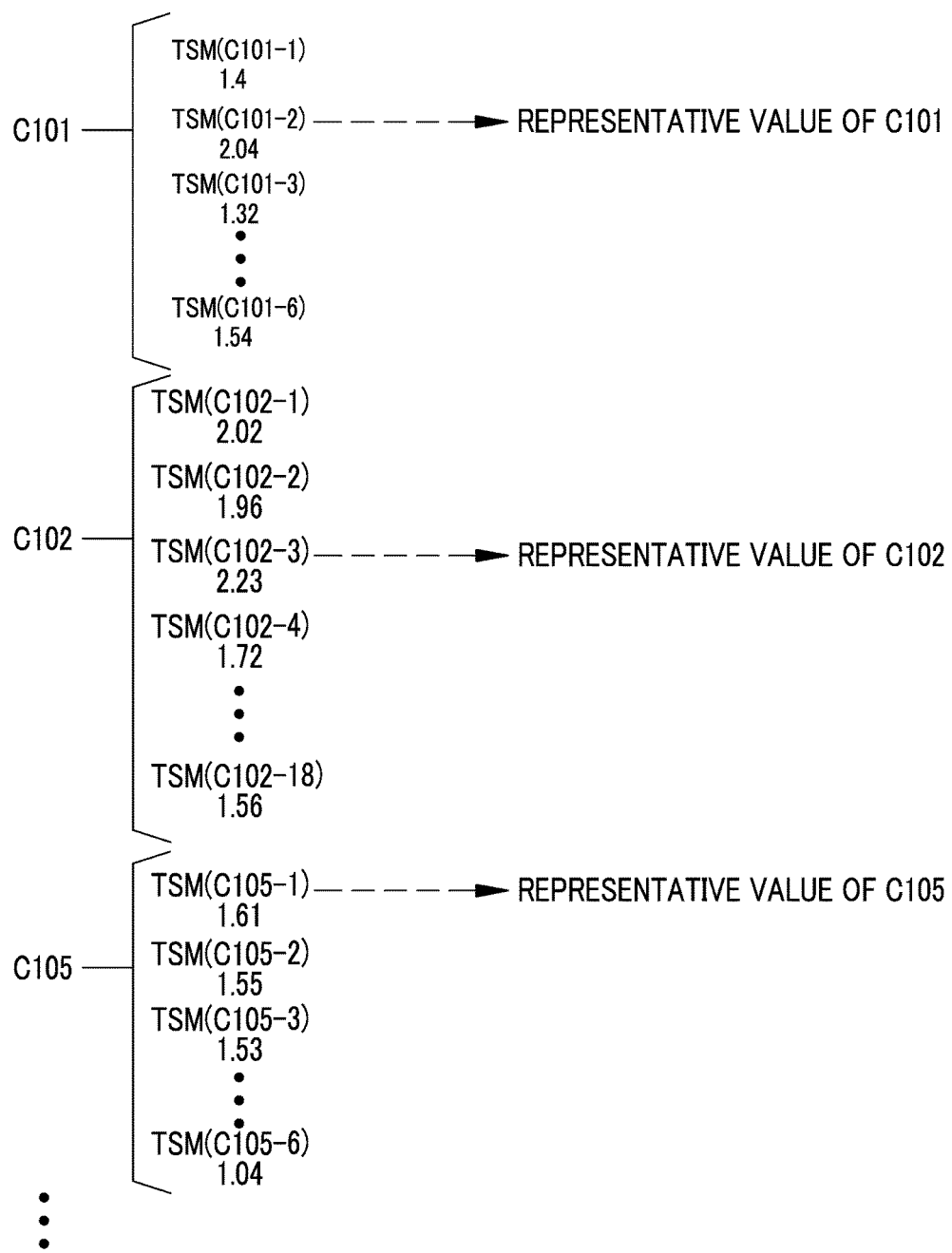
FIG. 37 is a diagram illustrating a method for determining the representative values of the total similarities for each case.

As illustrated in FIG. 37, the representative value determination unit 67B determines a representative value for each case from a plurality of total similarities TSM in the TSM table 72. In the case with the case ID "C101", among six total similarities TSM, the total similarity TSM (C101-2) with the highest value (maximum correlation value) is determined to be the representative value. Similarly, in the case with the case ID "C102", among 18 total similarities TSM, the total similarity TSM (C102-3) with the highest value (maximum correlation value) is determined to be the representative value.

Figure 38:
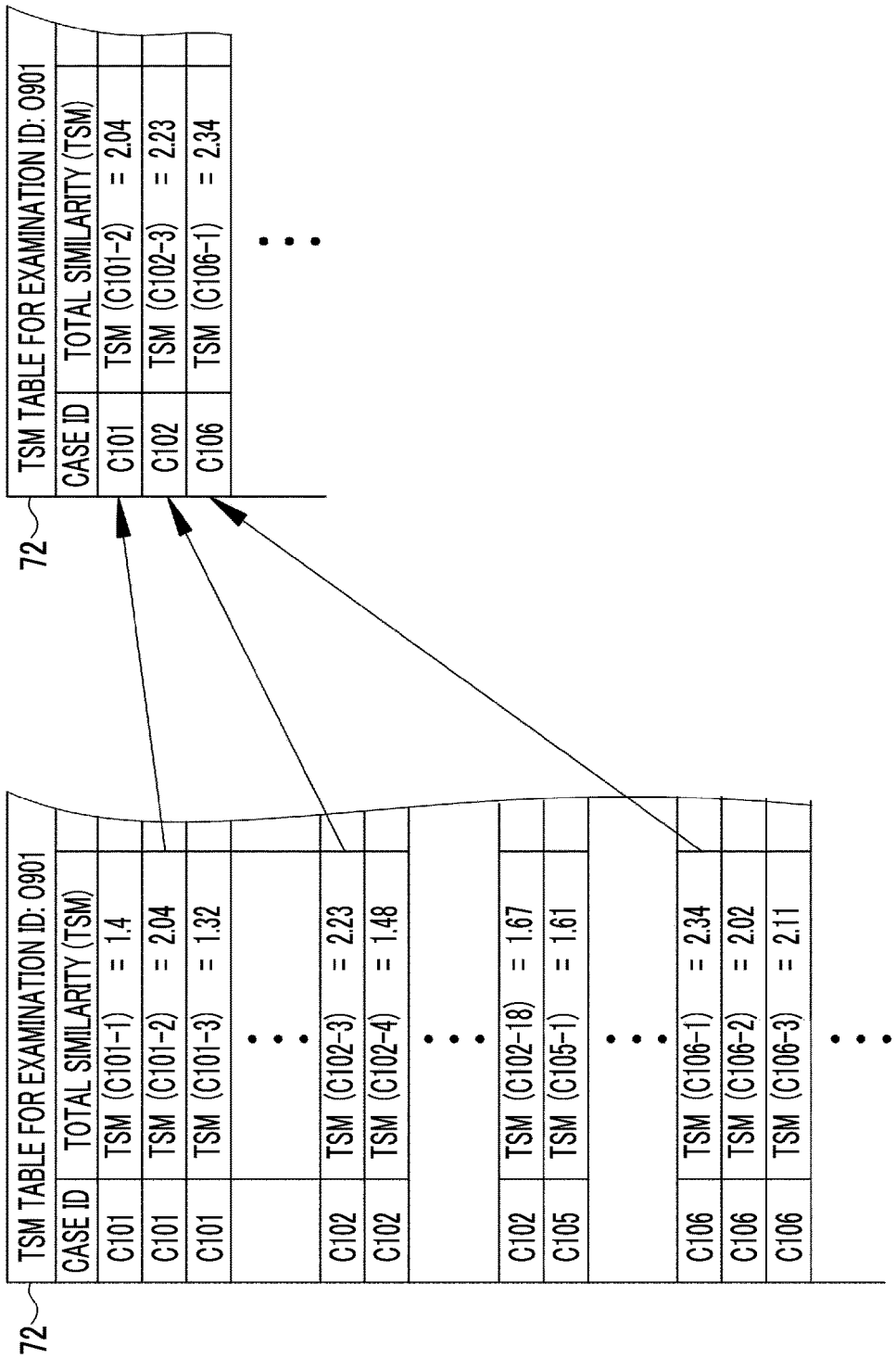
FIG. 38 is a diagram illustrating a table in which the representative values for each case are arranged.

As illustrated in FIG. 38, the representative value determination unit 67B performs the representative value determination process for all of the cases in the TSM table 72. In this way, only the representative total similarities TSM determined for each case are extracted from the TSM table 72.

Figure 39:
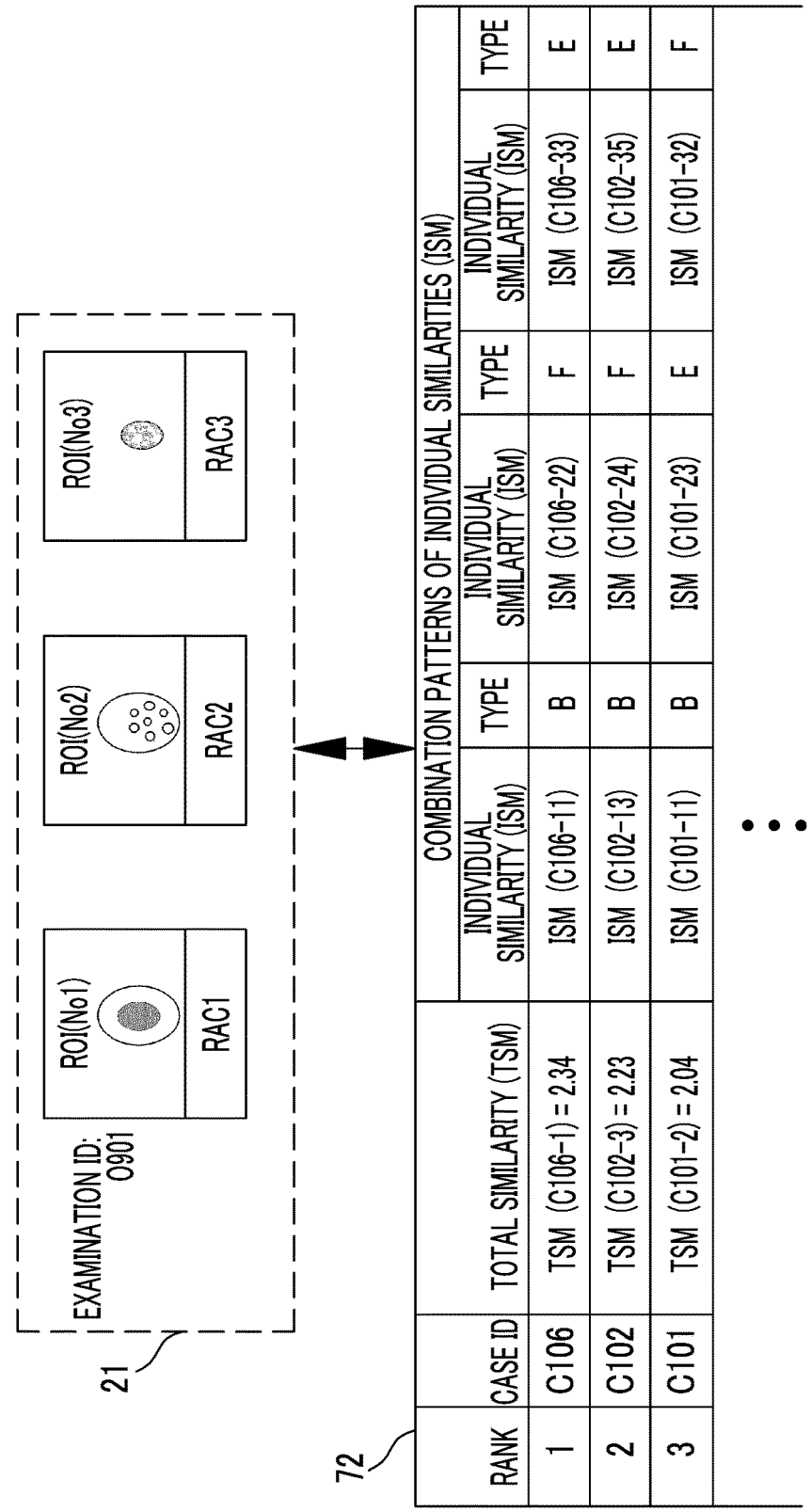
FIG. 39 is a diagram illustrating a table in which the representative values for each case are sorted.

As illustrated in FIG. 39, the similar case search unit 67 sorts records in descending order of the total similarity TSM in the TSM table 72 for the representative value extraction has been performed. In the TSM table 72, since only one total similarity TSM is extracted from one case, the sorting of records means that the cases are sorted in descending order of the total similarity TSM. In this way, the cases are ranked and extracted such that a similar case with a higher similarity is ranked higher in the TSM table 72.

Figure 40:
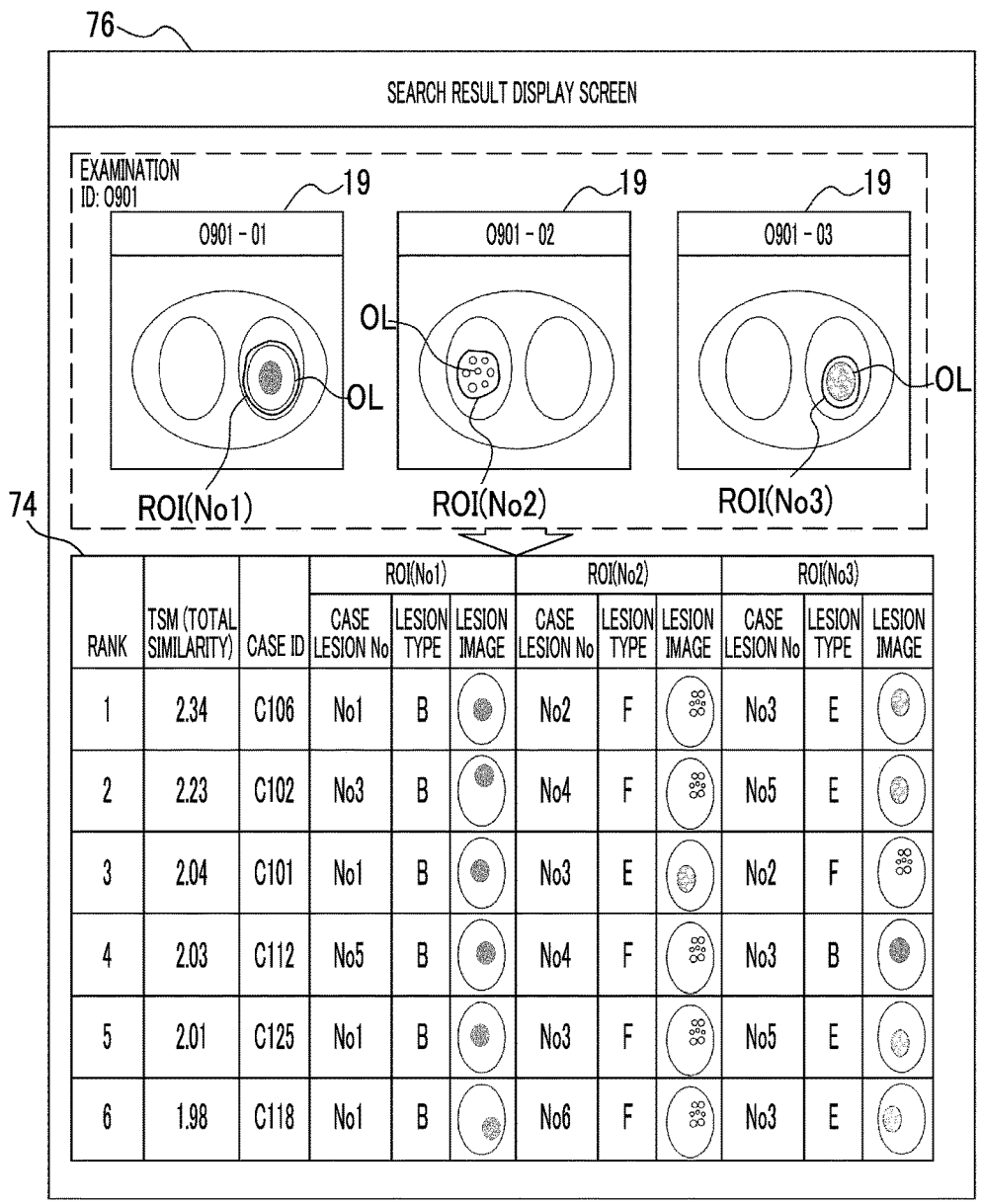
FIG. 40 is a diagram illustrating a screen on which a similar case list is displayed.

The similar case search unit 67 is provided with a list creation unit 67A (see FIG. 12). The list creation unit 67A creates a similar case list 74 illustrated in FIG. 40 on the basis of the TSM table 72. The similar case list 74 is displayed on a search result display screen 76. The similar case list 74 is a list of information related to a plurality of similar cases. The search result display screen 76 is an example of a screen that is transmitted as the search result from the similar case search server 17 to the treatment department terminal 11 which is the request source of the similar case search request.

The list creation unit 67A extracts the total similarities TSM from the TSM table 72 and creates the similar case list 74 in which similar cases are arranged in descending order of the total similarity TSM. Display items of the similar case list 74 include the value of each total similarity TSM, a rank based on each total similarity TSM, a case ID, and breakdown information related to each total similarity TSM. In this example, the breakdown information is the correspondence relationship between the region of interest ROI and the case lesion CL for calculating each individual similarity ISM which is an element for calculating the total similarity TSM. The breakdown information also includes the type of case lesion CL (lesion type).

In the similar case list 74, the total similarity TSM for the case with the case ID "C106" corresponds to a total similarity TSM with an identification code "C106-1" illustrated in FIG. 39. A combination pattern of the individual similarities ISM, which are elements for calculating the total similarity TSM with the identification code "C106-1", is individual similarities ISM (C106-11), ISM (C106-22), and ISM (C106-33). The breakdown information which is displayed in the similar case list 74 is the correspondence relationship between the regions of interest ROI and the case lesions CL for calculating each individual similarity ISM. The individual similarity ISM (C106-11) is calculated by the correspondence between the region of interest ROI with No1 and the case lesion CL with No1 in the case with the case ID "C106". The individual similarity ISM (C106-22) is calculated by the correspondence between the region of interest ROI with No2 and the case lesion CL with No2 in the case with the case ID "C106". The individual similarity ISM (C106-33) is calculated by the correspondence between the region of interest ROI with No3 and the case lesion CL with No3 in the case with the case ID "C106". Since the type of case lesion is also displayed in the correspondence relationship, it is possible to check which type the combination pattern of the individual similarities ISM corresponds to.

In addition, the display items of the similar case list 74 include the images of the case lesions CL with No1, No2, and No3. The lesion images are read from, for example, the ISM table 71. In addition, the examination images 19 including the regions of interest ROI with No1 to No3 are displayed above the similar case list 74.

For example, the top six cases are displayed in the similar case list 74. Of course, the cases in sixth place or lower may be displayed by, for example, a screen scroll operation. In addition, the number of cases which can be displayed at the same time may be changed such that the top ten cases are displayed.

The output control unit 69 (see FIG. 12) performs control such that extensible markup language (XML) data for web distribution is created for the created search result display screen 76 by a markup language, such as XML, and is transmitted as the search result to the treatment department terminal 11 which is a request source. In the treatment department terminal 11 which has received the XML data, a web browser reproduces the search result display screen 76 on the basis of the XML data and displays the search result display screen 76 on the display unit 48A. In this way, the doctor browses the search result display screen 76 including the similar case list 74.

Figure 41:
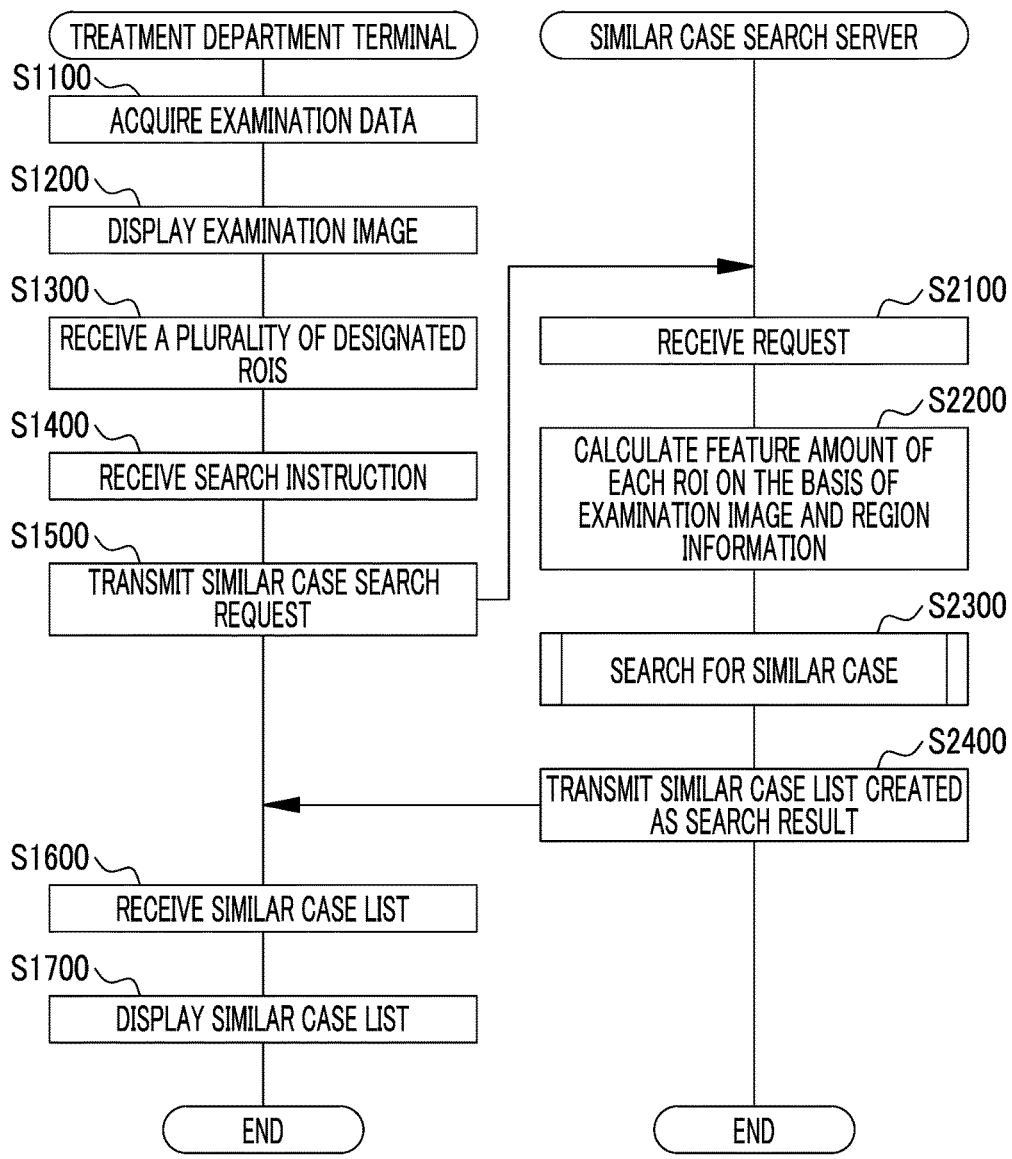
FIG. 41 is a flowchart illustrating a process of a similar case image search device.

Next, the operation of the above-mentioned structure will be described with reference to FIGS. 41 and 42. As illustrated in FIG. 41, the doctor in the treatment department 10 accesses the examination image DB server 15, using the treatment department terminal 11, and acquires the examination data 21 of the examination requested to the examination department 12 (S1100). The treatment department terminal 11 displays the examination data 21 on the display unit 48A (S1200). The examination images 19 included in the acquired examination data 21 are displayed on the examination image display screen 52 illustrated in FIG. 10. The doctor designates the regions of interest ROI in the examination images 19 through the examination image display screen 52. The treatment department terminal 11 receives a plurality of regions of interest ROI designated by the designation operation of the doctor (S1300).

In the designation of the region of interest ROI, in the event that a non-cancerous disease, such as tuberculosis or diffuse panbronchiolitis, is diagnosed, a plurality of regions of interest ROI are designated so as to include different types of target lesions OL. In the event that the designation of the regions of interest ROI ends, the similar case search button 52E is operated. Then, the treatment department terminal 11 receives a search instruction (S1400). In the event that the search instruction is received, the search request issuing unit 54 issues a similar case search request to which the examination images 19 and region information are added and transmits the similar case search request to the similar case search server 17 (S1500).

In the event that the similar case search server 17 receives the similar case search request, the request receiving unit 61 receives the similar case search request (S2100). Then, the feature amount calculation unit 62 calculates the feature amount of each region of interest ROI on the basis of the examination images 19 and the region information of the regions of interest ROI (S2200). Then, a similar case search process is performed (S2300).

Figure 42:
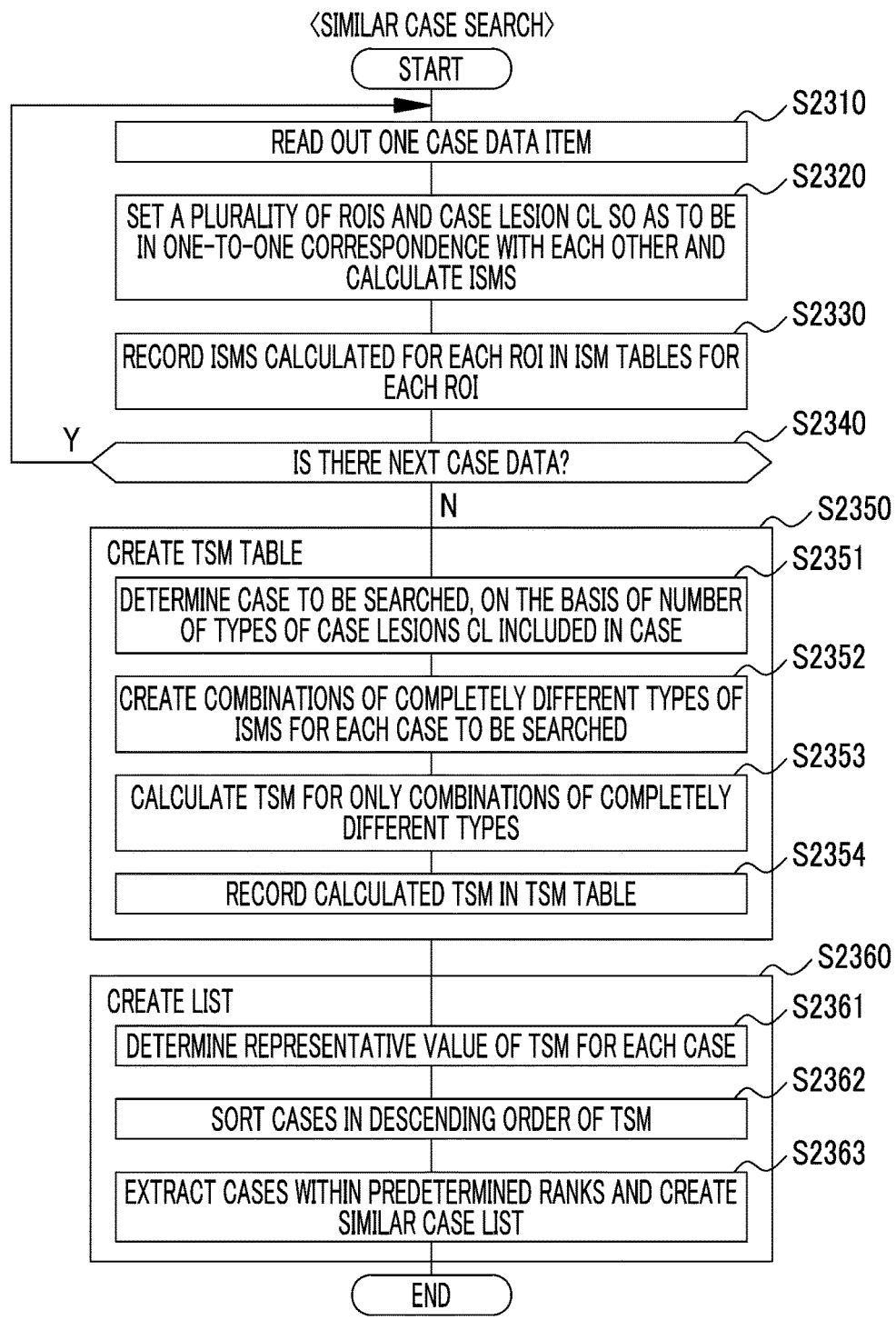
FIG. 42 is a flowchart illustrating a similar case search process.

As illustrated in FIG. 42, in the similar case search process, first, the individual similarity calculation unit 65 reads out one case data item 24 from the case DB server 16 (S2310). Then, the individual similarity calculation unit 65 calculates the individual similarities ISM using the one-to-one correspondence between a plurality of regions of interest ROI in the examination data 21 and the case lesions CL included in one case data item 24 (S2320). In the event that there are a plurality of case lesions CL, the individual similarity ISM is calculated for each case lesion CL. The individual similarity calculation unit 65 records the calculated individual similarities ISM in the ISM table 71 and creates the ISM table 71 for each region of interest ROI (S2330). After this process is performed for one case data item 24, it is performed for the next case data 24 using the same method as described above. Then, the same process is repeatedly performed until the calculation of the individual similarity ISM and the creation of the ISM table 71 for a plurality of case data items 24, for example, all of the case data 24 in the case DB 23 end (N in S2340).

The total similarity calculation unit 66 creates the TSM table 72 on the basis of a plurality of ISM tables 71 created for each region of interest ROI (S2350). In the creation of the TSM table 72, first, the total similarity calculation unit 66 determines a case to be searched, on the basis of the number of types of case lesions CL in each case (S2350). A case including only one type of case lesion CL, such as the case with the case ID "C104" illustrated in FIG. 34, and a case in which the number of types of case lesions CL is less than the number of regions of interest ROI, such as the case with the case ID "C105" illustrated in FIG. 33, are determined to be excluded from the search target by the above-mentioned determination process.

Then, the total similarity calculation unit 66 creates combinations of completely different types of individual similarities ISM for each case to be searched (S2352) and calculates the total similarity TSM for only the created combinations of completely different types (S2353). The total similarity calculation unit 66 creates 18 combinations of completely different types for the case with the case ID "C102" illustrated in FIG. 29 and determines that the 18 combinations are used to calculate the total similarity TSM. Then, the total similarity calculation unit 66 calculates 18 total similarities TSM (C102-1 to C102-18) for each of the combinations that have been determined to be used for the calculation of the total similarity TSM. In contrast, the total similarity calculation unit 66 determines that the combinations of the individual similarities of the same type or the combinations of the individual similarities, some of which are the same type, illustrated in FIG. 30 are not used to calculate the total similarity TSM and does not calculate the total similarity TSM.

Similarly, the total similarity calculation unit 66 creates 24 combinations of completely different types for the case with the case ID "C106", as illustrated in FIG. 31, and calculates 24 total similarities TSM (C106-1 to C106-24) corresponding to 24 combinations. In contrast, the total similarity calculation unit 66 determines that the combinations of the individual similarities of the same type or the combinations of the individual similarities, some of which are the same type, illustrated in FIG. 32 are not used to calculate the total similarity TSM and does not calculate the total similarity TSM. Then, the total similarity calculation unit 66 records the calculated total similarities TSM for each case in the TSM table 72 (S2354).

The similar case search unit 67 creates the similar case list 74 on the basis of the created TSM table 72 (S2360). In the creation of the list, first, as illustrated in FIG. 38, the representative value determination unit 67B determines representative values from a plurality of total similarities TSM for each case in the TSM table 72 (S2361), extracts only the representative total similarities TSM for each case, and creates the TSM table 72. Then, the similar case search unit 67 sorts the cases in descending order of the total similarity TSM in the TSM table 72 (S2362). In this way, a similar case with a higher similarity is extracted and ranked higher in the TSM table 72.

The list creation unit 67A extracts the cases within predetermined ranks on the basis of the TSM table 72 and creates the similar case list 74 in which similar cases are arranged in descending order of the total similarity TSM (S2363).

In FIG. 41, the output control unit 69 converts the search result display screen 76 including the similar case list 74 which has been created as the search result by the list creation unit 67A into XML data for distribution and transmits the XML data to the treatment department terminal 11 (S2400). The treatment department terminal 11 receives the XML data including the similar case list 74 (S1600), reproduces the search result display screen 76 (see FIG. 30) on the basis of the XML data, and displays the search result display screen 76 on the display unit 48A (S1700).

In a case in which the examination data 21 includes a plurality of target lesions OL and a case similar to the examination data 21 is searched, it is preferable that a search process is performed, comprehensively considering each of the feature amounts of a plurality of regions of interest ROI including each target lesion OL and a plurality of case lesions CL, in addition to paying attention to the feature amounts. For example, in a certain case in which one case lesion CL has high similarity to one region of interest ROI and another case lesion CL has a very low similarity to another region of interest ROI, the case is not appropriate as a similar case in the event that attention is to be paid to at least a plurality of regions of interest ROI.

In the invention, the individual similarities ISM between each region of interest ROI and each case lesion CL are calculated and the total similarity TSM is calculated on the basis of the calculated individual similarities ISM. Then, a similar case is searched. The total similarity TSM is an index for evaluating a case in which the average value of a plurality of individual similarities ISM is high to be a case with high similarity. The search of a similar case on the basis of the total similarity TSM makes it possible to appropriately search for a similar case with high similarity to the examination data 21 including a plurality of target lesions OL.

In the related art, only a similar case search process in which attention is paid to only the feature amount of one region of interest ROI is performed. Therefore, it is difficult to appropriately search for a similar case in a similar case search process in a case in which there are a plurality of regions of interest ROI. In contrast, in the invention, a similar case is searched on the basis of the total similarity TSM. Therefore, it is possible to provide a technique that is more useful than the related art in the similar case search process in a case in which there are a plurality of regions of interest ROI.

In some cases, in a non-cancerous disease, such as tuberculosis in which attention needs to be paid to three types of target lesions OL, that is, a vomica shadow (cavity), a punctate shadow (small nodules), and a frosted glass shadow (ground glass opacity), or diffuse panbronchiolitis in which attention needs to be paid to two types of target lesions OL, that is, an abnormal shadow of the bronchus and a punctate shadow, the disease is specified on the basis of whether a plurality of target lesions OL appear. As such, the invention is useful to diagnose a non-cancerous disease in which attention needs to be paid to the feature amounts of a plurality of regions of interest ROI.

In the invention, for the total similarity TSM, only the combinations of completely different types of individual similarities are used to calculate the total similarity TSM and the combinations of the individual similarities used to calculate the total similarity TSM is narrowed down. Therefore, it is possible to reduce the processing time or processing load of the total similarity calculation unit 66 and to reduce the time required to search for a similar case. An example in which three regions of interest ROI correspond to five case lesions CL of three types in the case with the case ID "C102" illustrated in FIGS. 29 and 30 will be described. The number of permutations including combinations other than the combinations of completely different types is $_5P_3=5\times4\times3=60$ and the number of combinations of completely different types is 18. Therefore, it is possible to reduce the time required to calculate the total similarity TSM by about ⅔, considering only the number of combinations relate to the case with the case ID "C102".

As such, in a case in which the similar case search process is used to diagnose a non-cancerous disease, even assuming that elements for calculating the total similarities TSM are limited to combinations of completely different types, the influence of the limitation on the actual diagnosis is small. The reason is as follows. In a case in which the similar case search process is used to diagnose a non-cancerous disease, since a plurality of regions of interest ROI are designated so as to include different types of target lesion OL, the necessity to extract the cases including the case lesions CL of the same type is low. Therefore, even assuming that the individual similarities used to calculate the total similarity TSM are limited to combinations of completely different types of individual similarities, it is possible to extract necessary similar cases.

In this example, the individual similarity ISM is calculated even for the case for which the total similarity TSM is determined not to be calculated by the total similarity calculation unit 66. However, the individual similarity ISM may not be calculated even for the case for which the total similarity TSM is determined not to be calculated by the total similarity calculation unit 66. For example, in this example, a case in which the number of types of case lesions CL is less than the number of regions of interest ROI, such as the case with the case ID "C103" including four case lesions CL of two types or the case with the case ID "C104" including four case lesions CL of the same type illustrated in FIG. 31, is determined to be excluded from the search target, as illustrated in FIG. 35. In the event of calculating the individual similarity ISM, the individual similarity calculation unit 65 determines that the case is excluded from the search target and does not calculate the individual similarity ISM for the case. The individual similarity calculation unit 65 determines a search target on the basis of the number of types of case lesions CL and the number of regions of interest ROI. According to this structure, it is possible to reduce the waste of the processing time and thus to further reduce the search time.

In this example, the total similarity TSM is the sum of a plurality of individual similarities ISM. However, the total similarity TSM may be the product of the individual similarities ISM.

In this example, the representative value determination unit 67B determines a representative value for each case from a plurality of total similarities TSM calculated for each case and the similar case search process is performed on the basis of only the representative values. The determination of the representative values makes it possible to obtain the effect of reducing the amount of data treated in the search process, such as the number of total similarities TSM recorded in the TSM table 72, to reduce the processing time. The diagnosis result, such as the doctor's opinion on the case lesion CL, which is described in the radiogram interpretation report, is present for each case. Therefore, the determination of the representative values makes it possible to provide the search results for each case and to appropriately and effectively perform a diagnosis on the basis of the similar case. However, the similar case search process may be performed without determining the representative value. In a case in which the representative value is not determined, a plurality of total similarities TSM of the same case may be displayed in the similar case list 74. The plurality of total similarities TSM are different combination patterns of the individual similarities ISM which are elements for calculating the total similarities TSM. Therefore, it is possible to refer to the plurality of total similarities TSM while changing a point of view for one case.

The display items of the similar case list 74 include breakdown information related to the total similarity TSM, in addition to the case ID of a similar case and the total similarity TSM. It is possible to check the correspondence relationship between the regions of interest ROI and the case lesions CL for calculating each individual similarity ISM, which is an element for calculating the total similarity TSM, from the breakdown information. The display of the correspondence relationship makes it possible to check the correspondence relationship between a plurality of regions of interest ROI and a plurality of case lesions CL used to calculate each individual similarity ISM which is an element for calculating the total similarity TSM. In addition, the examination image 19 or the image of the case lesion CL is also displayed in the similar case list 74. Therefore, it is easy to compare or refer to the image patterns and to intuitively determine the similarity between the image patterns.

Figure 43:
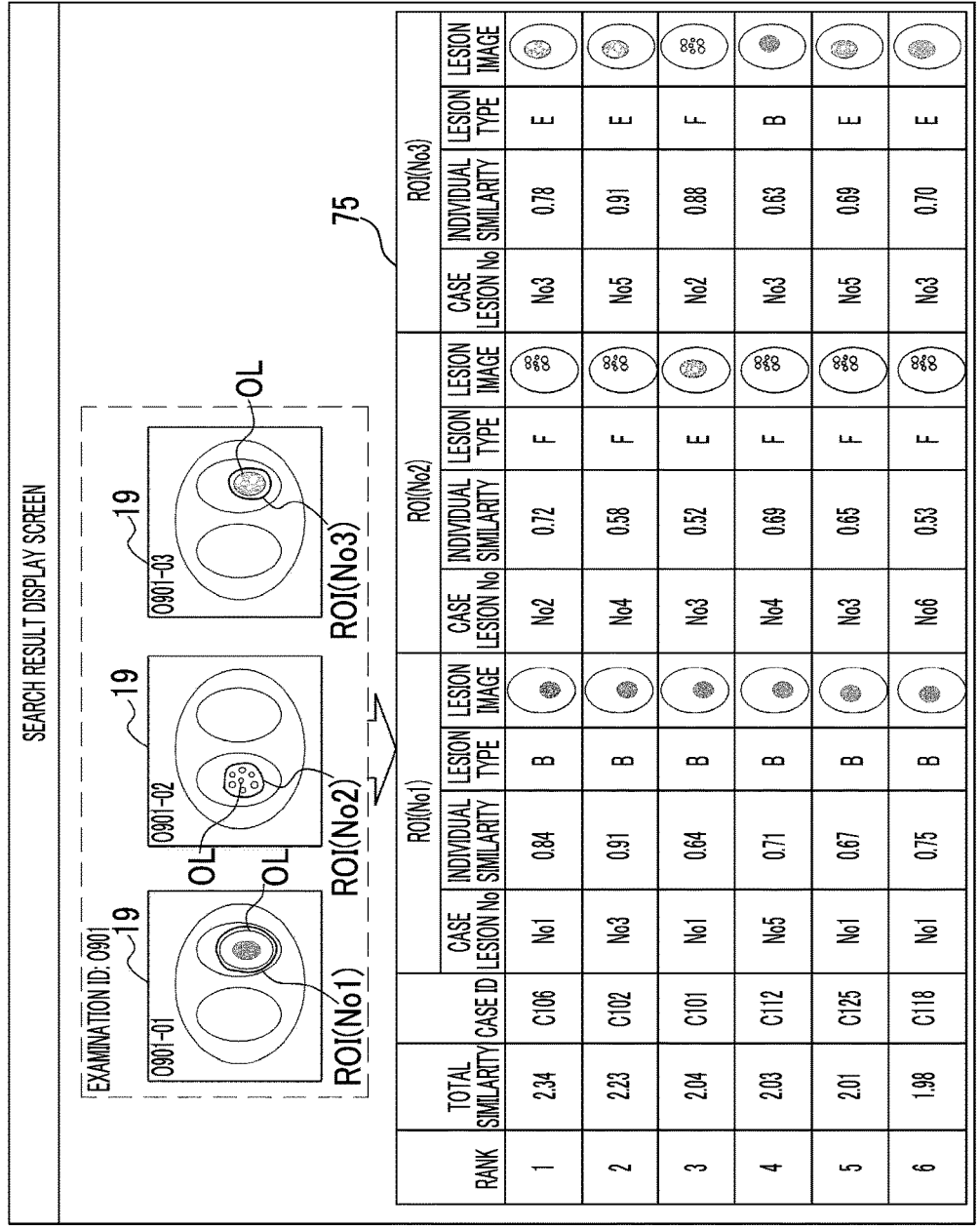
FIG. 43 is a diagram illustrating an example in which both the total similarity and the individual similarity are displayed.

As the breakdown information related to the total similarity TSM, the values of the individual similarities ISM, which are elements for calculating the total similarity TSM, may be displayed as in a similar case list 75 illustrated in FIG. 43. In the event that the values of the individual similarities ISM which are the breakdown of the total similarity TSM are displayed in addition to the total similarity TSM, it is possible to check whether the individual similarity ISM is high or low from the correspondence between each region of interest ROI and each case lesion CL, which is convenient. For example, in a case in which the doctor wants to place emphasis on one of a plurality of regions of interest ROI, the doctor can see the value of the individual similarity ISM for the region of interest ROI on which emphasis is placed and appropriately search for a similar case.

The total similarity TSM is an index for evaluating the case in which the average value of a plurality of individual similarities ISM is high to be a case with high similarity. Therefore, in the similar case list, the case in which the average value of a plurality of individual similarities ISM is high is ranked high and the case in which the average value is low, but one individual similarity ISM is particularly high is ranked low. In some cases, the subjective evaluation of the doctor on similarity is more greatly affected by the impression of the doctor on a specific case lesion CL and a specific region of interest ROI than by the average value. Therefore, in some cases, there is a difference between the subjective evaluation of the doctor and objective evaluation (rank) based on the total similarity TSM.

The display of the values of the individual similarities ISM in addition to the total similarity TSM as in the similar case list 75 makes it possible for the doctor to check the individual similarities ISM and to verify his or her subjective evaluation even assuming that the difference occurs. In addition, in the event that the values of the individual similarities ISM are displayed, the doctor can search for each similar case suitable for a diagnosis, while correcting the objective evaluation based on the total similarity TSM, using the similar case list 75, on the basis of the subjective evaluation of the doctor, considering the values of the individual similarities ISM.

In the invention, it is assumed that a plurality of regions of interest ROI including different types of target lesions OL are designated and the combinations of a plurality of individual similarities ISM for calculating the total similarities TSM are limited to combinations of completely different types of individual similarities ISM. Therefore, even in a case in which a plurality of regions of interest ROI including the same type of target lesions OL are designated (for example, two target lesions OL of the type "B: vomica"), combinations of the individual similarities ISM calculated by the correspondence between a plurality of regions of interest ROI of the same type and the case lesions CL of the same type are excluded from the combinations used to calculate the total similarity TSM. Therefore, the combinations are not extracted as a similar case in the similar case list.

Combinations of the individual similarities ISM calculated by the correspondence between a plurality of regions of interest ROI of the same type (for example, two regions of interest ROI corresponding to "B: vomica") and the case lesions CL (for example, "B: vomica" and "F: a punctate shadow" or "B: vomica" and "E: a frosted glass shadow"), at least one of which is the same type as the regions of interest ROI, are likely to be extracted as a similar case. In this case, it is considered that, in a case in which the region of interest ROI and the case lesion CL that are different types, such as "B" and "F", correspond to each other, the value of the individual similarity ISM is so small as to be negligible. That is, the total similarity TSM is affected by the values of the individual similarities ISM in a case in which the regions of interest ROI and the case lesions CL that are the same type correspond to each other. In the event that the values of the individual similarities ISM are displayed in addition to the values of the total similarities TSM as in the similar case list 75, it is easy to search for a case lesion CL having a high individual similarity ISM to a specific region of interest ROI.

For a total similarity calculation process, in the above-described embodiment, the individual similarities ISM are calculated for the case lesions CL in all of the cases, combinations of completely different types of individual similarities ISM are created for each case, and the total similarity TSM is calculated. The following method is used as the total similarity calculation process, in addition to the above-mentioned method. First, the individual similarities ISM are calculated for the case lesions CL included in not all of the cases but one case. Then, combinations of completely different types of individual similarities ISM are created for the case for which the individual similarities ISM have been calculated and the total similarity TSM is calculated. After the calculation of the total similarity TSM for one case ends, the calculation of the individual similarities ISM, the creation of the combinations of completely different types, and the calculation of the total similarity are performed for the next case. This process is repeatedly performed for all of the cases.

In the event that the process of calculating the total similarity for one case is considered, the process which calculates the individual similarities ISM, creates combinations of completely different types of individual similarities ISM, and calculates the total similarity TSM for only combinations of completely different types is common to the above-mentioned methods. In the invention, any of the methods may be used. Of course, a similar case search device, a similar case search method, and a similar case search program according to the invention include any of the methods.

Second Embodiment

In the first embodiment, the case in which the number of types of case lesions CL is less than the number of regions of interest ROI is excluded from the search target. However, in a second embodiment illustrated in FIGS. 44 to 46, the case in which the number of types of case lesions CL is less than the number of regions of interest ROI may be included in the search target in the event that there are a plurality of types of case lesions CL. For example, as illustrated in FIG. 44, in the second embodiment, in a case in which three regions of interest ROI are designated, a case including two types of case lesions, such as the case with the case ID "C103" that is excluded from the search target in the first embodiment (see FIG. 35), is included in the search target.

In the second embodiment, a case with a case ID "C104" is excluded from the search target since it includes one type of case lesions. The reason is as follows. Since the total similarity TSM is the sum of a plurality of types of individual similarities ISM corresponding to a plurality of regions of interest ROI, it is difficult to calculate the total similarity TSM for the case in which the number of types of case lesions is "1".

It is preferable that the number of types of case lesions CL is equal to or greater than the number of regions of interest ROI in a case which is extracted as a similar case. The reason is as follows. In a case in which the similar case search process is used to diagnose a non-cancerous disease, the number of regions of interest ROI corresponds to the number of types of target lesions OL. However, in some cases, a small number of cases having a large number of types of case lesions CL are stored in the case DB 23. In this case, in the event that all of the cases in which the number of types of case lesions is less than the number of regions of interest ROI are excluded from the search targets, the number of search targets is too small and it is difficult to appropriately search for similar cases. Even in the cases in which the number of types of case lesions CL is less than the number of regions of interest ROI, each case lesion CL is likely to be useful for a diagnosis. In the second embodiment, it is assumed that there are two or more types of case lesions CL and the case in which the number of types of case lesions CL is less than the number of regions of interest ROI is included in the search target and can be extracted as a similar case. Since a method for calculating a feature amount or a method for calculating the individual similarity ISM is the same as that in the above-described embodiment, the description thereof will not be repeated. Therefore, the description is focused on the difference from the above-described embodiment.

Figure 45:
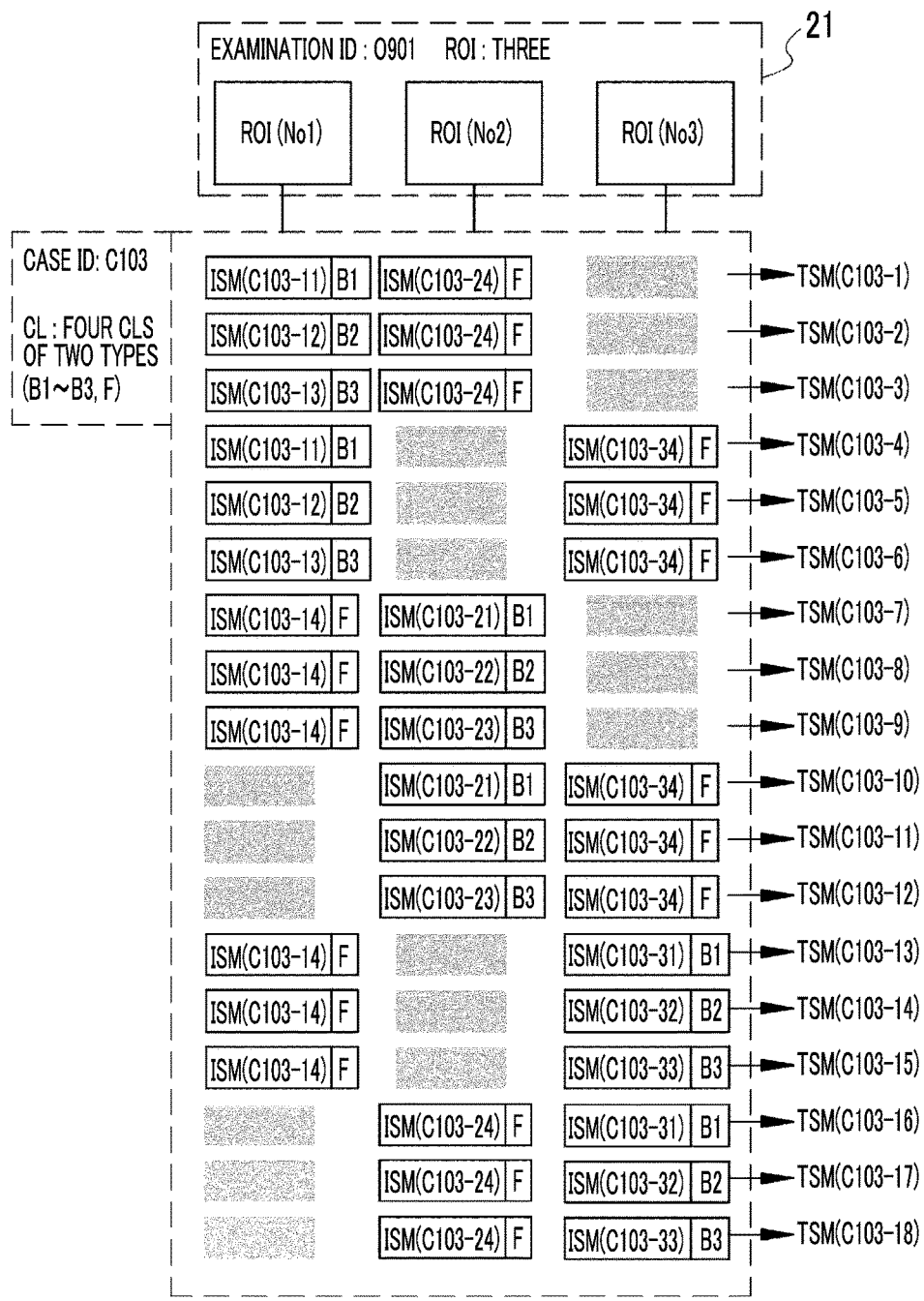
FIG. 45 is a diagram illustrating combinations of completely different types for four case lesions of two types in the second embodiment.

As illustrated in FIG. 45, the individual similarity calculation unit 65 sets two types of case lesions CL so as to correspond to the regions of interest ROI with No1 to No3 and calculates the individual similarities ISM. In FIG. 35, a hatched field indicates that there is no corresponding case lesion CL and the individual similarity ISM is not calculated. The total similarity calculation unit 66 creates combinations of completely different types of individual similarities ISM which are calculated by the correspondence between three regions of interest ROI and four case lesions CL of two types and determines that the combinations are used to calculate the total similarities TSM. In the case with the case ID "C103", combinations of completely different types are, for example, "B1, F" and "B2, F". In the case, the number of types is different from the number of regions of interest ROI. However, since the combinations do not include the individual similarities ISM of the same type calculated by the correspondence between the regions of interest ROI and the case lesions CL of the same type, the combinations are of completely different types. In contrast, combinations of the individual similarities of the same type, such as "B1, B2", are excluded from the target. As illustrated in FIG. 45, in the case of the case ID "C103", there are 18 combinations of completely different types and there are 18 total similarities TSM ("C103-1" to "C103-18").

Figure 46:
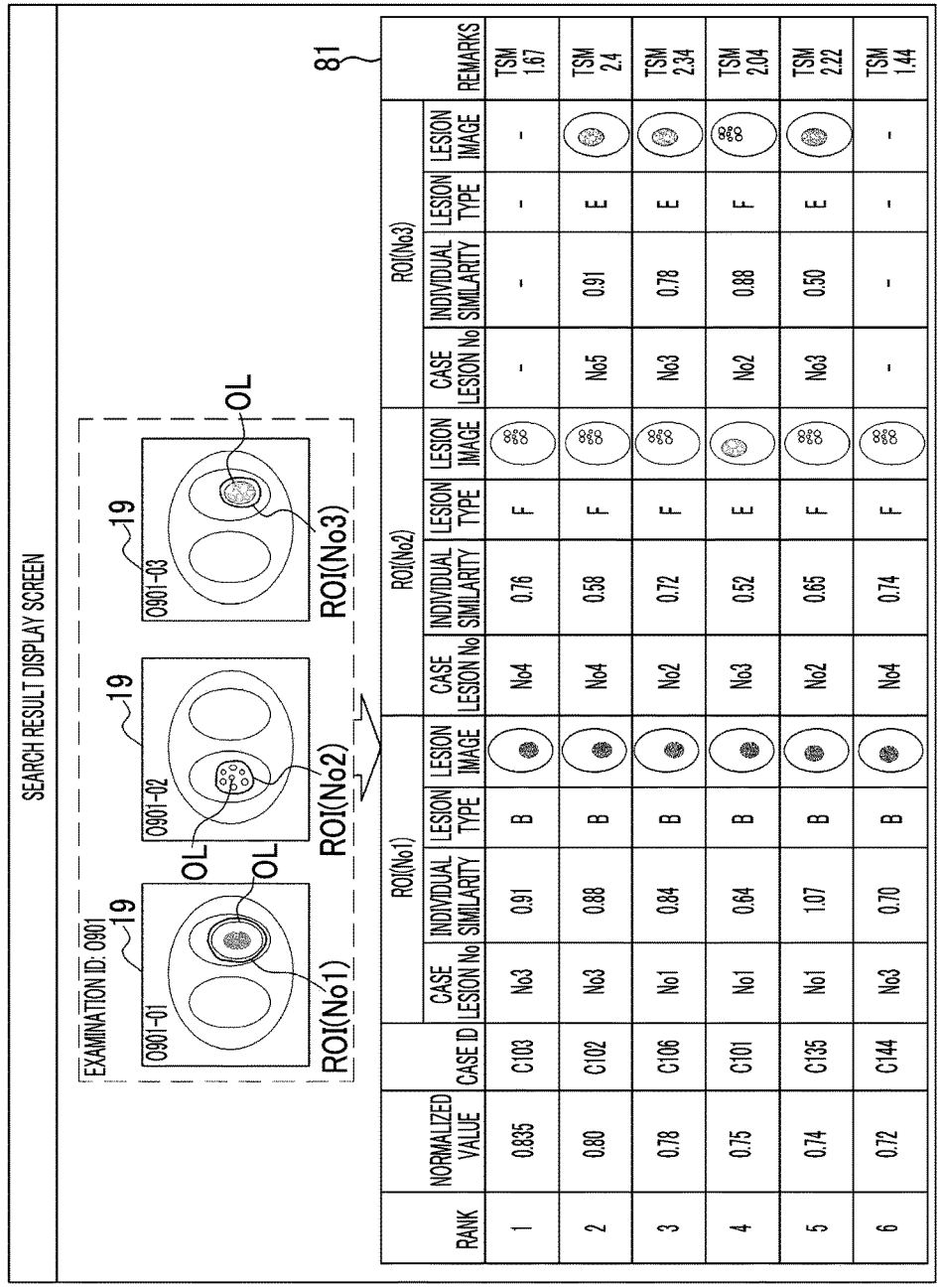
FIG. 46 is a diagram illustrating a search result display screen according to the second embodiment.

The similar case search unit 67 creates a similar case list 81 illustrated in FIG. 46. In the similar case list 81, the total similarity TSM ("1.67") for the case with the case ID "C103" is the sum of two types of individual similarities ISM and cannot be compared with the values of the total similarities TSM for other cases in which the total similarity TSM is the sum of three types of individual similarities ISM on the same basis. Therefore, the similar case search unit 67 performs normalization such that the total similarities TSM calculated on the basis of different numbers of individual similarities ISM can be compared with each other. The cases are ranked on the basis of normalized values which are normalized similarities. The normalization is, for example, a process that divides the total similarity TSM by the number of individual similarities ISM.

First, in the case with the case ID "C103", since the number of individual similarities ISM is 2, a normalized value ("0.835") is obtained by dividing the total similarity TSM ("1.67") by 2. In contrast, in other cases in which the number of individual similarities ISM is 3, a normalized value is obtained by dividing the total similarity TSM by 3. For example, in the case with the case ID "C106", since the total similarity TSM is "2.34", a value of "0.78" obtained by dividing the total similarity TSM by 3 is the normalized value.

According to this example, in the case DB 23, the case in which the number of types of case lesions CL is less than the number of regions of interest ROI, but is two or more can be included in the search target. Therefore, even in a case in which the number of cases registered in the case DB is small, a similar case search process can be performed effectively using the cases.

As a modification example of the second embodiment, the similar case search server 17 may re-search for a similar case, with a change in the number of designated regions of interest ROI. For example, a first similar case search request in which the number of designated regions of interest ROI is 2 is issued. The similar case search server 17 performs a similar case search process on the basis of the designation and transmits a similar case list 74 as the search result. The doctor sees the search result, additionally designates a new region of interest ROI, and issues a second similar case search request. The similar case search server 17 performs a similar case search process on the basis of the request including the added designation and transmits the similar case list 74 as the search result. Then, the doctor can change search conditions, assuming that it is necessary, while seeing the search result. Therefore, it is easy to appropriately search for a similar case. The number of designated regions of interest ROI may be increased or decreased.

In addition, the similar case search server 17 may comprise a re-search function and store data which has been created by an intermediate process of the similar case search or as the result of the process, such as the ISM table 71 or the TSM table 72. In the event that the data is used for a re-search process, it is possible to reduce the search time.

In the first and second embodiments, the example in which the total similarity TSM is the simple sum of a plurality of individual similarities ISM has been described. However, a weighting process may be performed on the basis of the values of the individual similarities ISM which are calculation elements. As an example of the weighting process, the following is considered: in a case in which the individual similarity ISM is equal to or greater than a threshold value, the individual similarity ISM is multiplied by a positive weighting coefficient to increase the total similarity TSM; and, in a case in which the individual similarity ISM is less than the threshold value, the individual similarity ISM is multiplied by a negative weighting coefficient to decrease the total similarity TSM. In some cases, a case including any case lesion CL that is very similar to the region of interest ROI is useful for a diagnosis. Positive weighting makes it easy to search for the case as a similar case.

In each of the above-described embodiments, the type of case lesion CL is determined in advance and information about the determined type is stored in the case DB 23. However, the type may be determined on the basis of the feature amount CAC at the time of a search, similarly to the region of interest ROI. In this case, since it takes time to perform a search process, it is preferable to store the type information in advance.

Third Embodiment

In each of the above-described embodiments, the individual similarities ISM are calculated by the correspondence between the regions of interest ROI and the case lesions CL, without determining the type of target lesion OL included in the region of interest ROI, and then similar cases are searched. However, in a third embodiment illustrated in FIGS. 47 to 51, a lesion type determination process may be performed for the target lesion OL included in the region of interest ROI and the case lesion CL, the individual similarities ISM may be calculated by only the correspondence between the lesions of the same type, and similar cases may be searched. As illustrated in FIG. 6, lesion patterns are typically distinguished by the type of lesion. Therefore, in a stage in which a feature amount is calculated, it is possible to determine the type of lesion on the basis of the feature amount. In the third embodiment, the determination of the type of lesion is used.

Figure 47:
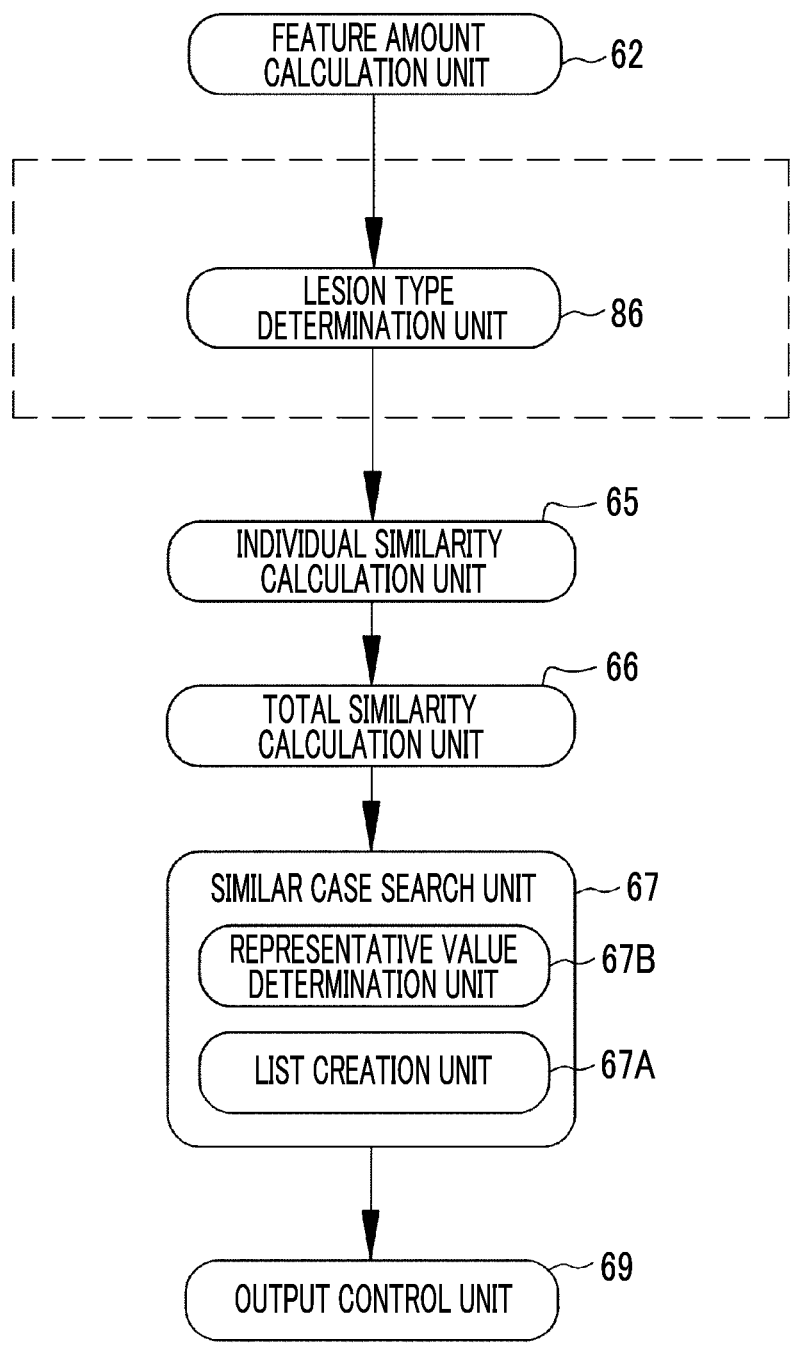
FIG. 47 is a diagram illustrating a third embodiment.
Figure 48:
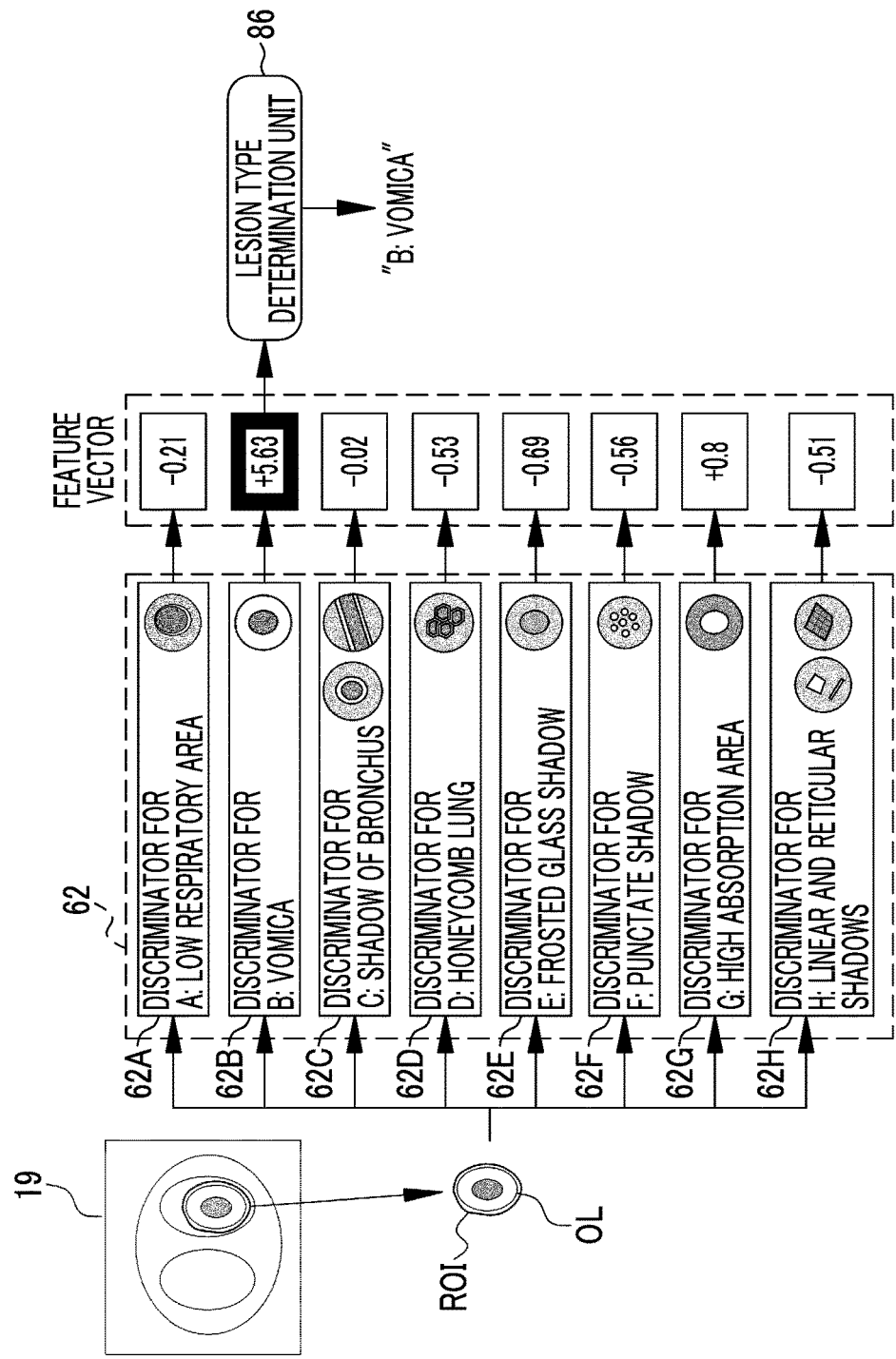
FIG. 48 is a diagram illustrating a lesion type determination unit.

As illustrated in FIG. 47, in the third embodiment, a similar case search server 17 is provided with a lesion type determination unit 86. As illustrated in FIG. 48, the lesion type determination unit 86 determines the type of target lesion OL included in the region of interest ROI on the basis of the feature amount RAC of the region of interest ROI calculated by a feature amount calculation unit 62. For example, the lesion type determination unit 86 determines the type of lesion corresponding to a discriminator indicating the maximum discriminator output value among the discriminator output values from discriminators 62A to 62H to be the type of target lesion OL included in the region of interest ROI. In this example, since the discriminator output value from the discriminator 62B corresponding to "B: vomica" is the maximum, the type of target lesion OL is determined to be "B: vomica".

Figure 49:
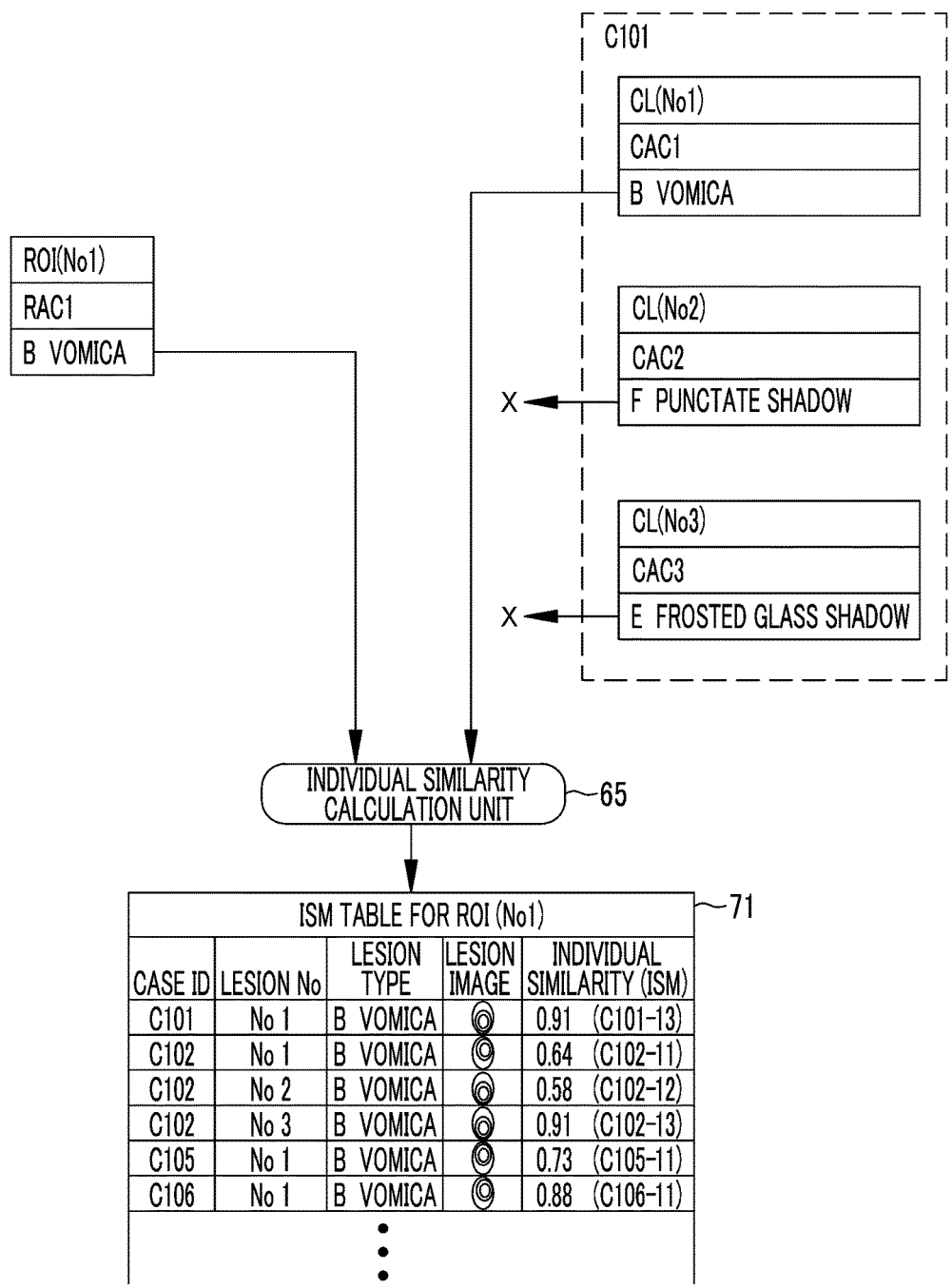
FIG. 49 is a diagram illustrating an individual similarity calculation unit according to the third embodiment.

As illustrated in FIG. 49, in the event of calculating the individual similarities ISM between the region of interest ROI and each case lesion CL, the individual similarity calculation unit 65 calculates the individual similarity ISM between the lesions of the same type and does not calculate the individual similarity ISM between different types of lesions. In this example, since a region of interest ROI with No1 is the type "B: vomica", the individual similarity calculation unit 65 calculates only the individual similarity ISM between the region of interest ROI and a case lesion CL with No3, of which the type is "B: vomica", in a case with a case ID "C101". In a case in which a plurality of case lesions CL which are the same type as the region of interest ROI are registered in one case, a plurality of individual similarities ISM are calculated. In a case in which no case lesion CL which is the same type as the region of interest ROI is registered, the individual similarity ISM is not calculated for the case.

Figure 50:
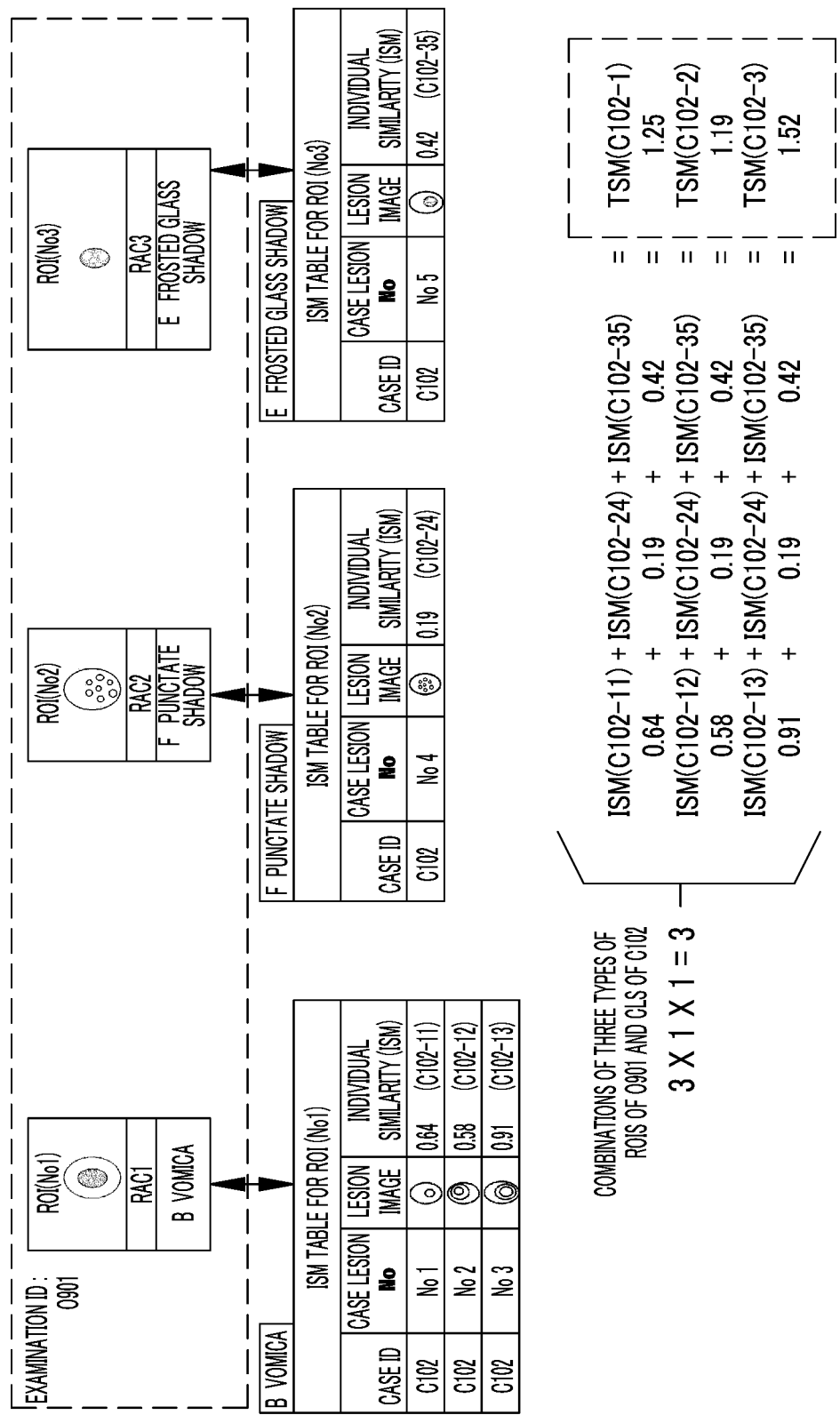
FIG. 50 is a diagram illustrating a table in which combinations of completely different types are arranged in the third embodiment.

In this way, it is possible to reduce the calculation time of the individual similarity calculation unit 65. In addition, the number of individual similarities ISM is reduced. Therefore, as illustrated in FIG. 50, the number of combinations of completely different types of individual similarities which are used to calculate the total similarity TSM is also reduced. In a case with a case ID "C102" including five case lesions of three types, while the number of combinations of completely different types is 18 in the event that the type of case lesion is not determined as in the first embodiment, the number of combinations of completely different types is 3 in the event that the type of case lesion is determined as in the this example. The total similarity calculation unit 66 calculates three total similarities TSM (C102-1 to C102-3) for these combinations.

As such, in the third embodiment, the time required to calculate the individual similarity ISM and the total similarity TSM is shorter than that in the first embodiment in which the individual similarity ISM is calculated, without distinguishing the types of case lesions. In addition, since the size of the ISM table 71 or the TSM table 72 is reduced, the work area of a memory is also reduced. Therefore, load applied to the CPU 41B of the similar case search server 17 is reduced. As a result, it is possible to reduce the search time.

Figure 11:
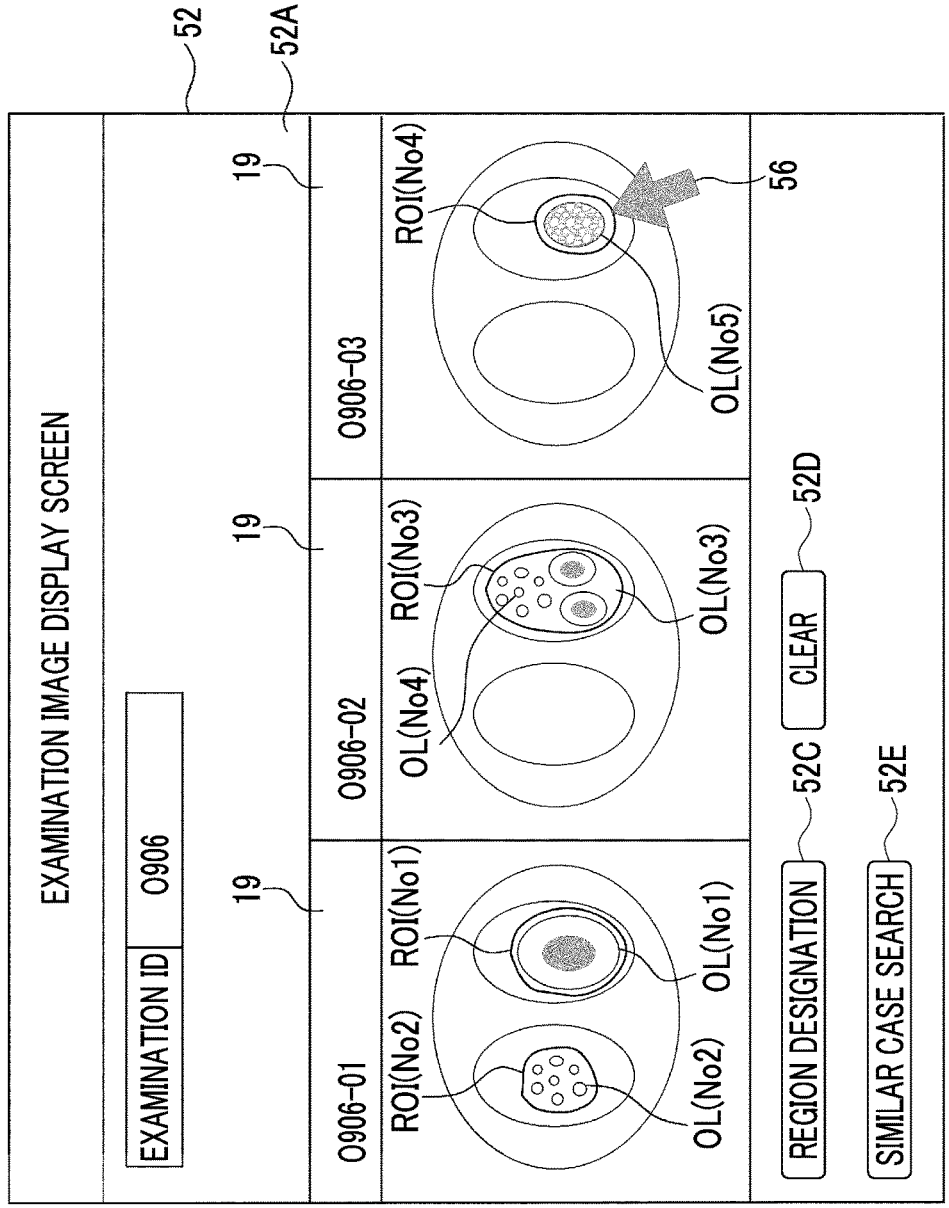
FIG. 11 is a diagram illustrating an example of a method for designating the region of interest which is different from that illustrated in FIG. 9.

However, in the aspect in which the type of lesion is determined in advance and only the individual similarity ISM between the lesions of the same type is calculated, in a case in which the accuracy of determining the type of lesion is low, so-called search omission in which the case lesion CL to be searched as a similar case is missed is likely to occur. In particular, as illustrated in FIG. 11, in a case in which a plurality of target lesions OL are designated as one region of interest ROI, the type of lesion is determined on the basis of only one of a plurality of target lesions OL. For this reason, it is preferable that the third embodiment is performed after the accuracy of determining the type of lesion is checked.

Fourth Embodiment

Figure 51:
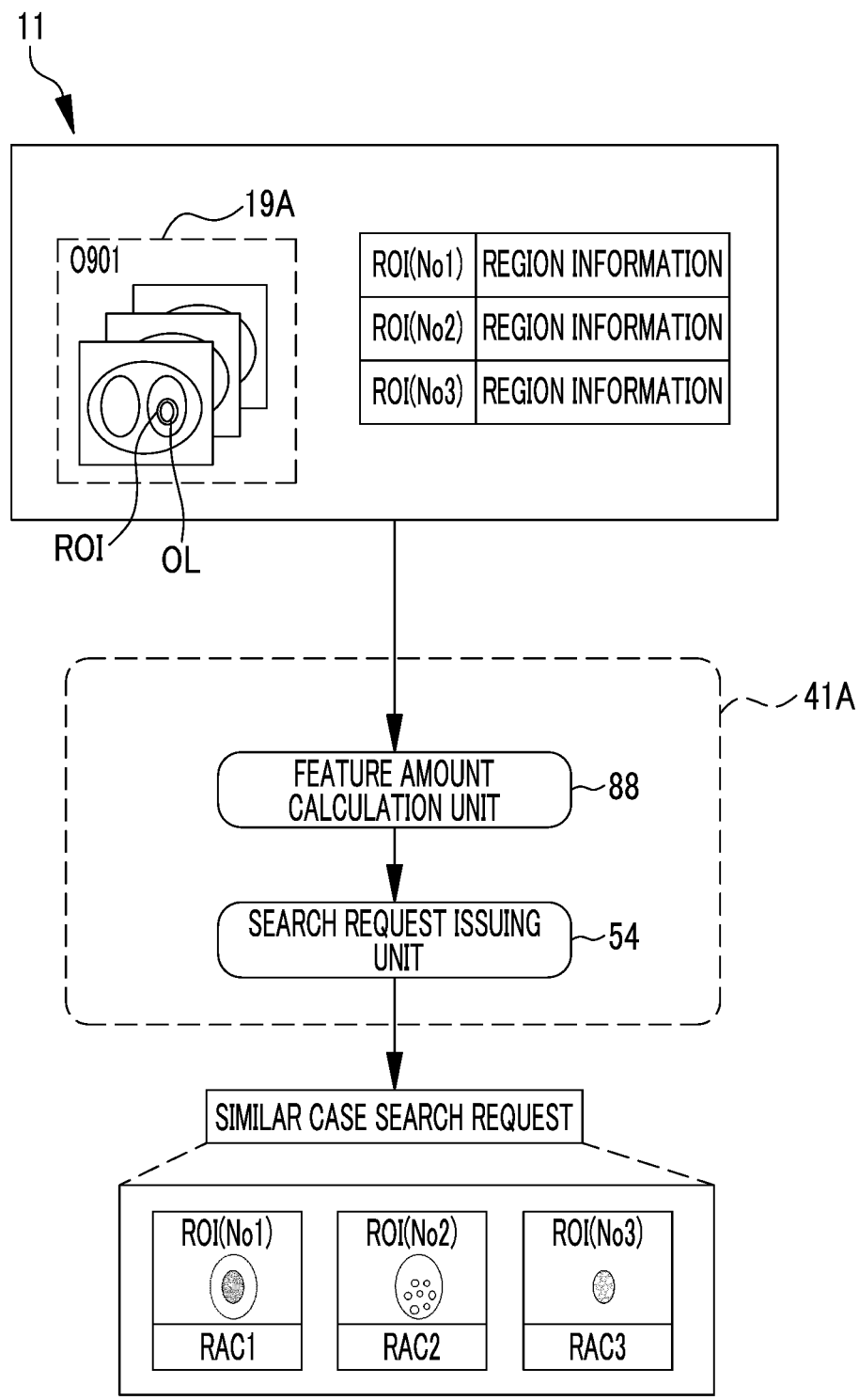
FIG. 51 is a diagram illustrating another example in which the treatment department terminal comprises the feature amount calculation unit.
Figure 52:
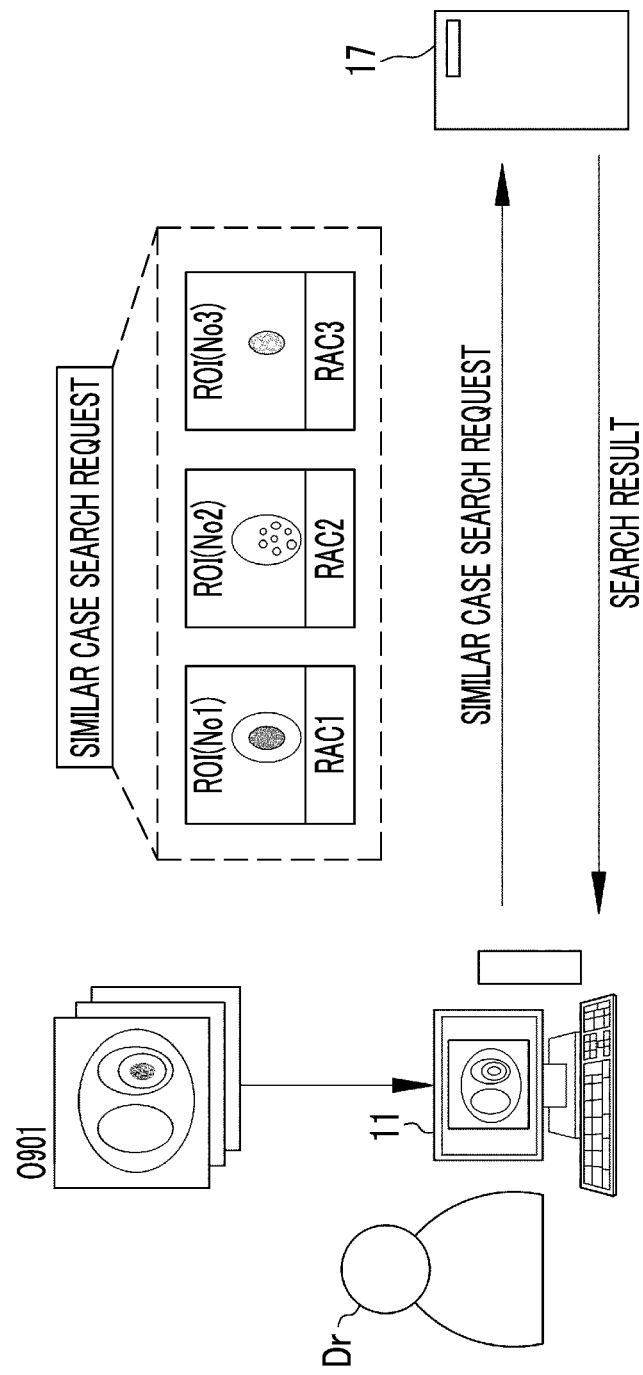
FIG. 52 is a diagram illustrating a similar case search server and the treatment department terminal illustrated in FIG. 51.

In a fourth embodiment illustrated in FIGS. 51 and 52, not the similar case search server 17 but the treatment department terminal 11 calculates the feature amount of the region of interest ROI. As in the fourth embodiment, the treatment department terminal 11 may calculate the feature amount of the region of interest ROI. In this case, the similar case search server 17 does not include the feature amount calculation unit 62 and includes structures other than the feature amount calculation unit 62, such as the individual similarity calculation unit 65, the total similarity calculation unit 66, and the similar case search unit 67 illustrated in FIG. 12.

As illustrated in FIG. 51, the treatment department terminal 11 is provided with a feature amount calculation unit 88 having the same structure as the feature amount calculation unit 62. For example, a CPU 41A executes software that is installed in the treatment department terminal 11 to implement the feature amount calculation unit 88. The feature amount calculation unit 88 calculates a feature amount RAC on the basis of examination data 21 including an examination image 19 and the region information of the region of interest ROI which is input through a GUI control unit 53. A search request issuing unit 54 attaches an image corresponding to the region of interest ROI and the calculated feature amount RAC to a similar case search request and issues the similar case search request.

As illustrated in FIG. 52, the similar case search request is transmitted from the treatment department terminal 11 to the similar case search server 17. The similar case search server 17 searches similar cases on the basis of the received similar case search request and transmits the search result to the treatment department terminal 11. In the fourth embodiment, the request receiving unit 61 of the similar case search server 17 functions as a feature amount acquisition unit.

In each of the above-described embodiments, the similar case search device according to the invention has been described in the form of the similar case search server 17 that searches for similar cases on the basis of the request from the treatment department terminal 11. However, the similar case search server 17 may not be used and the treatment department terminal 11 may be provided with a similar case search function such that the treatment department terminal 11 accesses the case DB server 16 and searches for similar cases. In this case, the treatment department terminal 11 is the similar case search device.

In each of the above-described embodiments, the similar case search server 17 and the case DB server 16 are provided as individual servers. However, the similar case search server 17 and the case DB server 16 may be integrated into one server. As such, a plurality of functions may be integrated into one server or may be distributed to different servers.

The hardware configuration of the computer system can be modified in various ways. For example, the similar case search server 17 may be formed by a plurality of server computers which are separated as hardware components in order to improve processing capability or reliability. As such, the hardware configuration of the computer system can be appropriately changed depending on required performances, such as processing capability, safety, and reliability. In addition to hardware, a program, such as the case DB 23 or the AP 50, may be duplicated or may be dispersedly stored in a plurality of storage devices in order to ensure safety or reliability.

In each of the above-described embodiments, the similar case search server 17 is used in one medical facility. However, the similar case search server 17 may be used in a plurality of medical facilities.

Specifically, in each of the above-described embodiments, the similar case search server 17 is connected to client terminals that are installed in one medical facility, such as the treatment department terminals 11, through a LAN such that it can communicate with the client terminals and provides application services related to a similar case search on the basis of requests from the client terminals. The similar case search server 17 is connected to the client terminals installed in a plurality of medical facilities through a wide area network (WAN), such as the Internet or a public telecommunication network, such that it can communicate with the client terminals. In this way, the similar case search server 17 can be used in a plurality of medical facilities. Then, the similar case search server 17 receives requests from the client terminals in the plurality of medical facilities and provides application services related to a similar case search to each client terminal.

In this case, the similar case search server 17 may be installed and operated by, for example, a data center different from the medical facilities or by one of the plurality of medical facilities. In a case in which the WAN is used, it is preferable to construct a virtual private network (VPN) or to use a communication protocol with a high security level, such as hypertext transfer protocol secure (HTTPS), considering information security.

The invention is not limited to each of the above-described embodiments and can use various structures, without departing from the scope and spirit of the invention. For example, in this example, CT images, MRI images, and plain X-ray images are given as examples of the examination image. However, the invention may be applied to examination images which are captured by other modalities, such as a mammography system or an endoscope. In addition, the above-mentioned various embodiments or various modification examples may be appropriately combined with each other. The invention is also applied to a storage medium that stores the program, in addition to the program for implementing the invention.

What is claimed is:

1. A similar case search device that searches for a similar case which is similar to an examination image used to diagnose a patient from a case database in which a plurality of cases, each of which includes one or more case images, are registered, comprising:
   a memory storing at least an individual similarity table and a total similarity table;
   a processor configured to:
      acquire feature amounts of a plurality of regions of interest, each of which is designated so as to include one or more different target lesions that are lesions in the examination images, in examination data including one or more examination images;
      set the regions of interest and a plurality of case lesions in the case image so as to be in one-to-one correspondence with each other, compares the feature amounts of the regions of interest and feature amounts of the case lesions which correspond to each other, and calculates an individual similarity for each region of interest;
      calculate a total similarity for only combinations of completely different types, which are combinations of the plurality of regions of interest and a plurality of different types of case lesions in the same case, on the basis of a plurality of individual similarities calculated for each of the plurality of regions of interest, thereby reducing a work area memory that is required to perform the similar case search; and
      search for the similar case on the basis of the total similarities corresponding to the combinations of completely different types, and
   a display for displaying results of the search for the similar case.

2. The similar case search device according to claim 1, wherein the processor is further configured to create the combinations of completely different types which correspond to the number of regions of interest, the number of types of case lesions, and the number of case lesions and calculates the total similarities for each of the combinations of completely different types.

3. The similar case search device according to claim 1, wherein, in a case in which there are a plurality of case lesions of at least one type among a plurality of different types of case lesions included in the same case, the processor is further configured to distinguish the plurality of case lesions of the same type and creates the combinations of completely different types for each of the distinguished case lesions of the same type.

4. The similar case search device according to claim 1, wherein the processor is further configured to create a similar case list which is a list of information related to the plurality of similar cases on the basis of the total similarities.

5. The similar case search device according to claim 4, wherein, in the similar case list, the similar cases are sorted in an order of the total similarity.

6. The similar case search device according to claim 4, wherein display items of the similar case list include a value of the total similarity and breakdown information related to the total similarity, and
the breakdown information includes a correspondence relationship between the region of interest and the case lesion for calculating the individual similarity.

7. The similar case search device according to claim 6, wherein, in addition to the value of the total similarity, values of the plurality of individual similarities which are elements for calculating the total similarity are displayed in the similar case list.

8. The similar case search device according to claim 4, wherein images of the region of interest and the case lesion are displayed in the similar case list.

9. The similar case search device according to claim 1, wherein the case database stores information about the type of the case lesion.

10. The similar case search device according to claim 1, wherein the total similarity is a sum of a plurality of individual similarities included in the combinations of completely different types.

11. The similar case search device according to claim 1, wherein the processor is further configured to create an individual similarity table, in which a plurality of individual similarities that are calculated by a correspondence between each region of interest and a plurality of case lesions are recorded, for each region of interest.

12. The similar case search device according to claim 11, wherein the processor is further configured to read out the individual similarities one by one from a plurality of individual similarity tables created for each region of interest and creates the combinations of completely different types, using the plurality of read individual similarities as elements.

13. The similar case search device according to claim 1, wherein the processor is further configured to calculate the individual similarity for a case in which at least the number of types of case lesions is two or more among the cases and does not calculate the individual similarity for a case in which the number of types of case lesions is one.

14. The similar case search device according to claim 1, wherein the processor is further configured to perform a weighting process for the total similarity according to values of the individual similarities which are elements for calculating the total similarity.

15. The similar case search device according to claim 14, wherein, in a case in which the individual similarity is equal to or greater than a threshold value, the weighting process increases the total similarity.

16. The similar case search device according to claim 1, wherein the processor is further configured to exclude a case in which the number of types of case lesions is less than the number of regions of interest from a search target.

17. The similar case search device according to claim 1, wherein the processor is further configured to set a case in which the number of types of case lesions is less than the number of regions of interest, but is two or more, as a search target.

18. The similar case search device according to claim 1, wherein, in a case in which a plurality of total similarities are calculated by a correspondence between one region of interest and a plurality of case lesions included in one case, the processor is further configured to determine one representative value from the plurality total similarities, and
wherein the processor is further configured to search for the similar case on the basis of the representative value.

19. A similar case search method that searches for a similar case which is similar to an examination image used to diagnose a patient from a case database in which a plurality of cases, each of which includes one or more case images, are registered, comprising:
a feature amount acquisition step of acquiring feature amounts of a plurality of regions of interest, each of which is designated so as to include one or more different target lesions that are lesions in the examination images, in examination data including one or more examination images;
an individual similarity calculation step of setting the regions of interest and a plurality of case lesions in the case image so as to be in one-to-one correspondence with each other, comparing the feature amounts of the regions of interest and feature amounts of the case lesions which correspond to each other, and calculating an individual similarity for each region of interest;
a total similarity calculation step of calculating a total similarity for only combinations of completely different types, which are combinations of the plurality of regions of interest and a plurality of different types of case lesions in the same case, on the basis of a plurality of individual similarities calculated for each of the plurality of regions of interest, thereby reducing a work area memory that is required to perform the similar case search, wherein the individual similarity and the total similarity are stored in a memory storing at least an individual similarity table and a total similarity table;
a similar case search step of searching for the similar case on the basis of the total similarities corresponding to the combinations of completely different types, and
a display step of displaying results of the search for the similar case.

20. A non-transitory computer readable medium for storing a computer-executable program enabling execution of computer instructions to perform operations for searching for a similar case which is similar to an examination image used to diagnose a patient from a case database in which a plurality of cases, each of which includes one or more case images, are registered, said operations comprising:
acquiring feature amounts of a plurality of regions of interest, each of which is designated so as to include one or more different target lesions that are lesions in the examination images, in examination data including one or more examination images;
setting the regions of interest and a plurality of case lesions in the case image so as to be in one-to-one correspondence with each other, comparing the feature amounts of the regions of interest and feature amounts of the case lesions which correspond to each other, and calculating an individual similarity for each region of interest;
calculating a total similarity for only combinations of completely different types, which are combinations of the plurality of regions of interest and a plurality of different types of case lesions in the same case, on the basis of a plurality of individual similarities calculated for each of the plurality of regions of interest, thereby reducing a work area memory that is required to perform the similar case search, wherein the individual similarity and the total similarity are stored in a memory storing at least an individual similarity table and a total similarity table;
searching for the similar case on the basis of the total similarities corresponding to the combinations of completely different types; and
displaying results of the search for the similar case.

* * * * *